(12) United States Patent
Trabish et al.

(10) Patent No.: US 11,399,818 B2
(45) Date of Patent: Aug. 2, 2022

(54) SURGICAL APPARATUS TO SUPPORT INSTALLATION OF A PROSTHETIC COMPONENT WITH REDUCED ALIGNMENT ERROR

(71) Applicant: Orthosensor Inc., Dania, FL (US)

(72) Inventors: Masei Trabish, Folsom, CA (US); Martin Roche, Fort Lauderdale, FL (US); Ivan Delevic, Key Biscayne, FL (US); Gordon Goodchild, Coral Springs, FL (US); Byung Jai Lee, Guri-Si (KR)

(73) Assignee: Orthosensor Inc., Dania Beach, FL (US)

( * ) Notice: Subject to any disclaimer, the term of this patent is extended or adjusted under 35 U.S.C. 154(b) by 197 days.

(21) Appl. No.: 15/852,051

(22) Filed: Dec. 22, 2017

(65) Prior Publication Data
US 2018/0177612 A1 Jun. 28, 2018

Related U.S. Application Data

(60) Provisional application No. 62/438,406, filed on Dec. 22, 2016.

(51) Int. Cl.
*A61B 17/02* (2006.01)
*A61B 17/15* (2006.01)
(Continued)

(52) U.S. Cl.
CPC .......... *A61B 17/025* (2013.01); *A61B 5/4528* (2013.01); *A61B 17/155* (2013.01); *A61B 17/1626* (2013.01); *A61B 17/1764* (2013.01); *A61B 17/8866* (2013.01); *A61B 34/10* (2016.02); *A61B 90/06* (2016.02); *A61F 2/3859* (2013.01); *A61F 2/3872* (2013.01);
(Continued)

(58) Field of Classification Search
CPC ... A61B 17/155; A61B 17/157; A61B 17/025; A61B 2017/0268; A61B 17/1764; A61B 17/8866; A61B 5/4528
See application file for complete search history.

(56) References Cited

U.S. PATENT DOCUMENTS

| 4,501,266 A | 2/1985 | McDaniel |
| 4,566,448 A | 1/1986 | Rohr, Jr. |

(Continued)

*Primary Examiner* — Matthew J Lawson
(74) *Attorney, Agent, or Firm* — Lerner, David, Littenberg, Krumholz & Mentlik, LLP

(57) ABSTRACT

A surgical apparatus is configured to support at least one bone cut for installation of a prosthetic component. The installed prosthetic component will have reduced alignment error. The surgical apparatus is configured to distract a first compartment to a first predetermined load value while allowing a moving support structure to pivot freely. A distraction lock mechanism is then engaged to prevent movement of a distraction mechanism that raises or lowers the moving support structure relative to a fixed support structure. The moving support structure has M-L tilt angle that is measured. A M-L tilt mechanism is engaged to forcibly equalize the first and second compartments. Engaging the M-L tilt mechanism prevents the moving support structure from freely pivoting. The at least one bone cut relates to the first and second compartments equalized and the M-L tilt angle.

20 Claims, 32 Drawing Sheets

(51) Int. Cl.
  *A61B 17/17* (2006.01)
  *A61B 5/00* (2006.01)
  *A61B 17/16* (2006.01)
  *A61F 2/46* (2006.01)
  *A61B 17/88* (2006.01)
  *A61B 90/00* (2016.01)
  *A61F 2/38* (2006.01)
  *A61B 34/10* (2016.01)
  *A61B 17/00* (2006.01)
  *A61F 2/30* (2006.01)

(52) U.S. Cl.
  CPC ............ *A61F 2/461* (2013.01); *A61F 2/4657* (2013.01); *A61F 2/4684* (2013.01); *A61B 5/4504* (2013.01); *A61B 5/4585* (2013.01); *A61B 5/4851* (2013.01); *A61B 2017/00039* (2013.01); *A61B 2017/0268* (2013.01); *A61B 2090/061* (2016.02); *A61B 2090/064* (2016.02); *A61B 2090/067* (2016.02); *A61B 2562/0223* (2013.01); *A61B 2562/0252* (2013.01); *A61F 2/3094* (2013.01); *A61F 2/38* (2013.01); *A61F 2/3886* (2013.01); *A61F 2002/30522* (2013.01); *A61F 2002/30525* (2013.01); *A61F 2002/30538* (2013.01); *A61F 2002/30556* (2013.01); *A61F 2002/30579* (2013.01); *A61F 2002/30616* (2013.01); *A61F 2002/469* (2013.01); *A61F 2002/4627* (2013.01); *A61F 2002/4658* (2013.01); *A61F 2002/4666* (2013.01); *A61F 2002/4668* (2013.01)

(56) References Cited

U.S. PATENT DOCUMENTS

| | | | |
|---|---|---|---|
| 4,703,751 A * | 11/1987 | Pohl | A61B 17/155 606/53 |
| 5,116,338 A | 5/1992 | Poggie et al. | |
| 5,213,112 A | 5/1993 | Niwa et al. | |
| 5,431,653 A | 7/1995 | Callaway | |
| 5,468,244 A | 11/1995 | Attfield et al. | |
| 5,470,354 A | 11/1995 | Hershberger et al. | |
| 5,540,696 A | 7/1996 | Booth, Jr. et al. | |
| 5,569,260 A | 10/1996 | Petersen | |
| 5,597,379 A * | 1/1997 | Haines | A61B 17/1764 606/80 |
| 5,669,914 A | 9/1997 | Eckhoff | |
| 5,688,280 A | 11/1997 | Booth, Jr. et al. | |
| 5,733,292 A | 3/1998 | Gustilo et al. | |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A * | 2/2000 | Nuelle | A61B 17/025 606/102 |
| 6,478,799 B1 | 11/2002 | Williamson | |
| 6,648,896 B2 | 11/2003 | Overes et al. | |
| 6,758,850 B2 | 7/2004 | Smith et al. | |
| 6,770,078 B2 | 8/2004 | Bonutti | |
| 6,859,661 B2 | 2/2005 | Tuke | |
| 7,156,853 B2 | 1/2007 | Muratsu | |
| 7,179,295 B2 | 2/2007 | Kovacevic | |
| 7,309,339 B2 * | 12/2007 | Cusick | A61B 17/154 606/88 |
| 7,329,260 B2 | 2/2008 | Auger et al. | |
| 7,381,223 B2 | 6/2008 | Kovacevic | |
| 7,412,897 B2 | 8/2008 | Crottet et al. | |
| 7,442,196 B2 | 10/2008 | Fisher et al. | |
| 7,455,647 B2 | 11/2008 | Tarabichi | |
| 7,470,288 B2 | 12/2008 | Dietz et al. | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,591,854 B2 | 9/2009 | Wasielewski | |
| 7,615,055 B2 | 11/2009 | DiSilvestro | |
| 7,632,283 B2 | 12/2009 | Heldreth | |
| 7,635,369 B2 | 12/2009 | Cinquin et al. | |
| 7,651,500 B2 | 1/2010 | Supper et al. | |
| 7,837,691 B2 | 11/2010 | Cordes et al. | |
| 7,849,751 B2 | 12/2010 | Clark et al. | |
| 7,927,336 B2 | 4/2011 | Rasmussen | |
| 7,978,091 B2 | 7/2011 | Boillot | |
| 8,025,663 B2 | 9/2011 | Keeven et al. | |
| 8,065,927 B2 | 11/2011 | Crottet et al. | |
| 8,118,815 B2 | 2/2012 | Van Der Walt | |
| 8,137,361 B2 | 3/2012 | Duggineni et al. | |
| 8,141,437 B2 | 3/2012 | Amirouche et al. | |
| 8,162,951 B2 | 4/2012 | Kaufman | |
| 8,197,489 B2 | 6/2012 | Chessar et al. | |
| 8,197,549 B2 | 6/2012 | Amirouche et al. | |
| 8,211,041 B2 | 7/2012 | Fisher et al. | |
| 8,231,631 B2 | 7/2012 | Lavallee et al. | |
| 8,234,929 B2 | 8/2012 | Clark et al. | |
| 8,273,131 B2 | 9/2012 | Metzger et al. | |
| 8,303,597 B2 | 11/2012 | Rasmussen | |
| 8,323,290 B2 * | 12/2012 | Metzger | A61B 17/025 606/90 |
| 8,337,508 B2 | 12/2012 | Lavallee et al. | |
| 8,394,104 B2 | 3/2013 | DiSilvestro | |
| 8,414,653 B2 | 4/2013 | Burstein et al. | |
| 8,421,642 B1 | 4/2013 | McIntosh et al. | |
| 8,491,589 B2 | 7/2013 | Fisher et al. | |
| 8,506,571 B2 | 8/2013 | Chana et al. | |
| 8,551,023 B2 | 10/2013 | Sherman et al. | |
| 8,556,830 B2 | 10/2013 | Sherman et al. | |
| 8,562,617 B2 | 10/2013 | Chessar et al. | |
| 8,597,210 B2 | 12/2013 | Sherman et al. | |
| 8,603,101 B2 | 12/2013 | Claypool et al. | |
| 8,715,290 B2 | 5/2014 | Fisher et al. | |
| 8,721,568 B2 | 5/2014 | Rock et al. | |
| 8,734,454 B2 | 5/2014 | DiSilvestro | |
| 8,740,817 B2 | 6/2014 | Sherman et al. | |
| 8,758,355 B2 | 6/2014 | Fisher et al. | |
| 8,784,339 B2 | 7/2014 | Stein et al. | |
| 8,784,490 B2 | 7/2014 | Wasielewski | |
| 8,820,173 B2 | 9/2014 | Clark et al. | |
| 8,876,831 B2 | 11/2014 | Rasmussen | |
| 8,906,027 B2 | 12/2014 | Roche | |
| 8,945,026 B2 | 2/2015 | Moser et al. | |
| 8,945,132 B2 | 2/2015 | Plaßy et al. | |
| 8,945,133 B2 | 2/2015 | Stein et al. | |
| 8,974,459 B1 | 3/2015 | Axelson, Jr. et al. | |
| 8,998,910 B2 | 4/2015 | Borja et al. | |
| 8,998,917 B2 | 4/2015 | Colquhoun et al. | |
| 9,011,459 B2 | 4/2015 | Claypool et al. | |
| 9,044,218 B2 | 6/2015 | Young | |
| 9,050,107 B2 | 6/2015 | Sordelet et al. | |
| 9,050,197 B2 | 6/2015 | Lorio et al. | |
| 9,084,612 B2 | 7/2015 | Sordelet et al. | |
| 9,113,957 B2 | 8/2015 | Axelson, Jr. et al. | |
| 9,138,238 B2 | 9/2015 | Sordelet et al. | |
| 9,138,332 B2 | 9/2015 | Harris et al. | |
| 9,144,495 B2 | 9/2015 | Lin et al. | |
| 9,149,206 B2 | 10/2015 | Claypool et al. | |
| 9,168,032 B2 | 10/2015 | Hutchison et al. | |
| 9,192,391 B2 | 11/2015 | Haines | |
| 9,192,392 B2 | 11/2015 | Van Der Walt et al. | |
| 9,216,097 B2 | 12/2015 | Hauri et al. | |
| 9,241,801 B1 | 1/2016 | Parry et al. | |
| 9,248,030 B2 | 2/2016 | Amirouche | |
| 9,265,462 B2 | 2/2016 | McIntosh et al. | |
| 9,271,756 B2 | 3/2016 | van der Walt et al. | |
| 9,307,929 B2 | 4/2016 | Colwell, Jr. et al. | |
| 9,339,226 B2 | 5/2016 | van der Walt et al. | |
| 9,351,850 B2 | 5/2016 | Fischer et al. | |
| 9,370,375 B2 | 6/2016 | Kaneyama et al. | |
| 9,381,011 B2 | 7/2016 | Ruhling et al. | |
| 9,427,336 B2 | 8/2016 | Axelson, Jr. et al. | |
| 9,427,337 B2 | 8/2016 | Claypool et al. | |
| 9,439,656 B2 * | 9/2016 | Chana | A61B 17/155 |
| 9,456,769 B2 | 10/2016 | Stein et al. | |
| 9,480,482 B2 | 11/2016 | Sordelet et al. | |

(56) References Cited

U.S. PATENT DOCUMENTS

| | | |
|---|---|---|
| 9,492,179 B2 | 11/2016 | Rasmussen |
| 9,492,180 B2 | 11/2016 | Rasmussen |
| 9,492,186 B2 | 11/2016 | Ghijselings |
| 9,492,290 B2 | 11/2016 | Claypool et al. |
| 9,498,199 B2 | 11/2016 | Colquhoun et al. |
| 9,498,235 B2 | 11/2016 | Ghijselings |
| 9,538,953 B2 | 1/2017 | Sherman et al. |
| 9,539,116 B2 | 1/2017 | Claypool et al. |
| 9,545,459 B2 | 1/2017 | Scott et al. |
| 9,554,745 B2 | 1/2017 | Nguyen et al. |
| 9,572,586 B2 | 2/2017 | Van Der Walt et al. |
| 9,572,588 B2 | 2/2017 | Fisher et al. |
| 9,573,322 B2 | 2/2017 | Wasielewski |
| 9,592,133 B2 | 3/2017 | Toler et al. |
| 9,597,090 B2 | 3/2017 | Claypool et al. |
| 9,597,096 B2 | 3/2017 | Aghazadeh |
| 9,597,158 B2 | 3/2017 | Colwell, Jr. et al. |
| 9,615,887 B2 | 4/2017 | Stein et al. |
| 9,622,761 B2 | 4/2017 | Chana et al. |
| 9,642,571 B2 | 5/2017 | McIntosh et al. |
| 9,642,676 B2 | 5/2017 | Stein et al. |
| 9,649,119 B2 | 5/2017 | Rock et al. |
| 9,693,881 B2 | 7/2017 | Lorio et al. |
| 9,724,110 B2 | 8/2017 | Cole |
| 9,750,619 B2 | 9/2017 | Rock |
| 9,763,807 B2 | 9/2017 | Claypool et al. |
| 9,775,595 B2 | 10/2017 | Vogt |
| 9,775,725 B2 | 10/2017 | Van Der Walt et al. |
| 9,782,249 B2 | 10/2017 | Hauri et al. |
| 9,808,356 B2 | 11/2017 | Haight et al. |
| 9,820,678 B2 | 11/2017 | Stein et al. |
| 9,839,533 B2 | 12/2017 | Nguyen et al. |
| 9,855,057 B2 | 1/2018 | Axelson, Jr. et al. |
| 9,901,331 B2 | 2/2018 | Toler et al. |
| 9,962,172 B2 | 5/2018 | Hutchison et al. |
| 9,980,735 B2 | 5/2018 | Chana et al. |
| 9,993,354 B2 | 6/2018 | Fisher et al. |
| 10,010,329 B2 | 7/2018 | Sordelet et al. |
| 10,010,330 B2 * | 7/2018 | Claypool ............ A61B 17/157 |
| 10,064,671 B2 | 9/2018 | Sharkey et al. |
| 10,070,973 B2 | 9/2018 | Sherman et al. |
| 10,076,344 B2 | 9/2018 | Toler |
| 10,080,617 B2 | 9/2018 | Haider et al. |
| 10,092,362 B2 | 10/2018 | Wasielewski |
| 10,772,640 B2 | 9/2020 | Trabish et al. |
| 10,772,641 B2 | 9/2020 | Trabish et al. |
| 2003/0069644 A1 | 4/2003 | Kovacevic et al. |
| 2003/0187452 A1 | 10/2003 | Smith et al. |
| 2004/0097951 A1* | 5/2004 | Steffensmeier ........ A61B 5/107 |
| | | 606/102 |
| 2004/0122441 A1* | 6/2004 | Muratsu ............ A61B 17/0206 |
| | | 606/102 |
| 2005/0038442 A1 | 2/2005 | Freeman |
| 2005/0149037 A1 | 7/2005 | Steffensmeier et al. |
| 2005/0256527 A1 | 11/2005 | Delfosse et al. |
| 2006/0111726 A1 | 5/2006 | Felt et al. |
| 2006/0241569 A1 | 10/2006 | DiSilvestro |
| 2006/0241640 A1 | 10/2006 | Briard et al. |
| 2006/0247646 A1* | 11/2006 | Bihary ............ A61B 17/157 |
| | | 606/87 |
| 2007/0005073 A1* | 1/2007 | Claypool ............ A61B 17/155 |
| | | 606/87 |
| 2007/0066917 A1 | 3/2007 | Hodorek et al. |
| 2007/0162036 A1 | 7/2007 | Schifrine et al. |
| 2007/0233267 A1 | 10/2007 | Amirouche et al. |
| 2007/0239157 A1 | 10/2007 | Guillaume |
| 2007/0244488 A1 | 10/2007 | Metzger et al. |
| 2007/0293868 A1* | 12/2007 | Delfosse ............ A61B 17/025 |
| | | 606/88 |
| 2008/0051798 A1 | 2/2008 | Colquhoun et al. |
| 2008/0269596 A1 | 10/2008 | Revie et al. |
| 2009/0018544 A1 | 1/2009 | Heavener |
| 2009/0222089 A1* | 9/2009 | Hauri ............ A61B 17/025 |
| | | 623/13.13 |
| 2009/0264894 A1* | 10/2009 | Wasielewski ............ A61F 2/38 |
| | | 606/102 |
| 2009/0270869 A1 | 10/2009 | Colquhoun et al. |
| 2010/0191068 A1 | 7/2010 | Bewernitz et al. |
| 2010/0198275 A1 | 8/2010 | Chana et al. |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249665 A1 | 9/2010 | Roche |
| 2010/0249787 A1 | 9/2010 | Roche |
| 2010/0249788 A1* | 9/2010 | Roche .................. A61B 5/1076 |
| | | 606/87 |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2011/0046685 A1 | 2/2011 | Faure et al. |
| 2011/0196370 A1 | 8/2011 | Mikhail |
| 2011/0213221 A1 | 9/2011 | Roche |
| 2012/0172762 A1 | 7/2012 | Boyer et al. |
| 2012/0172881 A1 | 7/2012 | Hutchison |
| 2012/0179069 A1 | 7/2012 | Amirouche |
| 2012/0259342 A1* | 10/2012 | Chana .................. A61B 17/025 |
| | | 606/88 |
| 2012/0290088 A1 | 11/2012 | Amirouche et al. |
| 2013/0023794 A1 | 1/2013 | Stein et al. |
| 2013/0023795 A1 | 1/2013 | Stein et al. |
| 2013/0030538 A1 | 1/2013 | Metzger et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0102929 A1* | 4/2013 | Haight .................. A61F 2/4657 |
| | | 600/587 |
| 2013/0138112 A1* | 5/2013 | Young .................. A61B 17/025 |
| | | 606/90 |
| 2013/0204157 A1 | 8/2013 | Clark et al. |
| 2013/0261503 A1 | 10/2013 | Sherman et al. |
| 2013/0261505 A1 | 10/2013 | Sherman et al. |
| 2013/0261631 A1 | 10/2013 | Ruhling |
| 2013/0261758 A1 | 10/2013 | Claypool et al. |
| 2013/0261759 A1 | 10/2013 | Claypool et al. |
| 2014/0025081 A1* | 1/2014 | Lorio ........................ A61F 2/38 |
| | | 606/102 |
| 2014/0066934 A1 | 3/2014 | Deirmengian et al. |
| 2014/0094715 A1 | 4/2014 | Stein et al. |
| 2014/0114319 A1 | 4/2014 | Wilkinson |
| 2014/0276861 A1 | 9/2014 | Stein et al. |
| 2014/0276886 A1 | 9/2014 | Stein et al. |
| 2014/0288563 A1* | 9/2014 | Claypool ............ A61B 17/155 |
| | | 606/88 |
| 2014/0309560 A1 | 10/2014 | Bonutti |
| 2015/0025537 A1 | 1/2015 | Ghijselings |
| 2015/0051455 A1 | 2/2015 | Wasielewski et al. |
| 2015/0088140 A1* | 3/2015 | Toler .................... A61B 17/025 |
| | | 606/88 |
| 2015/0105782 A1 | 4/2015 | D'Lima et al. |
| 2015/0201886 A1 | 7/2015 | Clark et al. |
| 2015/0209158 A1 | 7/2015 | Reeve |
| 2015/0230804 A1 | 8/2015 | Chana et al. |
| 2015/0238202 A1 | 8/2015 | Collins et al. |
| 2015/0265291 A1 | 9/2015 | Wilkinson |
| 2015/0359642 A1 | 12/2015 | Claypool et al. |
| 2016/0007909 A1 | 1/2016 | Singh et al. |
| 2016/0106409 A1 | 4/2016 | Moholkar |
| 2016/0135825 A1 | 5/2016 | Toler |
| 2016/0175117 A1 | 6/2016 | Colwell, Jr. et al. |
| 2016/0228193 A1 | 8/2016 | Moctezuma de la Barrera et al. |
| 2016/0278754 A1 | 9/2016 | Todorov et al. |
| 2016/0278787 A1 | 9/2016 | Axelson, Jr. et al. |
| 2016/0278944 A1 | 9/2016 | D'Lima et al. |
| 2016/0310122 A1 | 10/2016 | Ruhling et al. |
| 2016/0346044 A1 | 12/2016 | Brown et al. |
| 2017/0007225 A1 | 1/2017 | Ferro et al. |
| 2017/0007408 A1 | 1/2017 | Fitz et al. |
| 2017/0042554 A1 | 2/2017 | Chana et al. |
| 2017/0042558 A1 | 2/2017 | Ghijselings |
| 2017/0079670 A1 | 3/2017 | Haines |

(56) References Cited

U.S. PATENT DOCUMENTS

| | | |
|---|---|---|
| 2017/0079801 A1* | 3/2017 | Drury ................. A61F 2/28 |
| 2017/0128057 A1 | 5/2017 | Rasmussen |
| 2017/0128078 A1 | 5/2017 | Rasmussen |
| 2017/0143324 A1 | 5/2017 | Toler et al. |
| 2017/0156736 A1 | 6/2017 | Claypool et al. |
| 2017/0196515 A1 | 7/2017 | Clark et al. |
| 2017/0245872 A1 | 8/2017 | Rock et al. |
| 2017/0252186 A1 | 9/2017 | Lorio et al. |
| 2017/0312099 A1 | 11/2017 | Paszicsnyek |
| 2017/0325868 A1 | 11/2017 | Dungy |
| 2017/0333018 A1 | 11/2017 | Sehat |
| 2017/0333058 A1 | 11/2017 | Cabot |
| 2017/0333059 A1 | 11/2017 | Cole |
| 2017/0333220 A1 | 11/2017 | Reeve |
| 2017/0360512 A1 | 12/2017 | Couture et al. |
| 2017/0360576 A1 | 12/2017 | Rock |
| 2018/0000612 A1 | 1/2018 | Claypool et al. |
| 2018/0021151 A1 | 1/2018 | Mantovani et al. |
| 2018/0036015 A1 | 2/2018 | Bonutti |
| 2018/0049895 A1 | 2/2018 | Haight et al. |
| 2018/0085134 A1 | 3/2018 | Uthgenannt |
| 2018/0098774 A1 | 4/2018 | Bonutti |
| 2018/0132949 A1 | 5/2018 | Merette et al. |
| 2018/0168826 A1 | 6/2018 | van der Walt et al. |
| 2018/0177509 A1 | 6/2018 | Trabish et al. |
| 2018/0177607 A1 | 6/2018 | Trabish et al. |
| 2018/0177611 A1 | 6/2018 | Trabish et al. |
| 2018/0177612 A1 | 6/2018 | Trabish et al. |
| 2018/0199952 A1 | 7/2018 | Cole |
| 2018/0214283 A1 | 8/2018 | Johannaber et al. |
| 2018/0221008 A1 | 8/2018 | Todorov et al. |
| 2019/0008500 A1* | 1/2019 | Plaskos .................. A61B 90/06 |
| 2019/0110905 A1* | 4/2019 | Cabot ...................... A61F 2/38 |
| 2019/0167447 A1 | 6/2019 | Angibaud |
| 2020/0155135 A1 | 5/2020 | Cole et al. |
| 2020/0305942 A1 | 10/2020 | Oden et al. |

* cited by examiner

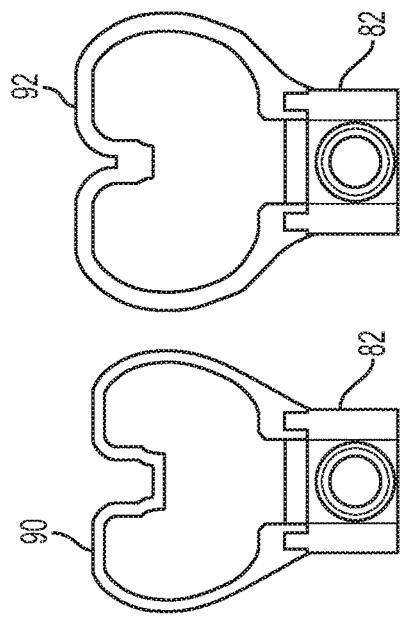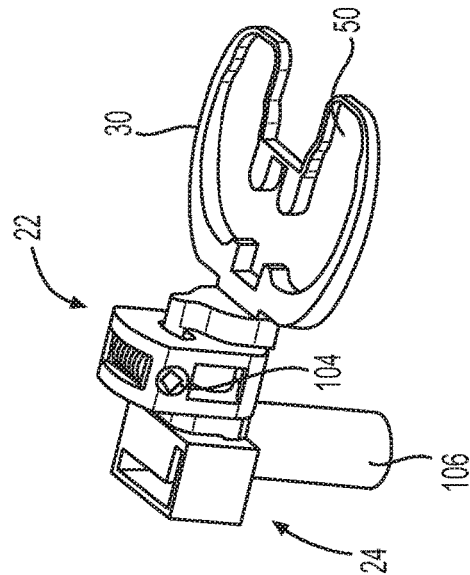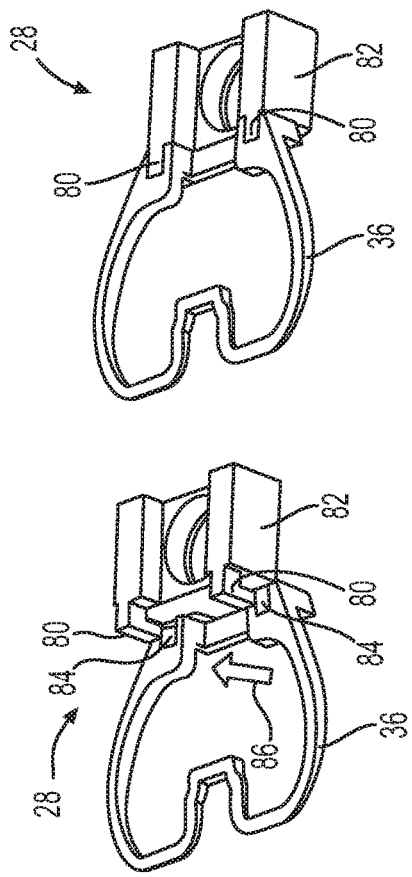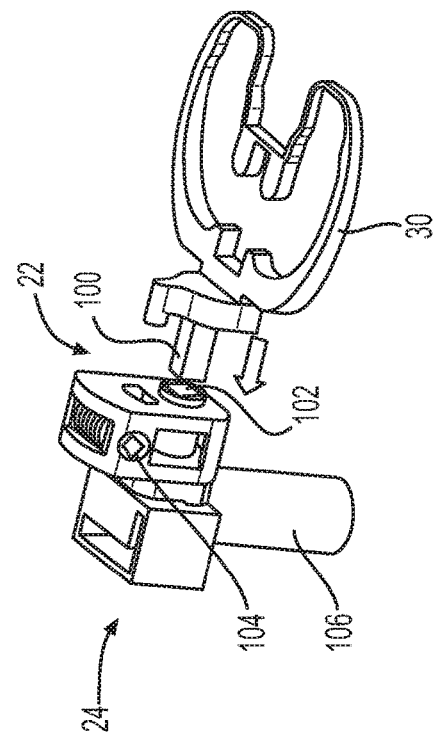
FIG. 10A  FIG. 10B  FIG. 11
FIG. 12A  FIG. 12B

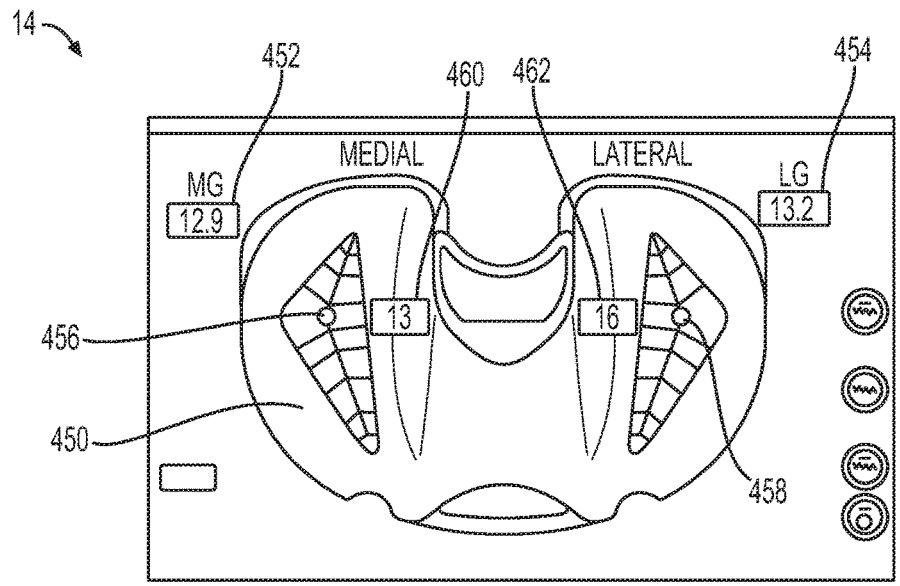
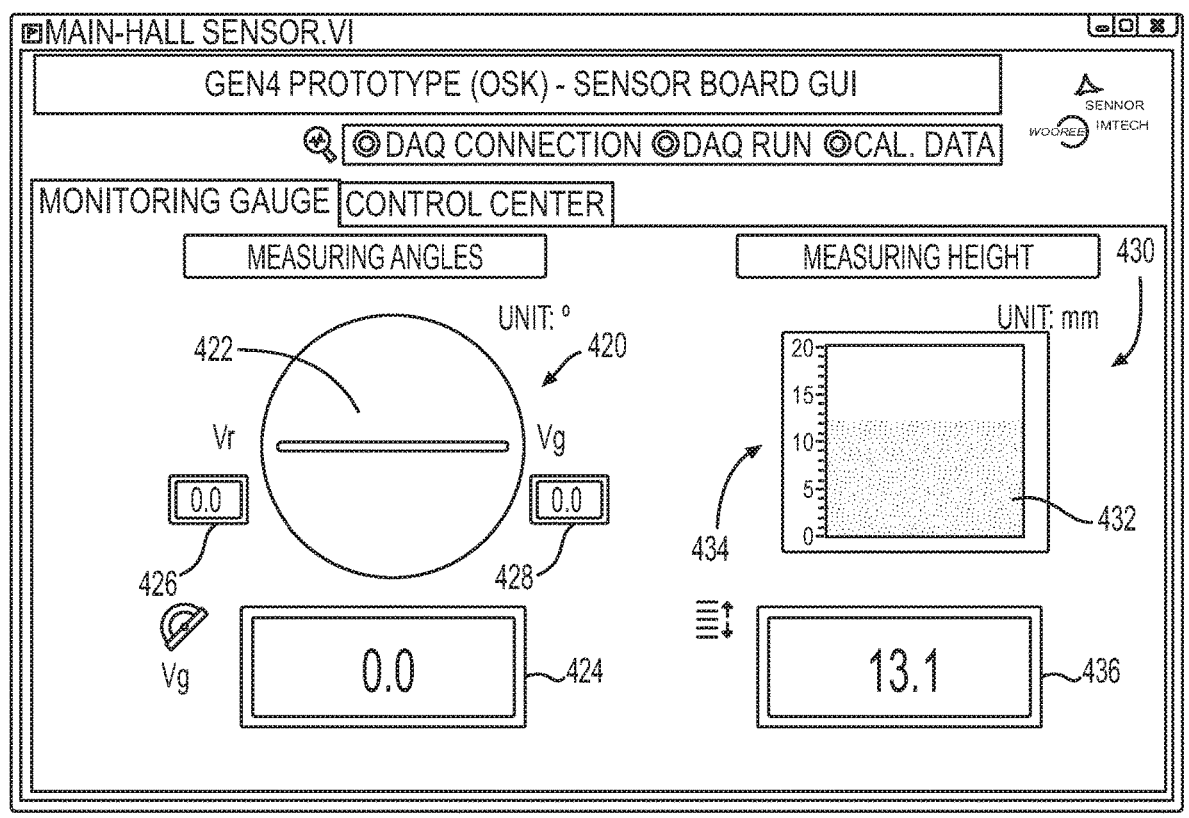
FIG. 33

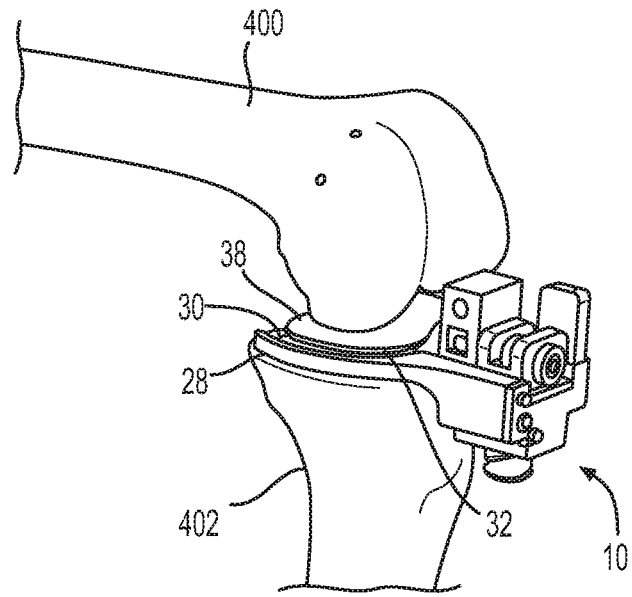
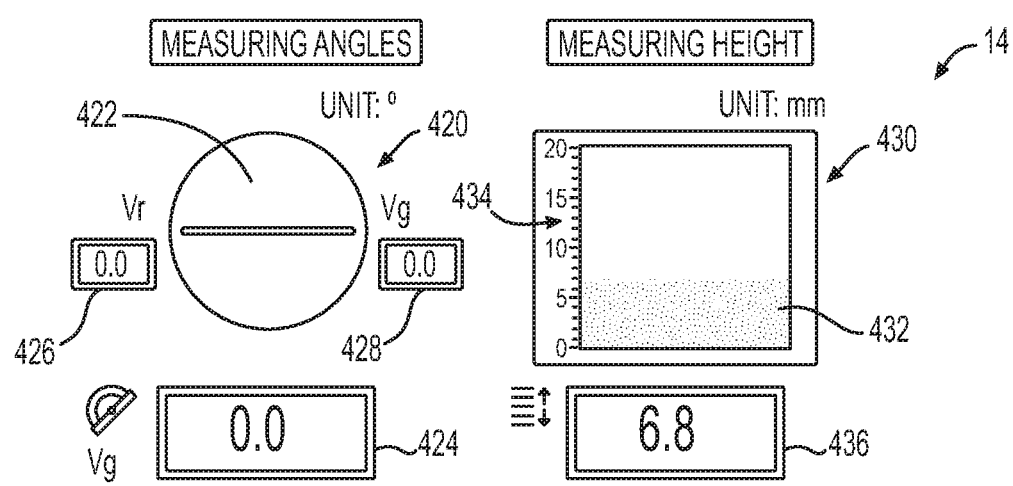
FIG. 36

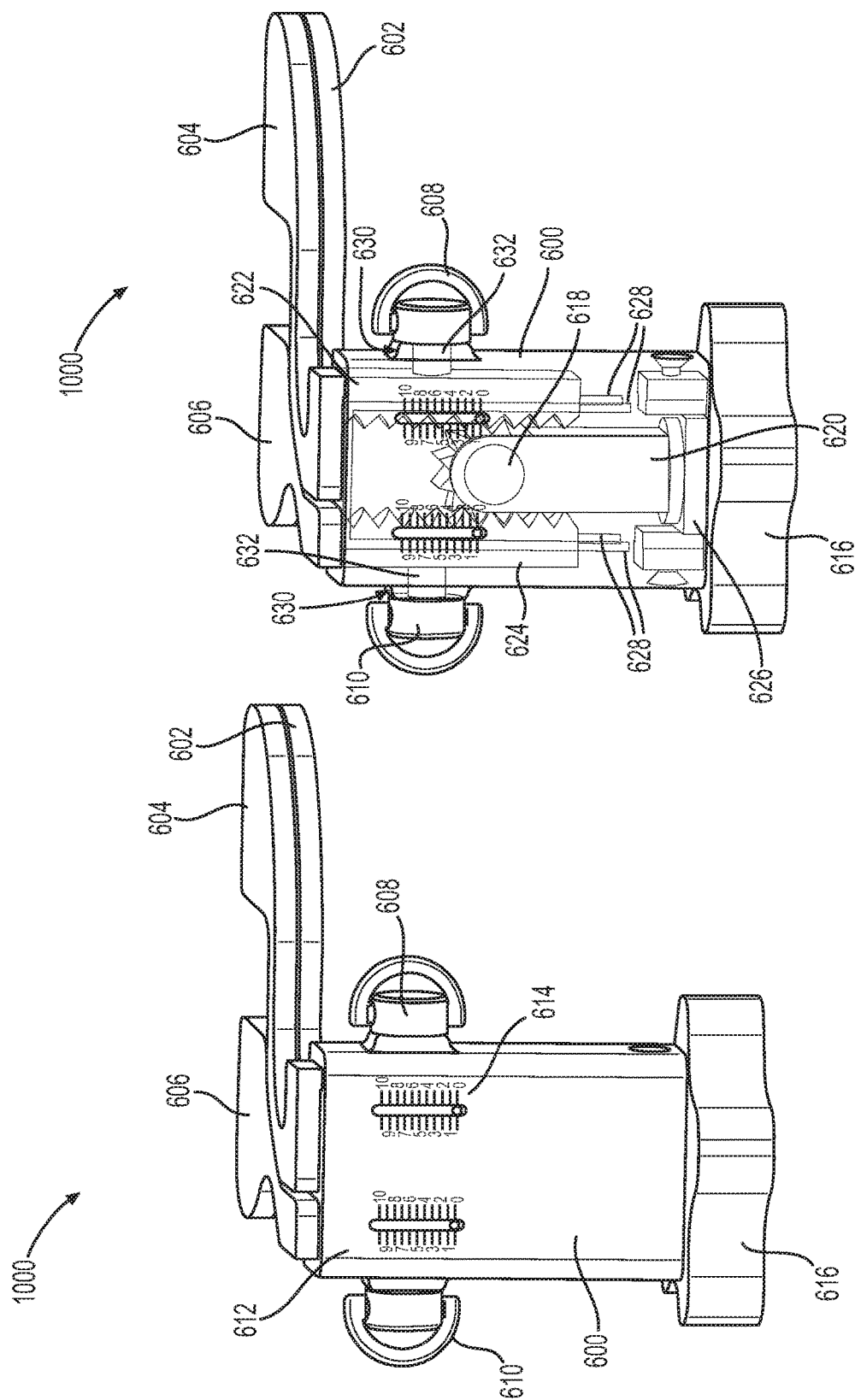

SURGICAL APPARATUS TO SUPPORT INSTALLATION OF A PROSTHETIC COMPONENT WITH REDUCED ALIGNMENT ERROR

FIELD

The present disclosure relates generally to orthopedic medical devices, and more specifically to devices that generate quantitative measurement data in real-time.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, prosthetic orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

FIG. 10A illustrates the frame and a frame retaining support structure in accordance with an example embodiment;

FIG. 10B illustrates the frame coupled to the frame retaining support structure in accordance with an example embodiment;

FIG. 11 illustrates different frame sizes in accordance with an example embodiment;

FIG. 12A illustrates the moving support structure disengaged from the M-L tilt mechanism in accordance with an example embodiment;

FIG. 12B illustrates the moving support structure coupled to M-L tilt mechanism in accordance with an example embodiment;

FIG. 33 illustrates a step of monitoring equalization of the femur on the display in accordance of an example embodiment;

FIG. 36 illustrates a step of reducing the distraction distance of the distractor and placing the leg in flexion in accordance with an example embodiment;

FIG. 44 is an illustration of an alternate embodiment of a distractor in accordance with an example embodiment;

FIG. 45 is an illustration of the alternate embodiment of the distractor with a transparent housing to illustrate components therein in accordance with an example embodiment;

DETAILED DESCRIPTION

Figure 1:
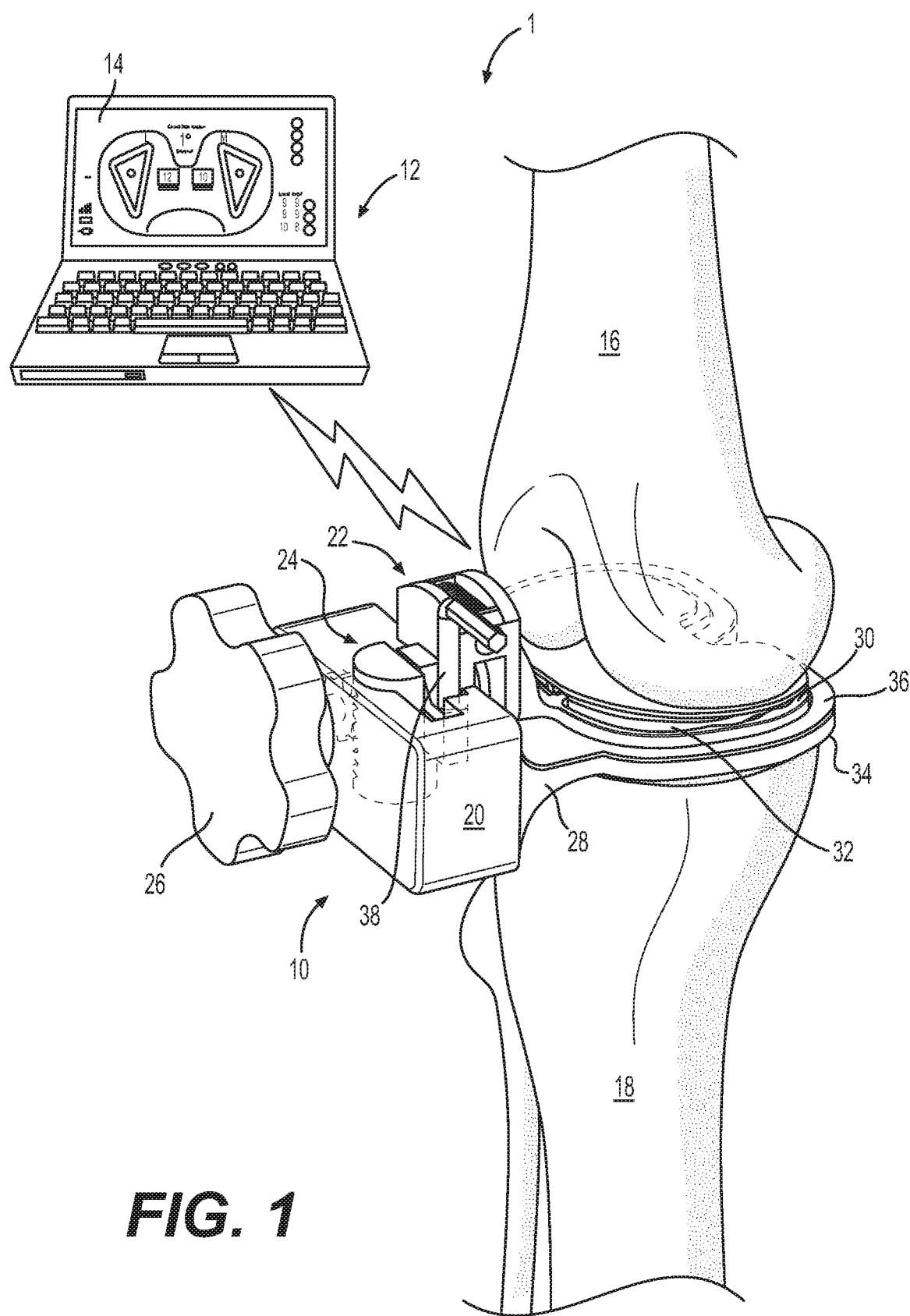
FIG. 1 is an illustration of an orthopedic measurement system generating quantitative measurement data to support installation of a prosthetic component in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the surgical apparatus are illustrative only and does not limit use for other parts of a body. The surgical apparatus can be used to measure, distract, align, cut, and support installation of prosthetic components to the musculoskeletal system. The surgical apparatus can be used on the knee, hip, ankle, spine, shoulder, hand, wrist, foot, fingers, toes, and other areas of the musculoskeletal system. In general, the principles disclosed herein are meant to be adapted for use in other locations of the musculoskeletal system.

FIG. 1 is an illustration of an orthopedic measurement system 1 generating quantitative measurement data to support installation of a prosthetic component in accordance with an example embodiment. Orthopedic measurement system 1 comprises a distractor 10, a module 32, and a computer 12. Distractor 10 can also be called a surgical apparatus, device, or tool. Distractor 10 is not limited to distraction but can perform other functions such as alignment, bone cuts, and parameter measurement to name but a few. Distractor 10 includes at least one sensor configured to generate quantitative measurement data. Similarly, module 32 includes at least one sensor configured to generate quantitative measurement data. Distractor 10 and module 32 each includes electronic circuitry configured to control a measurement process and transmit measurement data to computer 12. Computer 12 includes a display 14 configured to display the quantitative measurement data received from distractor 10 and module 32, analyze the measurement data, provide visual, haptic, or audible feedback related to the measurement data, and provide a workflow in support of an optimal installation based on the measurement data. In one embodiment, a distraction distance of distractor 10 and an M-L tilt angle of moving support structure 30 is measured and displayed on display 14 of computer 12.

Distractor 10 comprises a housing 20, distraction mechanism 24, medial-lateral (M-L) tilt mechanism 22, a fixed position support structure 28, and a moving support structure 30. In one embodiment, M-L tilt mechanism 22 couples between distraction mechanism 24 and fixed position support structure 28. Housing 20 partially houses distraction mechanism 24. A knob 26 or handle couples to distraction mechanism 24 to allow a user to increase or decrease a distraction distance of distractor 10. Housing 20 retains distraction mechanism 24 and supports movement of distraction mechanism 24 in a predetermined direction relative to fixed position support structure 28. In the example embodiment, fixed position support structure 28 couples to housing 20 and distraction mechanism 28 and moves perpendicular to a bottom surface 34 of fixed support structure 28. Moving support structure 30 couples to M-L tilt mechanism 22. Distraction mechanism 24 couples to M-L tilt mechanism 22 and is configured to raise or lower M-L tilt mechanism 22 and moving support structure 30 relative to fixed support structure 28. A distraction mechanism lock 38 is configured to lock distraction mechanism 24 from moving thereby holding a distance between moving support structure 30 and fixed support structure 28 constant.

M-L tilt mechanism 22 is configured to medially or laterally tilt moving support structure 30. A key or knob couples to M-L tilt mechanism 22 to change the M-L tilt. M-L tilt mechanism 22 can be disengaged from moving support structure 30 such that moving support structure 30 can freely tilt medially or laterally depending on how moving support structure 30 is loaded. Module 32 couples to and is supported by moving support structure 30. In one embodiment, module 32 couples to a major surface of moving support structure 30. A cover couples to module 32. The cover is removable and is an interface to the distal end of femur 16.

As shown in FIG. 1 the distraction distance of distractor 10 is at a minimum height. In the example, the proximal end of tibia 18 has a prepared surface. The prepared surface can be a planar surface and can also have a predetermined anterior-posterior (A-P) slope. In general, the word predetermined used herein above and below corresponds to a user selected value. The use of the word predetermined does not imply a specific value or range. A minimum distraction distance of distractor 10 occurs when surface 34 of fixed support structure 28 and a bottom surface of moving support structure 30 couples to the prepared surface of the proximal end of tibia 18. The distraction distance is the distance between the distal end of femur 16 and a proximal end of tibia 18 under distraction. Note that the cover couples to the condyles of femur 16 and fixed support structure 28 couples to the prepared surface of the proximal end of tibia 18. The distance between the cover and the fixed support structure corresponds to the distraction distance. In one embodiment, fixed support structure 28 comprises a frame 36. Frame 36 has an opening for receiving moving support structure 30 thereby allowing the bottom surface of moving support structure 30 to couple to the prepared bone surface of tibia 18.

Figure 2:
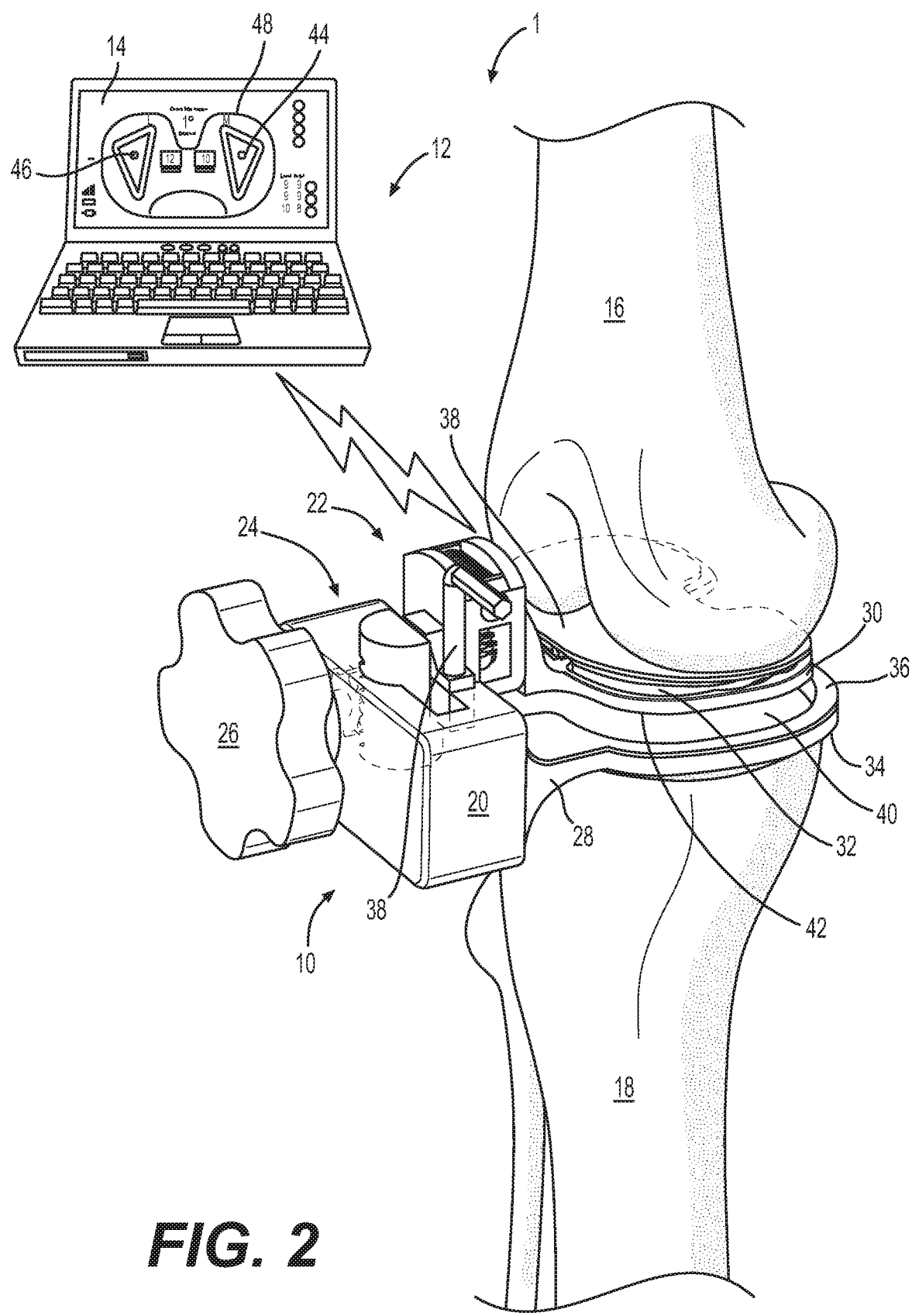
FIG. 2 is an illustration of the orthopedic measurement system distracting a knee joint of a leg in accordance with an example embodiment.

FIG. 2 is an illustration of orthopedic measurement system 1 distracting a knee joint of a leg in accordance with an example embodiment. As shown, the leg is in extension. Surface 34 of fixed support structure 28 couples to prepared surface 40 of the proximal end of tibia 18. Knob 26 couples to distraction mechanism 24. Rotating knob 26 increases or decreases separation between moving support structure 30 and fixed support structure 28. In the example, knob 26 is rotated to increase the distraction distance such that a bottom surface 42 of moving support structure 30 does not touch prepared bone surface 40. Module 32 and cover 38 are supported by moving support structure 30. Cover 38 couples to the condyles of the distal end of femur 16. Thus, the distraction distance includes the thickness of module 32 and cover 38 and is measured from the distal end of femur 16 to the prepared surface of tibia 18.

Distractor 10 includes a distance sensor on distractor 10 configured to measure the distraction distance. In one embodiment, the distance sensor couples to distraction mechanism 24. Similarly, distractor 10 includes an angle sensor configured to measure the M-L tilt angle of moving support structure 30. In one embodiment, the angle sensor couples to the M-L tilt mechanism 22. Distractor 10 includes electronic circuitry coupled to the distance sensor and the angle sensor. The electronic circuitry of distractor 10 controls a measurement process and transmits measurement data to computer 12. The measurement data can comprise distraction distance data and M-L tilt data from the distance sensor and the angle sensor. The distraction distance data and M-L tilt data can be displayed on display 14 in real-time. Alternatively, distractor 10 can have a mechanical distance gauge and a M-L tilt gauge on distractor 10.

Module 32 also includes electronic circuitry and one or more sensors. In one embodiment, module 32 includes a plurality of load sensors configured to measure loading applied to the cover 38. The load sensors are configured to measure load magnitudes at predetermined locations on cover 38. The electronic circuitry of module 32 is configured to control a load measurement process and transmit load data. Load data is transmitted from module 32 to computer 12. Computer 12 can process the load data from the plurality of load sensors (at predetermined locations) and calculate a load magnitude and a position of load where a condyle of femur 16 couples to cover 38. Computer 12 can provide visualization of the data to aid a surgeon in rapidly absorbing the quantitative measurement data. For example, a surface 48 of cover 38 or the surface of module 32 can be shown on display 14 of computer 12. Contact points 44 and 46 can indicate where each condyle couples to cover 38. The contact points 44 and 46 can move in real-time if a change occurs that results in a parameter change that affects the contact points. For example, performing soft tissue tensioning which changes loading applied by a medial condyle or a lateral condyle of femur 16 to distractor 10 can result in movement of contact points 44 and 46. The load magnitude at the point of contact can also be displayed. Thus, the surgeon can receive the information as the surgical procedure is being performed with little or no time penalty but greatly increased knowledge on the installation. It should be noted that module 32 is configured to be removed from moving support structure 30. This allows module 32 to be used in another piece of equipment later in the surgery to take further measurements, make adjustments, or verify that the final installation numbers are similar to that generated when preparing bone surfaces for prosthetic component installation. Similarly, cover 38 can be removed from module 32. Cover 38 can be substituted for other covers designed to interface with a different component. For example, cover 38 is configured to interface with the natural condyles of femur 16. A different cover can be used to interface with a prosthetic femoral component coupled to femur 16 later in the surgery to take further measurements or verify the previous quantitative measurement data.

Figure 3:
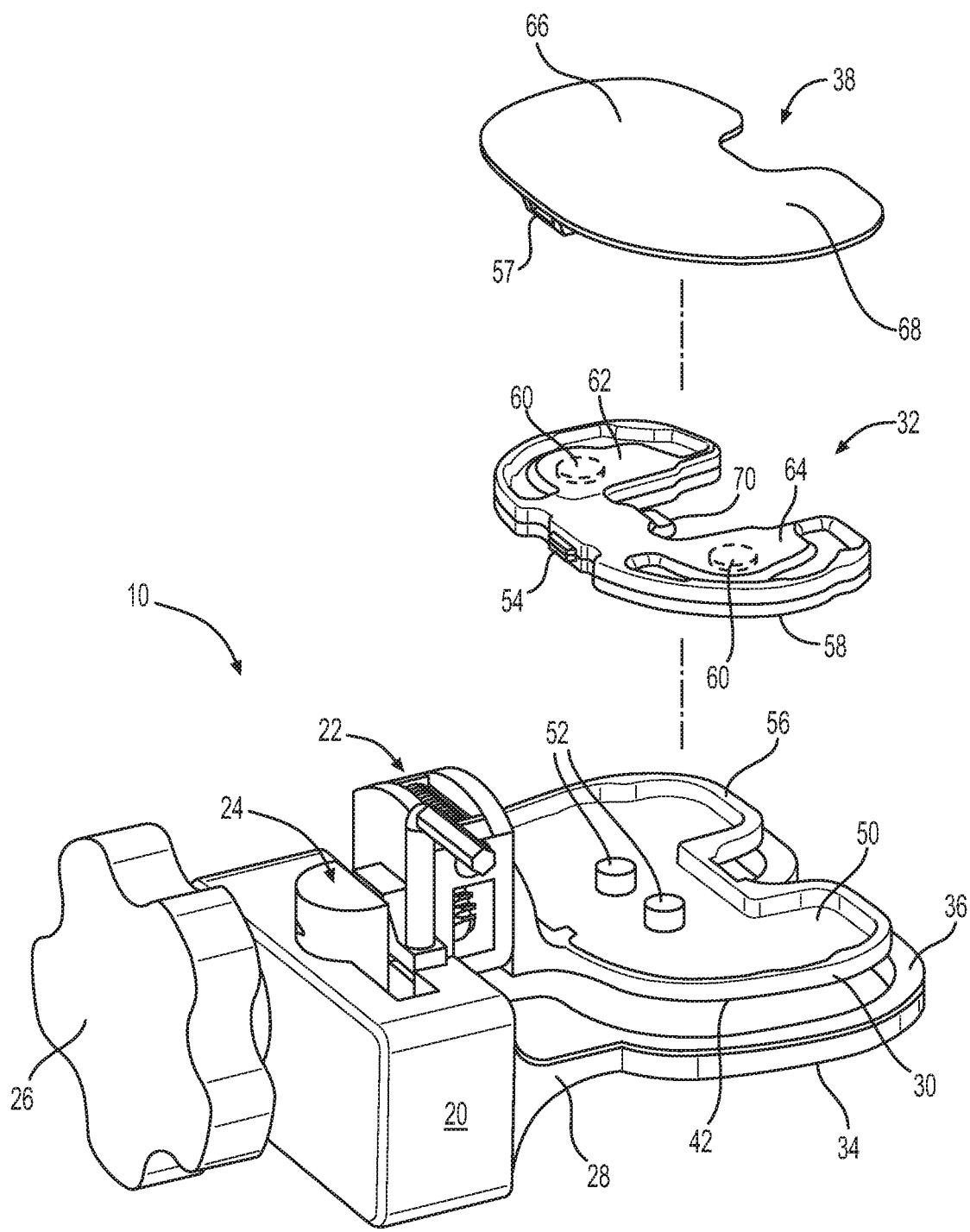
FIG. 3 illustrates the cover, the module, and the distractor in accordance with an example embodiment.

FIG. 3 illustrates cover 38, module 32, and distractor 10 in accordance with an example embodiment. Moving support structure 30 is shown separated from frame 36 of fixed support structure 28. Note that moving support structure 30 fits within an opening in frame 36 of fixed support structure 28 if the distraction distance is reduced by distraction mechanism 24. In one embodiment, moving support structure 30 has a major surface 50 configured to support module 32 when loaded by the knee joint. A surface 58 of module 32 couples to major surface 50 of moving support structure 30. In the example, module 32 comprises a medial side and a lateral side respectively configured to couple to a medial condyle and a lateral condyle of a knee joint. Major surface 50 of moving support structure 30 includes at least one alignment feature to retain and align module 32. For example, posts 52 extend from major surface 50 of moving support structure 30. Posts 52 are received within corresponding openings in module 32 when coupling a bottom surface 58 of module 32 to major surface 50 of moving support structure 30. Moving support structure 30 can further comprise a wall 56 or walls that align and retains module 32 to moving support structure 30. Posts 52 and wall 56 prevent lateral forces from detaching module 32 from moving support structure 30 under knee joint loading. Module 32 can be removed by lifting module 32 vertically from surface 50 of moving support structure 30. Module 32 is made to be removable so it can be placed in a prosthetic component such as an insert to make measurements later in the surgical installation of the knee joint.

Module 32 has electronic circuitry configured to control the measurement process and transmit the measurement data. The electronic circuitry couples to one or more sensors for measuring parameters. In the example, a plurality of load sensors underlies the medial side and the lateral side of module 32. This supports measurement of the load magnitude and the position of load due to the medial condyle and the lateral condyle of a femur coupled to cover 38. Module 32 is hermetically sealed and includes a power source such as a battery, super capacitor, inductor, or other structure that can operate module 32 during a surgical procedure. In one embodiment, batteries 60 are used to power the electronic circuitry in module 32. Module 32 further includes retaining structures 54 and 70 extending from a periphery. Retaining structures 54 and 70 are configured to align and retain cover 38 to module 32. In the example, cover 38 slidably engages to module 32. In one embodiment, retaining feature 70 fits into an opening of retaining feature 57 on cover 38 as cover 38 slides across module 32. Retaining feature 57 can flexed and includes an opening. A force can be applied to cover 38 to flex retaining feature 57 of cover 38 over retaining feature 54 of module 32. Retaining feature 54 of module 32 couples through the opening in retaining feature 57 to retain cover 38 to module 32. Conversely, cover 38 can be removed by flexing retaining feature 57 such that retaining feature 54 of module 32 no longer extends through the opening in retaining feature 57. Cover 38 can then be lifted to separate cover 38 from module 32. Cover 38 can then be moved to disengage retaining feature 70 from the opening of the corresponding retaining feature of cover 38 (that is not shown) thereby completely separating cover 38 from module 32.

A surface 62 and a surface 64 of module 32 is configured to couple to corresponding interior surfaces of cover 38. The plurality of load sensors underlie and couple to surface 62 and surface 64 of module 32. The plurality of load sensors are configured to couple to predetermined locations of a surface 66 and a surface 68 of cover 38. The plurality of load sensors measures loading applied by condyles of the femur to surfaces 66 and 68 of cover 38. The load data from the plurality of load sensors is used to determine a load magnitude and position of load of each condyle to surfaces 62 and 64 in real-time thereby allowing adjustments in-situ.

Figure 4:
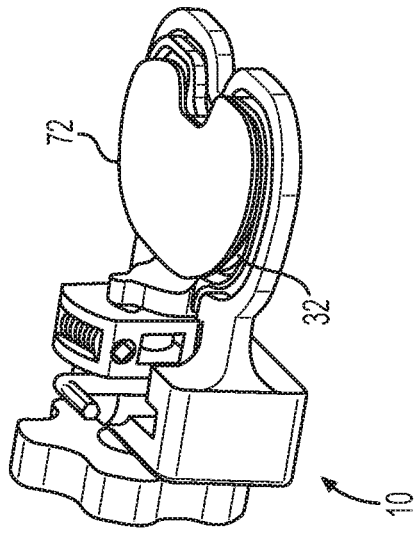
FIG. 4 illustrates a cover on the module configured having an anterior-posterior (A-P) slope of zero in accordance with an example embodiment.

FIG. 4 illustrates a cover 72 on module 32 configured having an anterior-posterior (A-P) slope of zero in accordance with an example embodiment. Cover 72 couples to module 32. Cover 72 is configured to couple to the natural condyles of a femur. In one embodiment, cover 72 is used prior to installation of the femoral prosthetic component and in conjunction with distractor 10 to support making one or more bone cuts to the distal end of a femur for receiving the femoral prosthetic component. Module 32 is configured to measure one or more parameters and transmit measurement data to a computer for further processing. In the example, disclosed above, module 32 measures loading applied by condyles of a femur on a medial and a lateral side of cover 72.

In one embodiment, a plurality of covers are provided with module 32. The covers can comprise a polymer or metal material. The covers can be molded to lower cost of manufacture. In one embodiment, the plurality of covers provided with module 32 have different anterior-posterior (A-P) slopes. The covers having different A-P slopes are used to change the biomechanics of the knee joint thereby affecting post-operative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 72 has an anterior-posterior slope of zero degrees. Thus, cover 72 does not add A-P slope for assessment.

Figure 5:
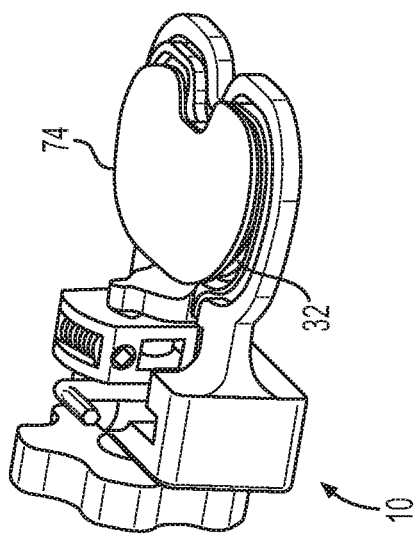
FIG. 5 illustrates a cover on the module configured having an anterior-posterior (A-P) slope of 2 degrees in accordance with an example embodiment.

FIG. 5 illustrates a cover 74 on the module configured having an anterior-posterior (A-P) slope of 2 degrees in accordance with an example embodiment. Cover 74 couples to module 32. Cover 74 is configured to couple to the natural condyles of a femur. Thus, cover 74 is used prior to installation of the femoral prosthetic component and in conjunction with distractor 10. Module 32 is configured to measure one or more parameters and transmit measurement data to a computer for further processing. In the example, module 32 measures loading applied by condyles of a femur on a medial and a lateral side of cover 74.

In general, a plurality of covers such as cover 74 and cover 72 of FIG. 4 are provided with module 32. The covers having different A-P slopes are used to change the biomechanics of the knee joint thereby affecting postoperative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 74 has an anterior-posterior slope of +2 degrees for assessing the knee joint with added slope.

Figure 6:
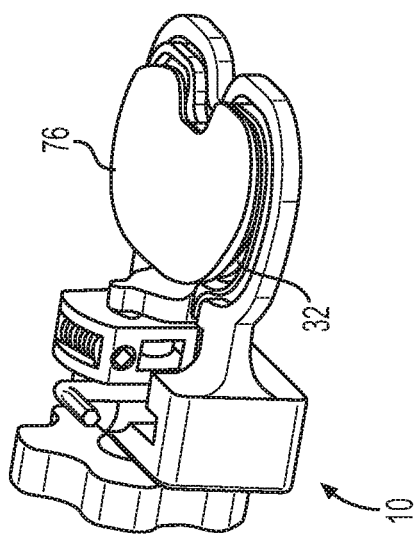
FIG. 6 illustrates a cover on the module configured having an anterior-posterior (A-P) slope of 4 degrees in accordance with an example embodiment.

FIG. 6 illustrates a cover 76 on the module configured having an anterior-posterior (A-P) slope of 4 degrees in accordance with an example embodiment. Cover 76 couples to module 32. Cover 76 is configured to couple to the natural condyles of a femur. Thus, cover 76 is used prior to installation of the femoral prosthetic component and in conjunction with distractor 10. Module 32 is configured to measure one or more parameters and transmit measurement data to a computer for further processing. In the example, module 32 measures loading applied by condyles of a femur on a medial and a lateral side of cover 76.

In general, a plurality of covers such as cover 76, cover 74 of FIG. 5, and cover 72 of FIG. 4 are provided with module 32. The covers having different A-P slopes are used to change the biomechanics of the knee joint thereby affecting postoperative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 76 has an anterior-posterior slope of +4 degrees for assessing the knee joint with added slope. FIGS. 4, 5, and 6 are examples and the number of covers and A-P slopes can be more or less than shown.

Figure 7:
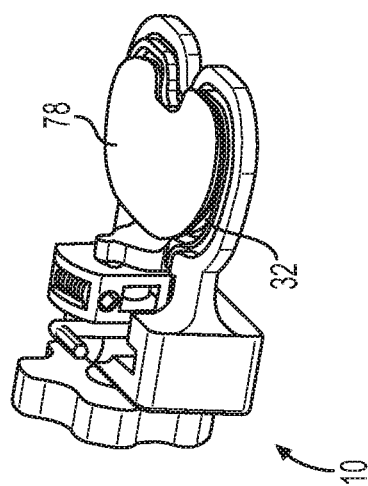
FIG. 7 illustrates a cover on the module configured to interface with natural condyles of the femur in accordance with an example embodiment.

FIG. 7 illustrates a cover 78 on module 32 configured to interface with natural condyles of a femur in accordance with an example embodiment. In one embodiment, distractor 10 is inserted in a knee joint with the proximal end of a tibia having a prepared bone surface and the distal end of a femur in a natural state. Natural condyles of the femur couple to cover 78. Cover 78 will support leg movement over a range of motion when the knee joint is distracted. In the example, module 32 measures loading applied by condyles of a femur on a medial and a lateral side of cover 78. A plurality of covers identical to cover 78 can be provided each having different A-P slopes to change the kinematics of the knee joint. Also, the plurality of covers can comprise different sizes for different knee sizes. For example, the covers can comprise small, medium, and large sizes that accommodate a large statistical sample of the population requiring knee joint replacement.

Figure 8:
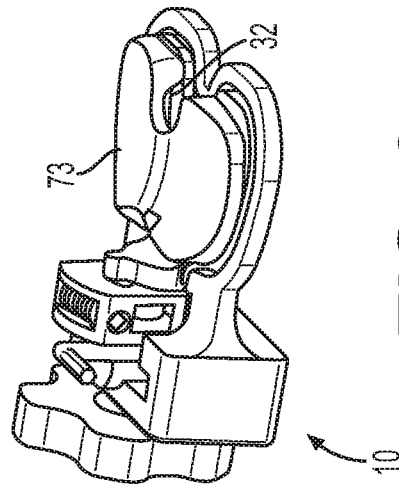
FIG. 8 illustrates a cover having a support structure on the module configured to interface with a femoral prosthetic component in accordance with an example embodiment.

FIG. 8 illustrates a cover 73 on module 32 configured to interface with a femoral prosthetic component coupled to a femur in accordance with an example embodiment. In one embodiment, distractor 10 is inserted in a knee joint with the proximal end of a tibia having a prepared bone surface and the distal end of fitted with a femoral prosthetic component. Cover 73 is configured to interface with the condyles of the femoral prosthetic component. In one embodiment, a surface of cover 73 has a contour to support leg movement under load with the condyles of the femoral prosthetic component coupled to the surface. Cover 73 supports all ligaments in place to stabilize the knee joint.

Cover 73 will support leg movement over a range of motion when the knee joint is distracted. In the example, module 32 measures loading applied on a medial side and a lateral side by the condyles of the femoral prosthetic component to cover 73. A plurality of covers identical to cover 73 can be provided each having different A-P slopes to change the kinematics of the knee joint. Also, the plurality of covers can comprise different sizes for different knee sizes having different femoral prosthetic component sizes. For example, the covers can comprise small, medium, and large sizes that accommodate a large statistical sample of the population requiring knee joint replacement.

Figure 9:
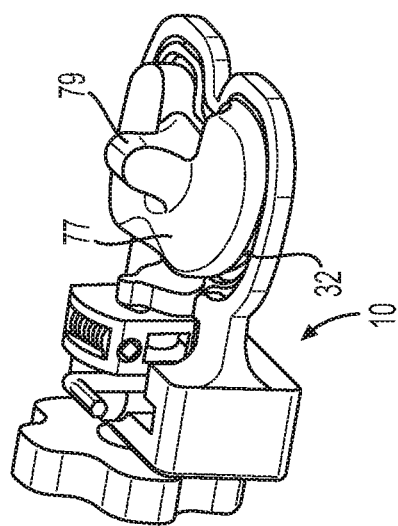
FIG. 9 illustrates a cover on the module configured to interface with a femoral prosthetic component having a support structure coupled to a femur in accordance with an example embodiment.

FIG. 9 illustrates a cover 77 on module 32 configured to interface with a femoral prosthetic component coupled to a femur in accordance with an example embodiment. In one embodiment, distractor 10 is inserted in a knee joint with the proximal end of a tibia having a prepared bone surface and the distal end fitted with a femoral prosthetic component. Cover 77 includes a support structure 79 that provides support when a ligament is removed from the knee joint. In one embodiment, support structure 79 is coupled to covers disclosed herein above to form cover 77. Alternatively, cover 77 can be provided having integral support structure 79. Cover 77 is configured to interface with the condyles of the femoral prosthetic component. A surface of cover 77 has a contour to support leg movement under load with the condyles of the femoral prosthetic component coupled to the surface.

Cover 77 will support leg movement over a range of motion when the knee joint is distracted and a ligament removed. In the example, module 32 measures loading applied on a medial side and a lateral side by the condyles of the femoral prosthetic component to cover 77. A plurality of covers identical to cover 77 can be provided each having different A-P slopes to change the kinematics of the knee joint. Support structure 79 can couple to each of the plurality of covers. Also, the plurality of covers can comprise different sizes for different knee sizes having different femoral prosthetic component sizes. For example, the covers can comprise small, medium, and large sizes that accommodate a large statistical sample of the population requiring knee joint replacement.

FIG. 10A illustrates a frame 36 and a frame retaining support structure 82 in accordance with an example embodiment. In one embodiment, fixed support structure 28 of FIG. 1 comprises retaining support structure 82 and frame 36. Frame 36 is configured to be removable from frame retaining support structure 82. Frame retaining support structure 82 allows for different frame sizes and different frame shapes to couple to distractor 10. Alternatively, frame 36 and frame retaining support structure 82 could be formed as a single structure. In one embodiment, frame retaining support structure 82 is formed as part of housing 20 of FIG. 1. For example, a portion of housing 20 and frame retaining support structure 82 can be made as a single structure or formed in a mold thereby having a fixed geometric relationship between frame retaining support structure 82 and a distraction mechanism aligned and retained by housing 20. Housing 20 can be formed from a polymer material, metal, or metal alloy that supports loading applied by a knee joint when distracted. Frame retaining support structure 82 includes retaining structures 80 configured to retain and align frame 36 to frame retaining support structure 82. Frame 36 is coupled to frame retaining support structure 82 by pressing frame 36 into frame retaining support structure 82 as indicated by arrow 86. Frame 36 includes retaining structures 84 that interlock with retaining structures 80 of frame retaining support structure 82 such that frame 36 is rigid under loading of the knee joint and does not change a geometric relationship with frame retaining support structure 82 or housing 20 of FIG. 1. Conversely, frame 36 can be removed by applying a force in an opposite direction as arrow 86 to frame 36 to release frame 36 from frame retaining support structure 82. A larger or smaller frame 36 can replace frame 36 that better fits the bone structure of the patient.

FIG. 10B illustrates the frame 36 coupled to frame retaining support structure 82 in accordance with an example embodiment. Retaining structures 84 of frame 36 of FIG. 10A are shown interlocking with retaining structures 80 of frame retaining support structure 82. Frame 36 is held in a predetermined position relative to frame retaining support structure 82 and the housing of the distractor. In one embodiment, frame 36 and frame retaining support structure 82 are rigid and do not flex or torque under loading applied by the knee joint.

FIG. 11 illustrates different frame sizes in accordance with an example embodiment. Bone size varies across the population of patients requiring knee surgery. Different frame sizes are provided that support a majority of the total knee arthroplasty surgeries performed each year. A frame 90 is shown coupled to frame retaining support structure 82. A larger frame can be used if frame 90 is found to be too small for coupling to the prepared surface of a tibia. Frame 90 would then be removed from frame retaining support structure 82. A frame 92 can then be selected that is larger than frame 90 and installed onto frame retaining support structure 82. Thus, the distractor 10 of FIG. 1 supports removable frames and frames of different sizes to couple the distractor to the prepared surface of the tibia 18. The number of frame sizes provided can be more or less than shown in FIG. 11.

FIG. 12A illustrates moving support structure 30 disengaged from M-L tilt mechanism 22 in accordance with an example embodiment. M-L tilt mechanism 22 is shown coupling to a portion of distraction mechanism 24. Distraction mechanism 24 comprises a post 106 configured to raise or lower M-L tilt mechanism 22 and moving support structure 30 relative to the fixed support structure 28 of FIG. 1. A key or handle can be inserted into coupler 104 of M-L tilt mechanism 22. The key when rotated adjusts an M-L tilt angle of M-L tilt mechanism 22 when enabled. M-L tilt mechanism 20 further includes a coupler 102 that is configured to rotate as the key is rotated.

Moving support structure 30 includes a coupler 100 configured to couple to coupler 102 of M-L tilt mechanism 22. Coupler 100 is inserted into coupler 102 thereby retaining and aligning moving support structure 30 to M-L distraction mechanism 22. M-L tilt mechanism 22 can be disengaged from coupler 102 thereby allowing coupler 102 and moving support structure 30 to freely rotate. In one embodiment, coupler 100 has a square or rectangular shape that fits into a corresponding square or rectangular opening of coupler 102. Couplers 100 or 102 can be configured to have a temporary locking mechanism that retains moving support structure 30 to M-L tilt mechanism 22 while supporting removability. Similar to fixed support structure 28, 90, and 92 disclosed in FIGS. 10A, 10B and 11 that are also removable, a plurality of moving support structures can be provided of different sizes or styles. In general, two or more moving support structures are provided with distractor 10 of FIG. 1.

FIG. 12B illustrates moving support structure 30 coupled to M-L tilt mechanism 22 in accordance with an example embodiment. Moving support structure 30 as mentioned previously is removable from M-L tilt mechanism 22. This allows other moving support structures of different sizes or styles to be used with distractor 10 shown FIG. 1. A module having electronic circuitry and at least one sensor is placed on major surface 50 of moving support structure 30 to measure at least one parameter. A cover configured to interface with natural condyles of a femur or a cover configured to interface with a femoral prosthetic component couples to the module. Distraction mechanism 24 is configured to increase or decrease a distraction distance between moving support structure 30 and the fixed support structure 28 of FIG. 1. Distraction mechanism 24 raises or lowers both M-L tilt mechanism 22 and moving support structure 30. Moving support structure 30 is also configured to tilt medially or laterally when M-L tilt mechanism 22 is adjusted. In general, a plurality of moving support structures are provided. The moving support structures can comprise different sizes and different styles. The different moving support structures can correspond to the different frames disclosed in FIG. 11. The moving support structures can accommodate the wide diversity and variation of patient bone structure that is seen in an operating room.

Figure 13:
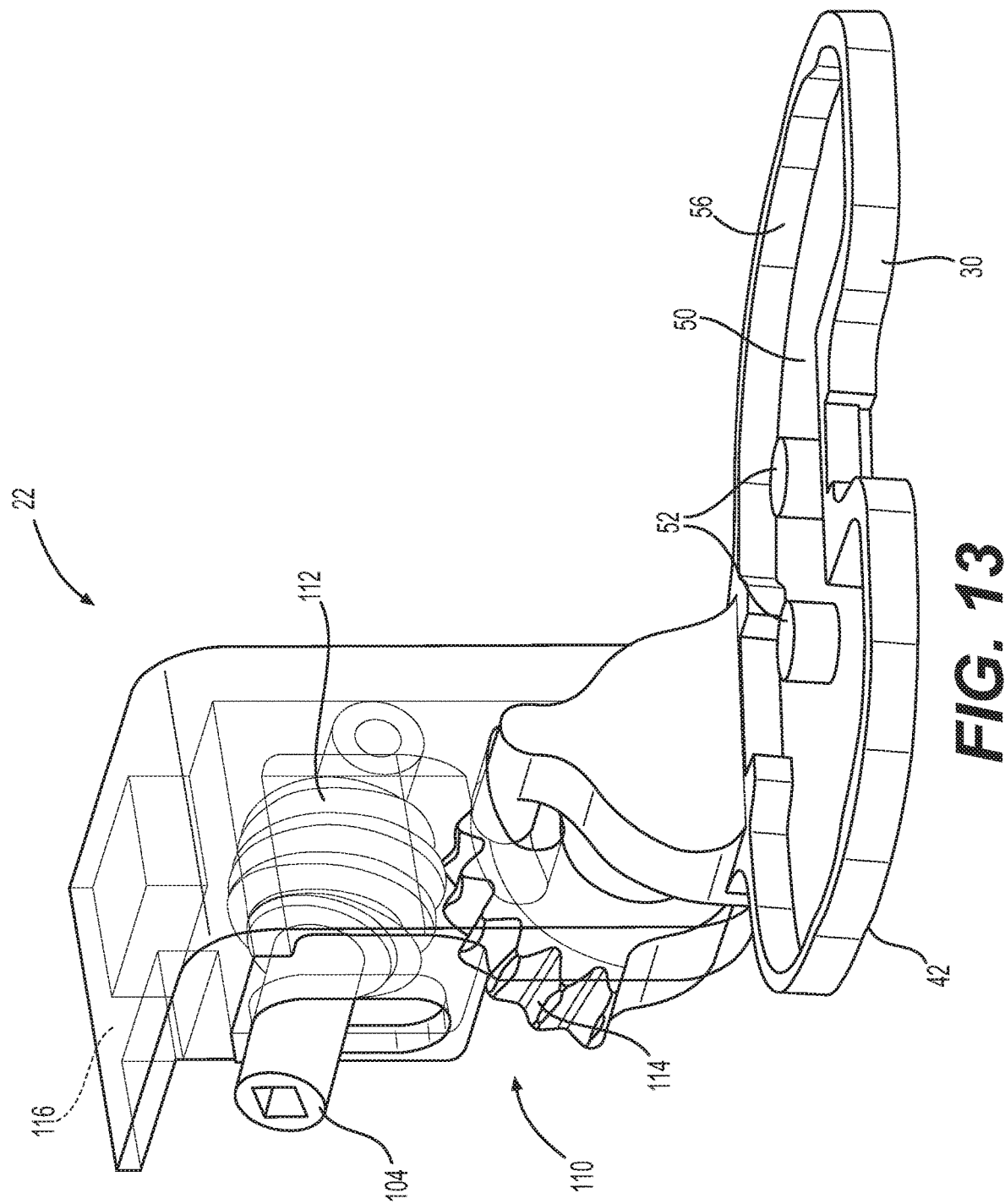
FIG. 13 is an illustration of the M-L tilt mechanism in accordance with an example embodiment.

FIG. 13 is an illustration of M-L tilt mechanism 22 in accordance with an example embodiment. In the example, M-L tilt mechanism 22 is a worm gear drive 110. Worm gear drive 110 comprises two or more gears of which at least one is a worm gear. As shown, worm gear drive 110 comprises a worm gear 112 and a gear 114. A housing 116 at least partially houses worm gear 112 and gear 114. Housing 116 retains, aligns, and supports rotation of worm gear 112 to gear 114. Coupler 104 couples to worm gear 112. In one embodiment, coupler 104 is a shaft of worm gear 112. Typically a key or handle couples to the opening in coupler 104 to allow a user to rotate worm gear 112.

Gear 114 couples to moving support structure 30. Housing 116 retains, aligns, and supports rotation of gear 114 when coupled to worm gear 112. As shown, M-L tilt mechanism 22 is decoupled from adjusting an M-L tilt angle of moving support structure 30. M-L tilt mechanism 22 is decoupled when the gear teeth of worm gear 112 are positioned such that the gear teeth of gear 114 do not couple to worm gear 112. Moving support structure 30 is free to tilt medially or laterally when M-L tilt mechanism 22 is decoupled and loaded by a knee joint. Gear 114 rotates as moving support structure 30 rotates and vice versa. The module 32 and cover 38 disclosed in FIG. 2 couple between the condyles of the femur and moving support structure 30. The module 32 is supported by major surface 50 of moving support structure 30. Module 32 is aligned and retained to moving support structure 30 by posts 52 and sidewall 56. The medial or lateral tilt of the knee joint corresponds to the balance of the knee joint and alignment of the leg.

In one embodiment, the teeth of worm gear 112 are coupled to the teeth of gear 112 to engage M-L tilt mechanism 22 after moving support structure 30 has been allowed to freely move to an unequalized M-L tilt angle. The teeth of worm gear 112 are configured to couple to gear 114 in a manner where they are self-locking. In other words, worm gear 112 and gear 114 hold the position of the moving support structure 30 at the unequalized M-L tilt angle when engaged. The key or handle is inserted into coupler 104 to rotate worm gear 112. In one embodiment, M-L tilt mechanism 22 is rotated an amount that equalizes the M-L tilt angle. This corresponds to a medial compartment being at an equal in height to a lateral compartment height. Worm gear drive 110 when rotated will change the medial or lateral tilt depending on the direction of rotation and maintains self-locking at an adjusted medial or lateral tilt. Quantitative measurement data from a sensor is used to determine when the M-L tilt angle is equalized. Typically, the loading on the medial and lateral compartments will be unequal. Soft tissue tensioning can be used to adjust the loading applied by the condyles of the femur to the cover of the module. Equalizing the M-L tilt angle reduces an offset of the femur to the mechanical axis of the leg.

Figure 14:
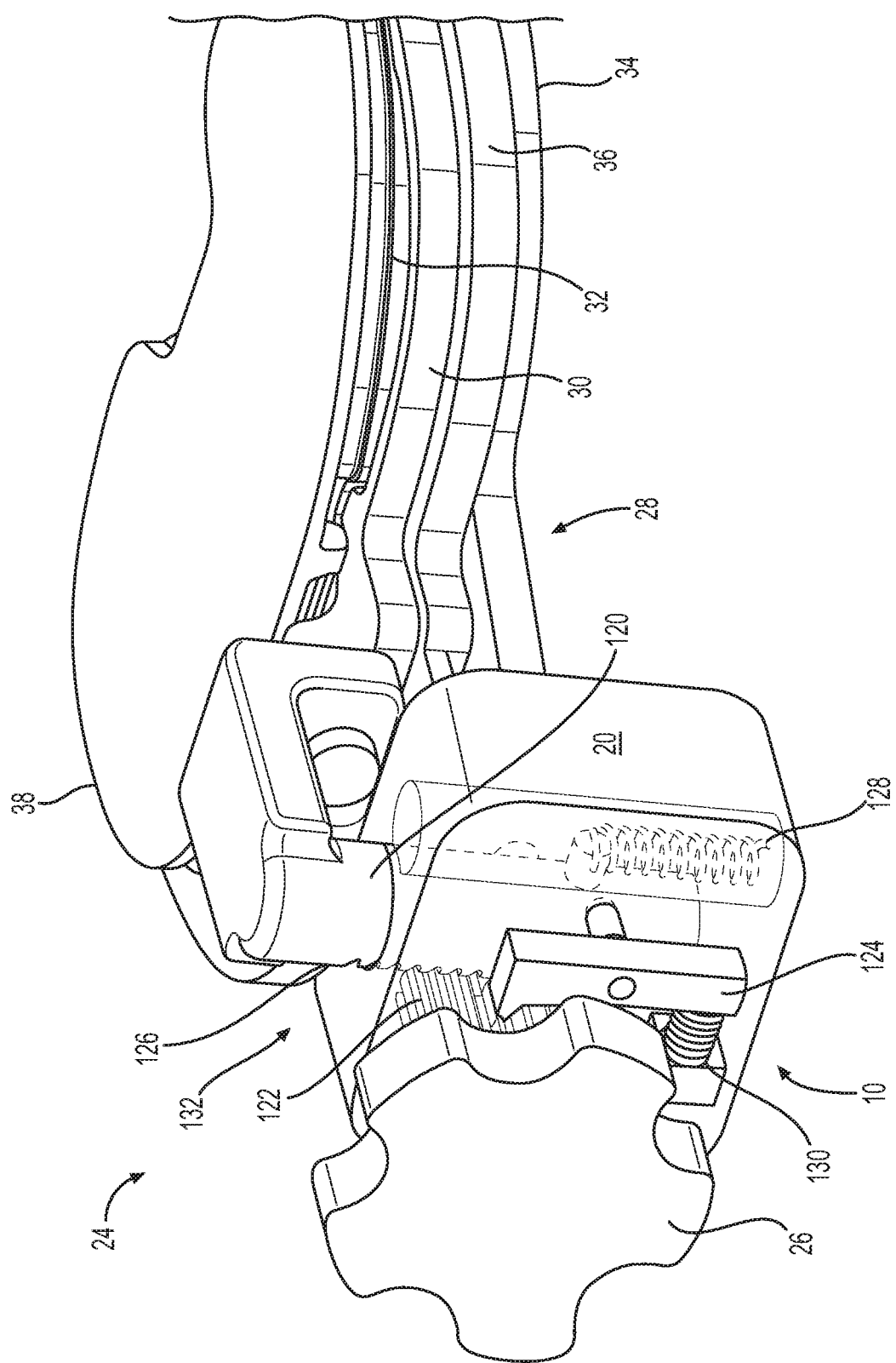
FIG. 14 is an illustration of the distraction mechanism in accordance with an example embodiment.

FIG. 14 is an illustration of distraction mechanism 24 in accordance with an example embodiment. In one embodiment, distraction mechanism 24 comprises a gear drive 132. Gear drive 132 can comprise two or more gears and is configured to increase or decrease separation between fixed support structure 28 and moving support structure 30 of distractor 10. Gear drive 132 comprises a post 120 and a gear 122. Post 120 extends outside housing 20 and is coupled to moving support structure 30. Housing 20 is configured to align, retain, and support movement of post 120 and gear 122. Housing 20 positions gear 122 adjacent to post 120 such that teeth of gear 122 engage with gear teeth 126 of post 120. Knob 26 couples to gear 122 to facilitate rotation. In one embodiment, housing 20 supports movement of post 120 perpendicular to a plane of fixed support structure 28.

Rotating knob 26 rotates gear 122 which in turn raises or lowers post 120 depending on the direction of rotation. A spring 128 can be coupled to post 120 and housing 20. Spring 128 can provide a spring resistance as post 120 is being raised from a minimum distraction distance. As mentioned previously, the minimum distraction distance corresponds to distractor 10 having support structure 30 within the opening of fixed support structure 28. In one embodiment, the minimum distraction distance occurs when both moving support structure 30 and fixed support structure 28 couples to a prepared surface of a tibia. In one embodiment, a minimum height for a medial compartment and a lateral compartment of a knee joint occurs when a bottom surface 34 of fixed support structure is co-planar with a bottom surface of moving support structure 30.

A distraction mechanism lock 124 is configured to prevent movement of gear drive 132. Distraction lock mechanism 124 is coupled to housing 20 and is configured to pivot. Distraction lock mechanism 124 is configured to be enabled and disabled. A spring 130 supports pivoting of distraction lock mechanism 124 in a locked position whereby a tooth of distraction lock mechanism 124 is configured to engage with gear 122 to prevent movement. Spring 128 supports retention of the tooth of distraction lock mechanism 124 in gear 122 by applying a force on post 120 that holds gear 122 against distraction lock mechanism 124 that prevents a user from rotating knob 26. Moving support structure 30 will maintain a distraction distance to fixed support structure 28 until distraction lock mechanism 124 is released or disabled.

Figure 15:
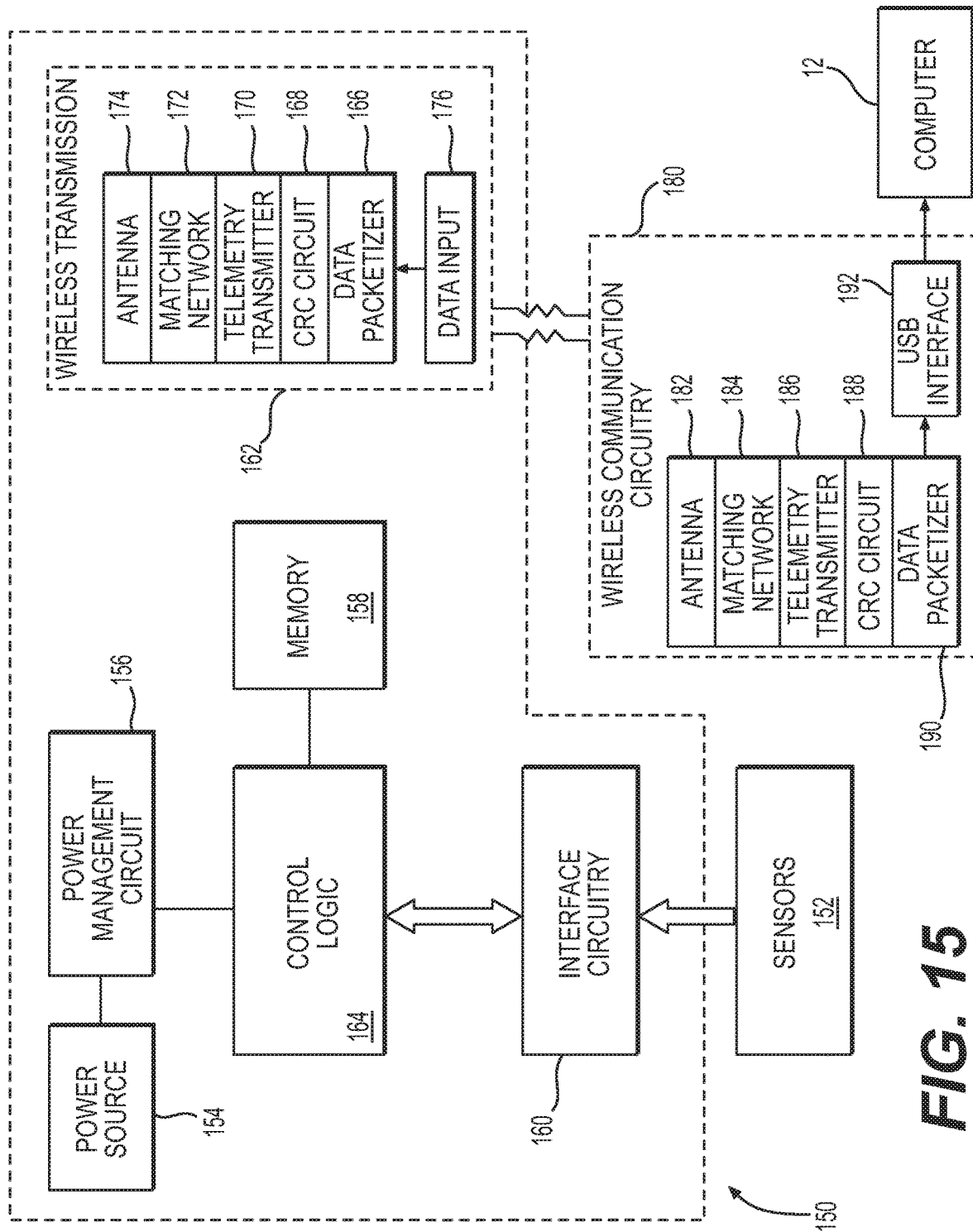
FIG. 15 is a block diagram of electronic circuitry in the distractor of FIG. 1 or the module of FIG. 1 in accordance with an example embodiment.

FIG. 15 is a block diagram of electronic circuitry 150 in distractor 10 of FIG. 1 or module 32 of FIG. 1 in accordance with an example embodiment. Components of FIG. 1 may be referred to herein in the discussion of electronic circuitry 150. Electronic circuitry 150 couples to sensors 152 in distractor 10 or module 32. Electronic circuitry 150 is configured to control a measurement process, receive measurement data from sensors 152 and transmit the measurement data to computer 12 of FIG. 1 for further analysis and feedback. Parameters are measured by sensors 152 coupled to electronic circuitry 150 in module 32 or distractor 10. Electronic circuitry 150 comprises a power management circuit 156, control logic 164, memory 158, and interface circuitry 160. A power source 154 couples to electronic circuitry 150 to power a measurement process. Electronic circuitry 150 further includes a transceiver 162 and an antenna 174 that can be positioned on or within, or engaged with, or attached or affixed to or within, a wide range of physical systems including, but not limited to instruments, equipment, devices, prosthetic components, or other physical systems for use on or in human bodies and configured for sensing and communicating parameters of interest in real time.

In general, electronic circuitry 150 is configured to provide two-way communication between distractor 10 or module 32 and computer 12. In one embodiment, distractor 10 provides quantitative measurement data related to a distraction distance, medial-lateral tilt, or anterior-posterior tilt of distractor 10. In one embodiment, module 32 provides quantitative measurement data related to load magnitude, position of load, position, tilt, balance, and alignment. Alternatively, distractor 10 can have mechanical gauges to provide measurement data local to the device. The measurement data from distractor 10 or module 32 can be used by computer 12 in a kinematic assessment to support installation of prosthetic components to ensure optimal loading, balance, and alignment that improves performance and reliability based on clinical evidence.

Power source 154 provides power to electronic circuitry 150 and sensors 152. The power source 154 can be temporary or permanent. In one embodiment, the power source can be rechargeable. Charging of the power source 154 can comprise wired energy transfer or short-distance wireless energy transfer. A charging power source to recharge power source 154 can include, but is not limited to, a battery or batteries, an alternating current power supply, a radio frequency receiver, an electromagnetic induction coil, a photoelectric cell or cells, a thermocouple or thermocouples, or a transducer energy transfer. Power source 154 has sufficient energy to operate electronic circuitry 150 in distractor 10 or module 32 for one or more surgeries with a single charge. Distractor 10 or module 32 can utilize power management technologies to minimize the power drain of power source 154 while in use and when it is idling. In one embodiment, distractor 10, module 32, or both can be a disposable device after a surgery is completed.

In one embodiment, power source 154 in distractor 10 or module 32 is a rechargeable battery. The rechargeable battery can be recharged by the methods disclosed herein above. Alternatively, power source 154 can be a super capacitor, an inductor, or other energy storage device. An external charging source can be coupled wirelessly to the rechargeable battery, capacitor, or inductive energy storage device through an electromagnetic induction coil by way of inductive charging. The charging operation can be controlled by power management circuit 156 within electronic circuitry 150. In one embodiment, power management circuit 156 supports operation of distractor 10 or module 32 during charging thereby allowing the surgery to continue if a low charge on power source 154 is detected. For example, power can be transferred to the battery, capacitive energy storage device, or inductive energy storage device by way of efficient step-up and step-down voltage conversion circuitry. This conserves operating power of circuit blocks at a minimum voltage level to support the required level of performance.

Power management circuit 156 is configured to operate under severe power constraints. In one embodiment, power management circuit 156 controls power up, power down, and minimizes power usage. The power management circuit 156 can also reduce power during operation of the system. The power management circuit 156 can turn off or reduce the power delivered to circuits that are not being used in a specific operation. Similarly, if the system is idle and not being used, the power management circuit 156 can put other unused circuitry in a sleep mode that awakens prior to the next measurement being made. Power management circuit 156 can include one or more voltage regulation circuits that provide a plurality of different stable voltages to electronic circuitry 150 and sensors 152 to minimize power dissipation.

In one configuration, a charging operation of power source 154 can further serve to communicate downlink data to electronic circuitry. For instance, downlink control data can be modulated onto the energy source signal and thereafter demodulated from an inductor in electronic circuitry 150. This can serve as a more efficient way for receiving downlink data instead of configuring an internal transceiver within electronic circuitry 150 for both uplink and downlink operation. As one example, downlink data can include updated control parameters that distractor 10 or module 32 uses when making a measurement, such as external positional information or for recalibration purposes. It can also be used to download a serial number or other identification data.

Control logic 164 controls a measurement process or sequence that engages the sensors, converts the measurement data into a useable format, and transmits the information. Control logic 164 can comprise digital circuitry, a microcontroller, a microprocessor, an ASIC (Application Specific Integrated Circuit), a DSP (Digital Signal Processing), a gate array implementation, a standard cell implementation, and other circuitry. Control logic 164 couples to memory 158. Memory 158 is configured to store measurement data, software routines, diagnostics/test routines, calibration data, calibration algorithms, workflows, and other information or programs. In one embodiment, one or more sensors may be continuously enabled and control logic 164 can be configured to receive the measurement data, store the measurement data in memory, or transmit the measurement data in real-time. Control logic 164 can include dedicated ports that couple to a sensor to continuously receive measurement data or receive at high sample rates measurement data. Alternatively, control logic 164 can select a sensor to be measured. For example, multiple sensors can be coupled to control logic 164 via a multiplexer. Control logic 164 controls which sensor is coupled through the multiplexer to receive measurement data. Multiplexed measurement data works well when the measurement data is not critical or can be sampled occasionally as needed. Control logic 164 can also select and receive measurement data from different sensors in a sequence. Control logic 164 can be configured to monitor the measurement data from a sensor but transmit measurement data only when a change occurs in the measurement data. Furthermore, control logic 164 can modify the measurement data prior to transmitting the measurement data to computer 12. For example, the measurement data can be corrected for non-linearity using calibration data.

Interface circuitry 160 couples between sensors 152 and control logic 164. Interface circuitry 160 supports conversion of a sensor output to a form that can be received by computer 12. Interface circuitry 160 comprises digital circuitry and analog circuitry. The analog circuitry can include multiplexers, amplifiers, buffers, comparators, filters, passive components, analog to digital converters, and digital to analog converters to name but a few. In one embodiment interface circuitry 160 uses one or more multiplexers to select a sensor for providing measurement data to control logic 164. Control logic 164 is configured to provide control signals that enable the multiplexer to select the sensor for measurement. The multiplexer can be enabled to deliver the measurement data to control logic 164, memory 158, or to be transmitted in real-time. Typically, at least one analog to digital conversion or digital to analog conversion of the measurement data occurs via the interface circuitry 160.

Sensors 152 couple through interface circuitry 160 to control logic 164. Alternatively, interface circuitry 160 can couple directly to circuitry for transmitting measurement data as it is measured. The physical parameter or parameters of interest measured by sensors 152 can include, but are not limited to, height, length, width, tilt/slope, position, orientation, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Often, a measured parameter is used in conjunction with another measured parameter to make a kinetic and qualitative assessment. In joint reconstruction, portions of the muscular-skeletal system can be prepared to receive prosthetic components. Preparation includes bone cuts or bone shaping to mate with one or more prosthesis. Parameters can be evaluated relative to orientation, alignment, direction, displacement, or position as well as movement, rotation, or acceleration along an axis or combination of axes by wireless sensing modules or devices positioned on or within a body, in an instrument, an appliance, a tool, equipment, prosthesis, or other physical system.

The sensors can directly or indirectly measure a parameter of interest. For example, a load sensor in module 32 of FIG. 1 can comprise a capacitor that has an elastic dielectric that can compress when a load is applied to the capacitor. This is an indirect form of sensing a parameter (load) where the capacitance of the capacitor varies with loading. The capacitive measurement data is sent to computer 12 of FIG. 1 for further processing. Computer 12 can include software and calibration data related to the elastic capacitors. The load measurement data can be converted from capacitance values to load measurements. The calibration data can be used to curve fit and compensate for non-linear output of a sensor over a range of operation. Furthermore, the individual sensor measurement can be combined to produce other measurement data by computer 12. In keeping with the example of load measurement data, the individual load measurement data can be combined or assessed to determine a location where the load is applied to a surface to which the load sensors couple. The measurement data can be displayed on a display that supports a surgeon rapidly assimilating the measurement data. For example, the calculated measurement data on the location of applied load to a surface may have little or no meaning to a surgeon. Conversely, an image of the surface being loaded with a contact point displayed on the surface can be rapidly assimilated by the surgeon to determine if there is an issue with the contact point.

In one embodiment, the orthopedic measurement system transmits and receives information wirelessly. Wireless operation reduces clutter within the surgical area, wired distortion, wired disconnect, or limitations on, measurements caused by the potential for physical interference by, or limitations imposed by, cables connecting a device with an internal power with data collection, storage, or display equipment in an operating room environment. Electronic circuitry 150 includes wireless communication circuitry 162. In one embodiment, wireless communication circuitry 162 is low power and configured for short range telemetry. Typically, distractor 10, module 32, and computer 12 are located in an operating room such that the transmission of measurement data from distractor 10 or module 32 to computer 12 is less than 10 meters. As illustrated, the exemplary communications system comprises wireless communication circuitry 162 of distractor 10 or module 32 and receiving system wireless communication circuitry 180 of computer 12. The distractor 10 or module 32 wireless communications circuitry are inter-operatively coupled to include, but not limited to, the antenna 174, a matching network 172, the telemetry transceiver 170, a CRC circuit 168, a data packetizer 166, and a data input 176. Wireless communication circuitry 162 can include more or less than the number of components shown and are not limited to those shown or the order of the components.

Similarly, computer 12 includes wireless communication circuitry 180 that comprises an antenna 182, a matching network 184, a telemetry receiver 186, a CRC circuit 188, and a data packetizer 190. Notably, other interface systems can be directly coupled to the data packetizer 190 for processing and rendering sensor data. In general, electronic circuitry 150 couples to sensors 152 and is configured to transmit quantitative measurement data to computer 12 in real-time to process, display, analyze, and provide feedback. In one embodiment, distractor 10 includes a magnetic linear sensor configured to measure a distance of distraction and a magnetic angle sensor to measure tilt, slope, or angle. Electronic circuitry 150 is coupled to the magnetic linear sensor and the magnetic angle sensor in distractor 10. The distraction distance data and the M-L tilt measurement data is transmitted by electronic circuitry 150 in distractor 10 to computer 12 and is displayed on display 14. In one embodiment, module 32 includes a plurality of load sensor configured to measure load magnitude at predetermined locations of cover 38 of FIG. 14. Electronic circuitry 150 in module 32 couples to the plurality of load sensors. Module 32 can further include inertial sensors and other parameter measurement sensors. The measurement data from the plurality of load sensors and the inertial sensors is transmitted to computer 12. Computer 12 can further calculate a point of contact to the surface of the cover 38 on a medial side and a lateral side. Computer 12 can calculate the load magnitude at the point of contact on the medial side or the lateral side. The module can further use the inertial sensors as a position measurement system or a tracking system. The tracking data is also sent to computer 12. The results can also be displayed on display 14 of computer 12. Redundant measurement data can be generated from distractor 10 and module 32 such as M-L tilt or A-P tilt. The redundant measurement data can be compared to ensure accuracy of the measurement.

In general, electronic circuitry 150 is operatively coupled to one or more sensors 152 to control a measurement process and to transmit measurement data. Electronic circuitry 150 can be placed near sensors 152 or housed with the sensors to simplify coupling to the sensors. As mentioned previously, electronic circuitry 150 can be placed in distractor 10 and electronic circuitry 150 can be placed in module 32 to control a measurement process and transmit measurement data in each device. Electronic circuitry 150 couples to the magnetic angle sensor and the magnetic distance sensor in distractor 10. Electronic circuitry 150 controls a measurement process of the magnetic angle sensor and the magnetic distances sensor of distractor 10 and transmits measurement data to computer 12. Similarly, electronic circuitry 150 couples to sensors of module 32. Electronic circuitry 150 controls a measurement process of the sensors of module 32 and transmits measurement data to computer 12. In one embodiment, the process of transmitting data from distractor 10 is independent from module 32. Alternatively, the electronic circuitry 150 of distractor 10 can be in communication with the electronic circuitry 150 of module 32 to control the measurement processes and transmission of measurement data. In one embodiment, the transmission of the measurement data from different components can be sent on different channels or the measurement data can be sent at different times on the same channel.

As mentioned previously, wireless communication circuitry comprises data input 176, data packetizer 166, CRC circuit 168 telemetry transmitter 170, matching network 172, and antenna 174. In general, measurement data from sensors 152 is provided to data input 176 of wireless communication circuitry 162. The measurement data can be provided from interface circuitry 160, from the control logic 164, from memory 158, or from control logic 164 thru interface circuitry 160 to data input 176. The measurement data can be stored in memory 158 prior to being provided to data input 176. The data packetizer 166 assembles the sensor data into packets; this includes sensor information received or processed by control logic 164. Control logic 164 can comprise specific modules for efficiently performing core signal processing functions of the distractor 10 or module 32. Control logic 164 provides the further benefit of reducing the form factor to meet dimensional requirements for integration into distractor 10 or module 32.

The output of data packetizer 166 couples to the input of CRC circuit 168. CRC circuit 168 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The output of CRC circuit 168 couples to the input of telemetry transceiver 170. The telemetry transceiver 170 then transmits the CRC encoded data packet through the matching network 172 by way of the antenna 174. Telemetry transceiver 170 can increase a carrier frequency in one or more steps and add the information or measurement data from distractor 10 or module 32 to the carrier frequency. The matching network 172 provides an impedance match for achieving optimal communication power efficiency between telemetry transmitter 170 and antenna 174.

The antenna 174 can be integrated with components of the distractor 10 or module 32 to provide the radio frequency transmission. The substrate for the antenna 174 and electrical connections with the electronic circuitry 150 can further include the matching network. In one embodiment, the antenna and a portion of the matching network 172 can be formed in the printed circuit board that interconnects the component that comprise electronic circuitry 150. This level of integration of the antenna and electronics enables reductions in the size and cost of wireless equipment. Potential applications may include, but are not limited to any type musculoskeletal equipment or prosthetic components where a compact antenna can be used. This includes disposable modules or devices as well as reusable modules or devices and modules or devices for long-term use.

The process for receiving wireless communication circuitry 180 is the opposite of the sending process. Antenna 182 receives transmitted measurement data from wireless communication circuitry 162. Wireless communication circuitry 162 can transmit at low power such that receiving wireless communication circuitry 180 must be in proximity, for example within an operating room to receive measurement data. Antenna 182 couples to matching network 184 that efficiently couples the measurement data to telemetry transmitter circuit 186. The measurement data can be sent on a carrier signal that supports wireless transmission. The measurement data is stripped off from the carrier signal by telemetry transmitter 186. The measurement data is received by CRC circuit 188 from telemetry transmitter 186. CRC circuit 188 performs a cyclic redundancy check algorithm to verify that the measurement data has not been corrupted during transmission. The CRC circuit 188 provides the checked measurement data to data packetizer 190. Data packetizer 190 reassembles the measurement data where it is provided to usb interface 192. USB interface 192 provides the measurement data to computer 12 for further processing. It should be noted that the measuring, transmitting, receiving, and processing of the measurement data can be performed in real-time for use by a surgeon installing the knee joint.

Figure 16:
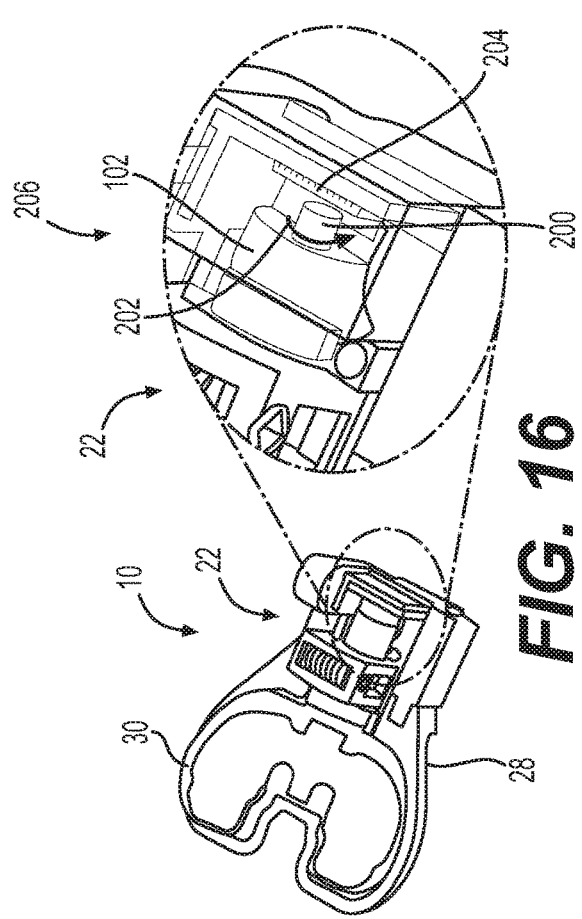
FIG. 16 is an illustration of a magnetic angle sensor coupled to the M-L tilt mechanism in accordance with an example embodiment.

FIG. 16 is an illustration of a magnetic angle sensor 206 coupled to M-L tilt mechanism 22 in accordance with an example embodiment. The illustration includes a magnified view of distractor 10 corresponding to M-L tilt mechanism 22. M-L tilt mechanism 22 couples to moving support structure 30 and can adjust the M-L tilt angle of moving support structure 30. M-L tilt mechanism 22 can be disengaged from moving support structure 30 thereby allowing moving support structure 30 to freely move medially or laterally. A neutral or 0 degrees medial-lateral tilt occurs when a plane of moving support structure 30 is parallel to a plane of fixed support structure 28. Referring briefly to FIG. 12A a coupler 100 of moving support structure 30 is inserted into a coupler 102 of M-L tilt mechanism 22 to retain and align moving support structure 30 to M-L tilt mechanism 22. Coupler 102 freely rotates with M-L tilt mechanism 22 when worm gear 112 of FIG. 13 is disengaged. Conversely, the movement of coupler 102 and moving support structure 30 are locked into the movement of M-L tilt mechanism 22 when worm gear 112 is engaged with gear 114. In other words, M-L tilt mechanism 22 when engaged can forcibly adjust the M-L tilt angle thereby rotating moving support structure 30 and coupler 102 of FIG. 12A medially or laterally.

In one embodiment, magnetic angle sensor 206 comprises a Hall Effect Sensor 204 and a magnet 200. The Hall Effect Sensor 204 can be an integrated circuit that is placed in proximity to magnet 200. In general, the Hall Effect Sensor 204 comprises an array of sensors that detects the perpendicular component of a magnetic field generated by magnet 200. Each sensor generates a signal and the signals are summed and amplified. In one embodiment, the array of sensors are aligned in a circle. Thus, any rotation of the magnet 200 is detected and the amount of rotation can be calculated. In the example, magnet 200 is coupled to coupler 102 thereby rotating as coupler 102 rotates. Hall Effect Sensor 204 is placed adjacent to magnet 200 and within the magnetic field generated by magnet 200. Magnetic angle sensor 206 is a sensor that couples to electronic circuitry 150 as disclosed in FIG. 15 to store angle sensor data or transmit angle sensor data in real-time. Arrow 202 indicates rotation of magnetic 200 in a clockwise direction when facing distractor 10. For example, the clockwise direction can correspond to a medial tilt. Magnetic angle sensor 206 can be calibrated to measure zero degrees when the plane of fixed support structure 28 is parallel with the plane of moving support structure 30. Hall Effect Sensor 204 measures the rotation of magnetic 200 and is calibrated to measure the degrees of rotation as moving support structure 30 tilts medially. The angle sensor data is sent to the computer 12 of FIG. 1 and the amount of medial tilt is displayed on display 14 of FIG. 1 in real-time.

Figure 17:
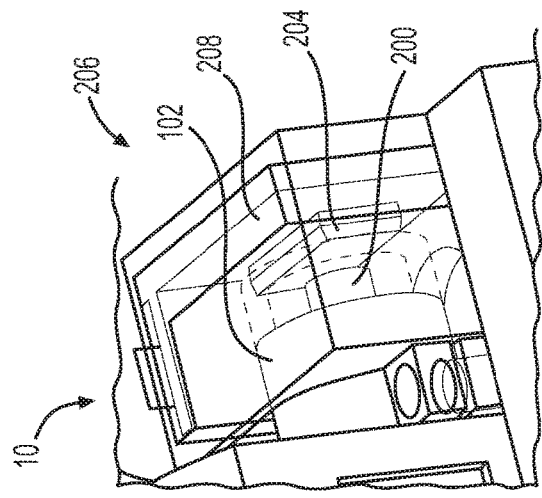
FIG. 17 is an illustration of the magnetic angle sensor in the distractor in accordance with an example embodiment.

FIG. 17 is an illustration magnetic angle sensor 206 in distractor 10 in accordance with an example embodiment. Magnetic angle sensor 206 comprises Hall Effect Sensor 204 and magnet 200. In one embodiment, magnet 200 is coupled to and centered on coupler 102 such that magnet 200 rotates with coupler 102. Hall Effect Sensor 204 can be mounted on a printed circuit board 208 that couples to electronic circuitry 150 of FIG. 15 that can be located in a different area of distractor 10. A planar surface of magnet 200 is positioned centrally to a planar surface of Hall Effect Sensor 204. As mentioned previously, the Hall Effect Sensor 204 is placed within the magnetic field generated by magnet 200.

Figure 18:
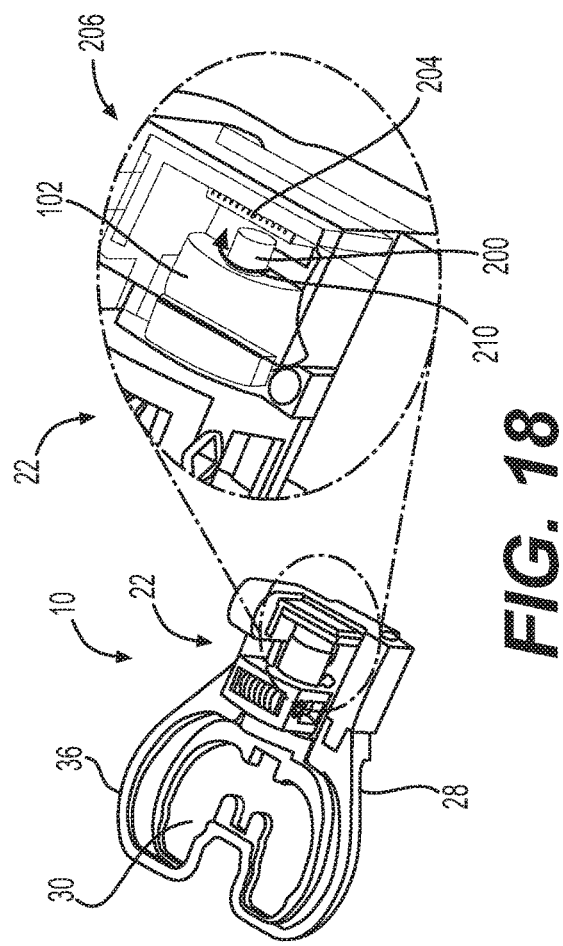
FIG. 18 is an illustration of the moving support structure tilting laterally in accordance with an example embodiment.

FIG. 18 is an illustration of moving support structure 30 tilting laterally in accordance with an example embodiment. In the example, magnet 200 is coupled to coupler 102 thereby rotating as coupler 102 rotates. Hall Effect Sensor 204 is placed adjacent to magnet 200 and within the magnetic field generated by magnet 200. The magnetic angle sensor 206 couples to electronic circuitry 150 as disclosed in FIG. 15 to receive and transmit magnetic angle sensor data. Arrow 210 indicates rotation of magnetic 200 in a counter-clockwise direction when facing distractor 10. For example, the counter-clockwise direction can correspond to a lateral tilt. Magnetic angle sensor 206 can be calibrated to measure zero degrees when the plane of fixed support structure 28 is parallel with the plane of moving support structure 30. Hall Effect Sensor 204 measures the rotation of magnetic 200 and is calibrated to measure the degrees of rotation as moving support structure 30 tilts laterally as shown. The magnetic angle sensor data is sent to the computer 12 of FIG. 1 and the amount of medial tilt is displayed on display 14 of FIG. 1 in real-time.

Figure 19:
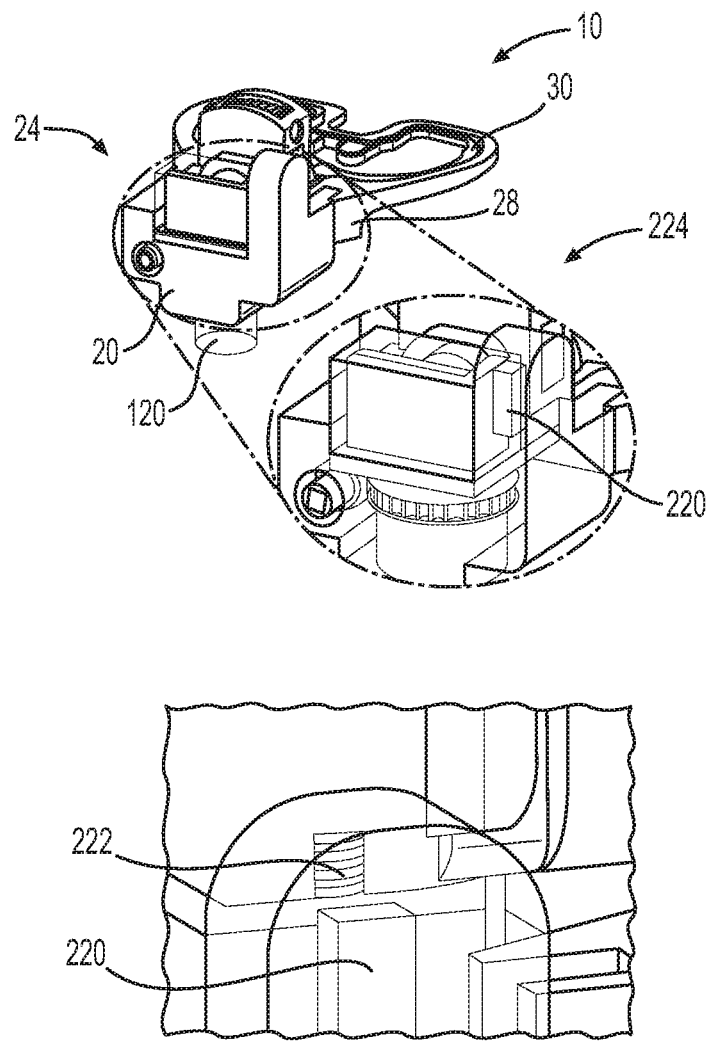
FIG. 19 is an illustration of a magnetic distance sensor in the distractor in accordance with an example embodiment.

FIG. 19 is an illustration of a magnetic distance sensor 224 in distractor 10 in accordance with an example embodiment. In one embodiment magnetic distance sensor 224 comprises a magnet 220 and a Linear Hall Sensor 222. The magnetic distance sensor 224 provides contactless position measurement. Magnet 220 is a two pole magnet. Linear Hall Sensor 222 can measure absolute position of lateral movement when placed in the magnetic field of magnet 220. The strength of the magnetic field measured by Linear Hall Sensor 222 corresponds to distance but is not linear to distance. Linear Hall Sensor 222 relates the non-linear change in magnetic field strength per unit distance and linearizes the output. Linear Hall Sensor 222 couples to electronic circuitry 150 of FIG. 15 in distractor 10 where electronic circuit 150 is configured to control a measurement process and transmit distraction distance data.

In one embodiment, Linear Hall Sensor 222 is coupled to a portion of distraction mechanism 24 that moves relative to housing 20 and fixed support structure 28 of FIG. 14. For example, Linear Hall Sensor 222 can couple to post 120 of distraction mechanism 24 that increases or decreases a distraction distance of moving support structure 30 relative to fixed support structure 28. Operation of distraction mechanism 24 and post 120 is disclosed in more detail in FIG. 14. Magnet 220 is coupled to housing 20 such that Linear Hall Sensor 222 is in proximity to magnet 220. In one embodiment, Linear Hall Sensor 222 and magnet 220 align to an axis to which a distance is measured. In the example, the axis can align with pole 120. A reference distance can be established corresponding to distractor 10 being at a minimum distraction distance for the medial and lateral compartment heights with a medial-lateral tilt angle of zero. The reference distance can be displayed on display 14 of computer 12 of FIG. 1. As post 120 changes position to increase a distraction distance of distractor 10, Linear Hall Sensor 222 measures the magnetic field from magnet 220 whereby the measured magnetic field strength corresponds to distance of Linear Hall Sensor 222 from magnet 220. The measured change in height can be added to the reference distance to arrive at the medial and lateral compartment heights. Electronic circuitry 150 in distractor 10 receives and transmits distraction distance data from Linear Hall Sensor 222 to computer 12 of FIG. 1. Alternatively, Linear Hall Sensor 222 can be placed on housing 20 and magnet 220 can be coupled to post 120 such that magnet 220 moves relative to Linear Hall Sensor 222. In one embodiment, Magnetic distance sensor 224 can be used in conjunction with magnetic angle sensor 206 to calculate medial or lateral compartment heights. Computer 12 can receive the height measurement data and the angle measurement data geometrically calculate the medial height and the lateral compartments heights. In one embodiment, the medial height and the lateral compartment heights will be measured at a known position on the medial surface of the module 32 and a known position on the lateral surface of module 32.

Figure 20:
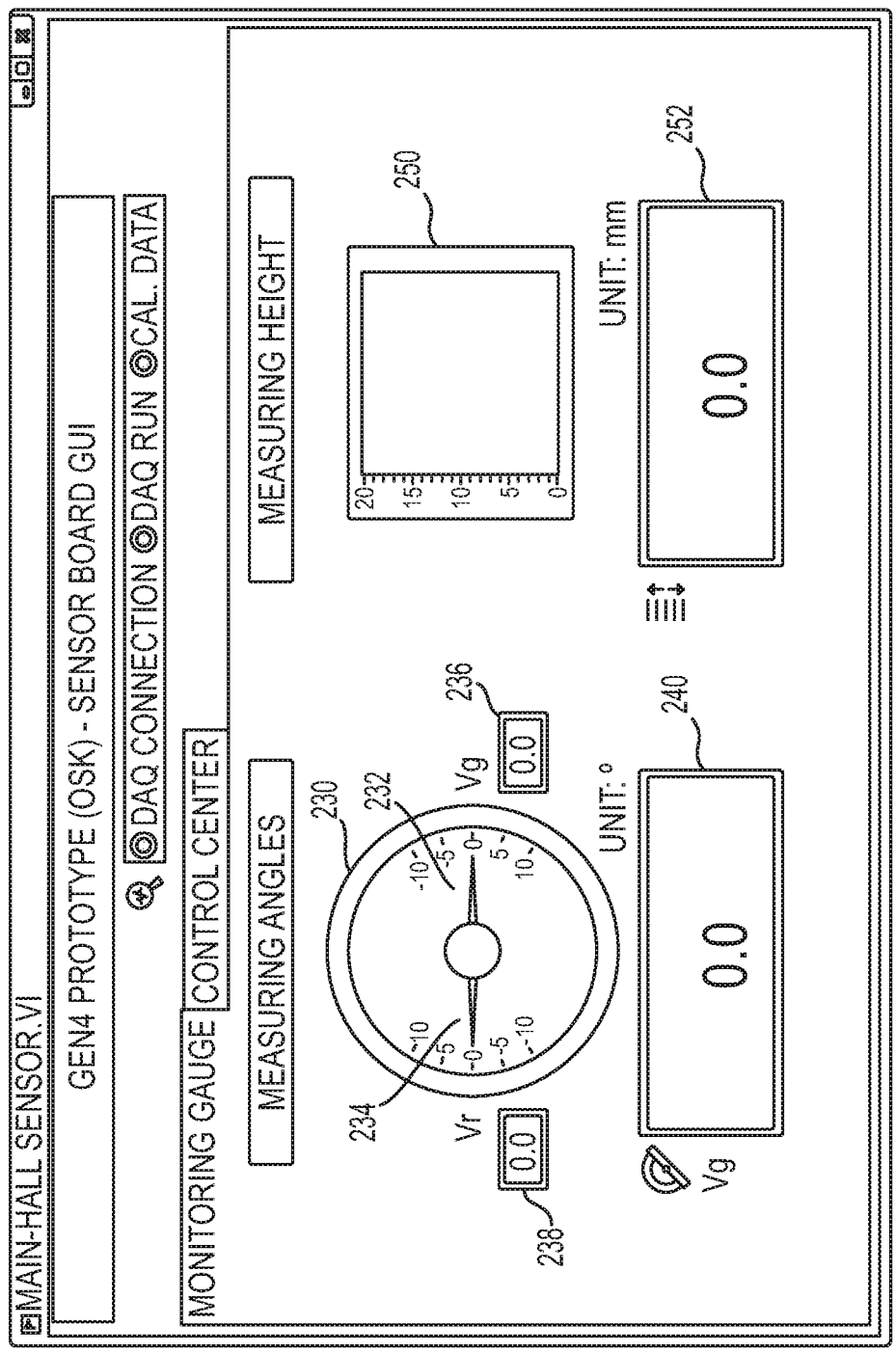
FIG. 20 is an illustration of the display of the computer as shown in FIG. 1 in accordance with an example embodiment.

FIG. 20 is an illustration of display 14 of computer 12 as shown in FIG. 1 in accordance with an example embodiment. Electronic circuitry 150 of FIG. 15 in distractor 10 transmits distraction distance data and M-L tilt data to computer 12. In a surgical environment reducing patient time under anesthesia lowers patient risk of complication or death. A surgeon using quantitative measurement data during orthopedic surgery must absorb the measurement data rapidly to support installation of prosthetic components in the shortest possible time. Display 14 of FIG. 1 can visualize data in a manner that allows the surgeon to rapidly determine if the measurement data verifies the subjective feel of an installation or if the installation needs correction and how much. Moreover, display 14 of FIG. 1 supports real-time measurement as a correction or adjustment is made.

In one embodiment, M-L tilt data is displayed on a meter 230. Meter 230 can comprise a first indicator 232 and a second indicator 234. Indicators 232 and 234 comprises opposing pointers that point to a graduated scale on either side of meter 230 corresponding to degrees of medial or lateral tilt. This supports at a glance an imbalance or offset of alignment. Meter 230 can also be used during an equalization step. The equalization step engages M-L tilt mechanism 22 of FIG. 1 to forcibly adjust the M-L tilt to zero. The M-L tilt at zero degrees corresponds to a plane of fixed support structure 28 of FIG. 1 being parallel to a plane of moving support structure 30 of FIG. 1. The actual quantitative measurement data related to M-L tilt can be displayed with boxes 236, 238, and 240 on display 14.

In one embodiment, distraction distance data is displayed on display 14. Distraction distance corresponds to a distance between a distal end of a femur and a proximal end of a tibia and is displayed visually on display 14. A bar chart 250 provides a visual representation of the distraction distance. Distraction distance values are displayed on one side of the bar graph. A bar in bar chart 250 indicates the distance and is adjacent to the distance values. The distraction distance value can also be display in a box 252 on display 14. A medial or lateral height respectively of the medial compartment and the lateral compartment of a knee joint can be calculated by computer 12 and displayed by display 14.

Figure 21:
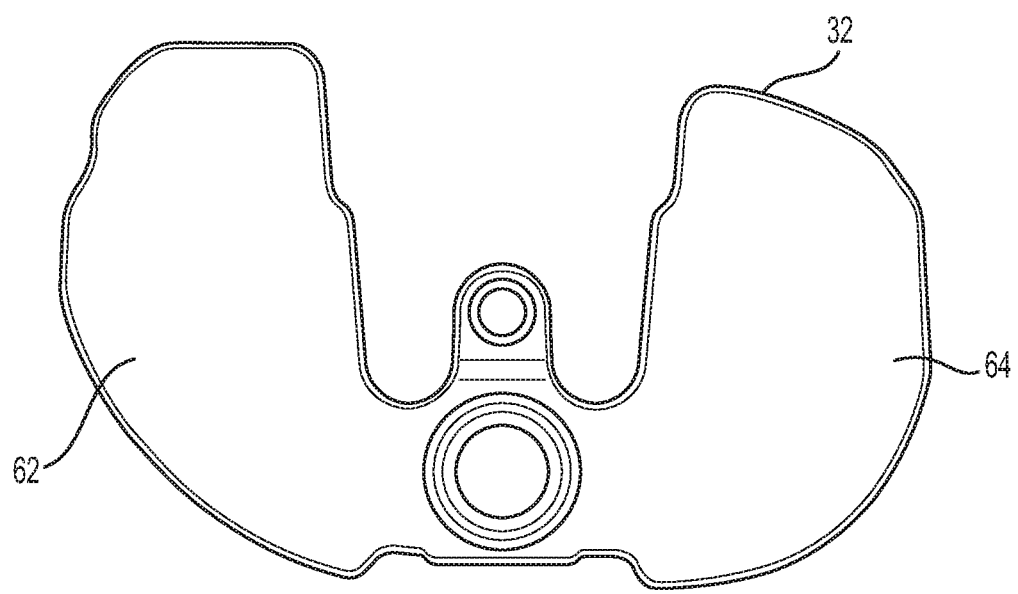
FIG. 21 is an illustration of a top view of the module in accordance with an example embodiment.

FIG. 21 is an illustration of a top view of module 32 in accordance with an example embodiment. Module 32 includes at least one sensor for measuring a parameter of the musculoskeletal system. In the example, module 32 includes a plurality of load sensors configured to measure a load applied to a surface 62 and a surface 64 also shown in FIG. 3. The plurality of load sensors are coupled to predetermined locations of surface 62 and 64 that define an area of contact. In one embodiment, each load sensor couples to a vertex of a polygon. As previously mentioned, cover 38 as shown in FIG. 2 couples to module 32 when placed in distractor 10. Cover 38 couples to surface 62 and 64. The predetermined locations of the plurality of load sensors translates to locations on cover 38 that determine a location of medial or lateral condyle contact on cover 38.

Module 32 can also be used in trialing the knee joint prior to a final installation of final prosthetic components. For example, a tibial prosthetic component and femoral prosthetic component are installed using the quantitative measurement data from distractor 10 and module 32 as shown in FIG. 1 to determine bone cuts, alignment, and balance. A trialing insert can then be inserted in the tibial prosthetic to take further measurements. The trialing insert can comprise module 32 and a cover. The cover is configured to couple to the femoral prosthetic component. The combined thickness of module 32 and the cover is determined by the bone cuts and measurements made by distractor 10. In one embodiment, the insert comprising module 32 and the cover is inserted in the tibial prosthetic component. Measurements from module 32 as a trialing insert should be similar to the measurements taken with distractor 10 and module 32. Further adjustments can be made to fine tune the prosthetic component installation using quantitative measurement data. The trialing insert can then be removed and the final insert installed in the knee joint. The final insert should have loading, position of load, balance, and alignment approximately equal to that measured using the trialing insert.

Figure 22:
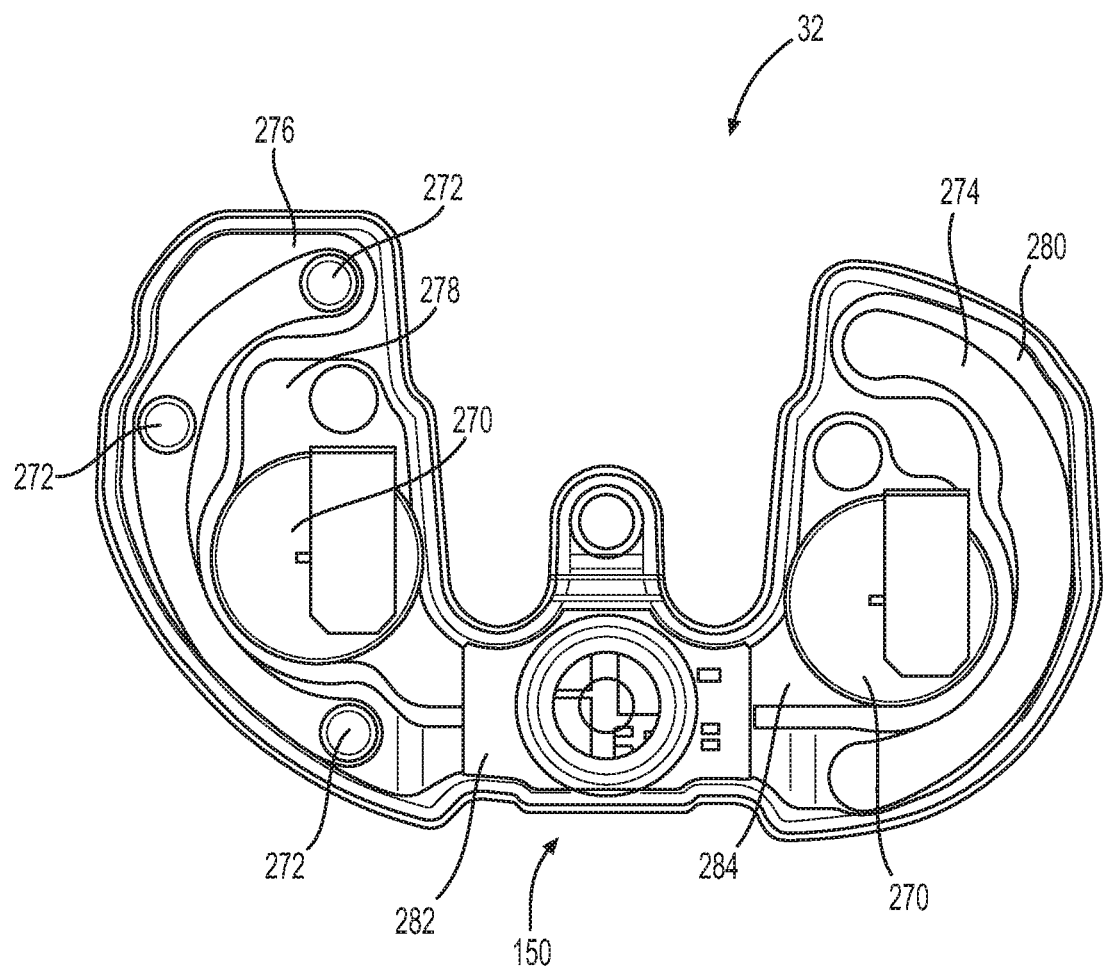
FIG. 22 is an illustration of the module with a portion of an enclosure removed in accordance with an example embodiment.

FIG. 22 is an illustration of module 32 with a portion of an enclosure removed in accordance with an example embodiment. Module 32 comprises electronic circuitry 150 and at least one sensor configured to measure a parameter. Module 32 comprises a first support structure and a second support structure configured to form a housing that is hermetically sealed. In the example embodiment, a plurality of load sensors 272 are shown on a medial side of module 32. Plurality of load sensors 272 are placed at predetermined locations in module 32 to support measuring a position of load applied to the medial side. A load plate that is not shown would overlie plurality of load sensors 272. A plurality of load sensors are also placed at predetermined locations on a lateral side of module 32 although they cannot be seen in FIG. 22. A load plate 274 overlies the plurality of load sensors on the lateral side. Load plate 274 distributes loading to a load sensor. In one embodiment, the plurality of load sensors 272 are formed in flexible interconnect 276. Similarly, the plurality of load sensors underlying load plate 274 can be formed in interconnect 280. The leads of the plurality of load sensors 272 couple to electronic circuitry 150 as previously disclosed in FIG. 15.

Electronic circuitry 150 can be coupled to a printed circuit board 282. Electronic components can be coupled to, formed in, or interconnected to form a circuit on printed circuit board 282. In one embodiment, leads from plurality of load sensors 272 on flexible interconnect 276 and 280 can be coupled to printed circuit board 282 by solder bumping. Electronic circuitry 150 is placed in a region of module 32 that is not subject to loading by the musculoskeletal system. Electronic circuitry 150 controls a measurement process and transmits measurement data from plurality of load sensors 272. Electronic circuitry 150 receives power from a power source. In one embodiment, the power source comprises batteries 270. At least a portion of each battery underlies a portion of a surface that is loaded by the musculoskeletal system. The battery form factor is such that compression of module 32 under load by the musculoskeletal system does not touch batteries 270. Batteries 270 are coupled to electronic circuitry 150 by flexible interconnect 278 and 284. Flexible interconnect 278 and 284 can couple to electronic circuitry 150 by solder bump to printed circuit board 282.

Figure 23:
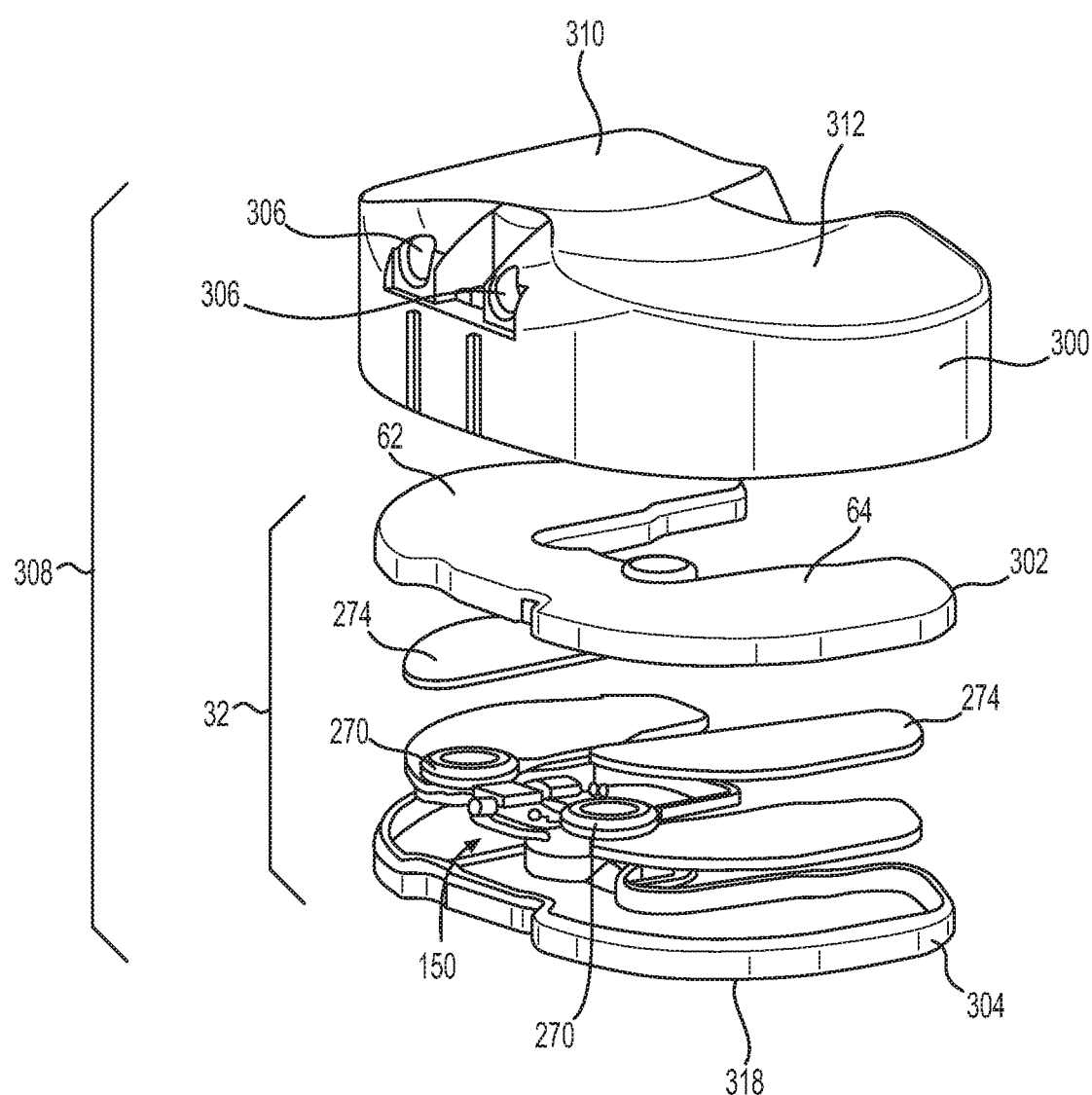
FIG. 23 is an exploded view of an insert prosthetic component in accordance with an example embodiment.

FIG. 23 is an exploded view of an insert 308 prosthetic component in accordance with an example embodiment. Insert 308 comprises a cover 300 and module 32. Distractor 10 of FIG. 1 uses module 32 to support one or more bone cuts for installation of one or more prosthetic components of the knee joint. In general, the load magnitude, position of load, balance, and alignment of the knee joint is measured. The size and height of the prosthetic components are taken into account in the bone cuts supported by distractor 10. After a tibial bone cut has been completed a tibial prosthetic component can be installed in a proximal end of a tibia. The tibial prosthetic component can be a trial tibial prosthetic component or a final tibial prosthetic component. Similarly, a femoral prosthetic component can be installed on a distal end of a femur after the femoral bone cuts on a distal end of the femur are made.

Module 32 comprises a support structure 302 and a support structure 304. Support structures 302 and 304 when coupled together form a housing for at least one sensor, a power source, and electronic circuitry 150. The housing is hermetically sealed by welding, adhesive, glue, mechanical coupling, blocking channels or other techniques. Support structure 302 has a surface 62 and a surface 64 configured to respectively couple to an articular surface 310 and an articular surface 312 of cover 300. Articular surfaces 310 and 312 support movement of the knee joint over a range of motion of the leg. Support structure 304 has a surface 318 that couples to a surface of the tibial prosthetic component.

Electronic circuitry 150 is placed in a lightly loaded or unloaded area of module 32. Electronic circuitry 150 controls a measurement process and transmits measurement data to a computer 12 shown in FIG. 1. The computer 12 is in the operating room and the transmission of the measurement data is short range. In one embodiment, a first plurality of load sensors underlie and couple to surface 64 at predetermined locations. Similarly, a second plurality of load sensors underlie and couple to surface 62 at predetermined locations. The predetermined locations correspond to vertexes of a polygon that define a measurement region. Load plates 274 couple between surface 64 and surface 62 of support structure 302 and the first or second plurality of load sensors. Load plates 274 distribute loading applied to surface 260 or surface 262 to the first or second plurality of load sensors. A power source couples to electronic circuitry 150 and the first and second plurality of load sensors. In one embodiment, the power source comprises batteries 270. Batteries 270 can be single use or rechargeable batteries.

Cover 300 couples to module 32. Module 32 and cover 300 have one or more retaining features that couple module 32 to cover 300. The retaining features allow cover 300 to be removed from module 32. Cover 300 further includes openings 306 that are configured to receive a handle to direct and install insert 308 in the knee joint. In one embodiment, a plurality of covers can be provided. The plurality of covers each have a different height or thickness. The combined thickness of module 32 and a cover corresponds to a height or thickness of a final insert that is installed into the prosthetic knee joint. The plurality of covers can also include covers of a different size that support optimal fitting for different bone sizes. In general, a cover is selected that corresponds to a patient femur and tibia bone size and a thickness corresponding to a spacing between the femoral prosthetic component and the tibial prosthetic component.

Insert 308 is installed in the knee joint. Insert 308 couples to and is retained by the trial or permanent tibial prosthetic component. Cover 300 and module 32 have a height or thickness that corresponds to the distraction distance of the knee joint when using distractor 10 as disclosed herein above to support prosthetic component installation. Condyles of the femoral component couple to articular surfaces 310 and 312 of cover 30. Articular surfaces 310 and 312 of cover 300 respectively couple to surfaces 62 and 64 of module 32. The first plurality of load sensors and the second plurality of load sensor generate load measurement data that is sent to from module 32 to the computer 12 shown in FIG. 1. Typically, computer 12 is in the operating room where the surgeon can review the quantitative measurement data while performing the knee joint installation. The predetermined locations of the first or second plurality of sensors correspond to locations on articular surfaces 310 and 312. The computer uses load data from the load sensors to calculate a load magnitude and a position of load where a condyle contacts an articular surface and displays it on the computer in real-time. The load magnitudes, position of load, balance, and alignment of the knee joint should be similar to the measurement data using distractor 10 of FIG. 1. Further adjustments or refinements can be made to change a load magnitude, a position of load, balance, or knee joint alignment. Typically, the adjustment can comprise rotating a prosthetic component or applying soft tissue release but bone resection is also an option if the measurement data justifies the change. The changes in quantitative measurement data can be viewed on the display as the adjustments are made to ensure optimal joint installation. The final insert is then placed in the knee joint. The final knee joint should see load magnitudes, position of load, balance, and alignment equal to insert 308. Thus, module 32 is used in distractor 10 of FIG. 1 to generate quantitative measurement data to support one or more bone cuts prior to installation of at least one prosthetic component and module 32 is used in an insert 308 to provide quantitative measurement data on the prosthetic knee joint.

Figure 24:
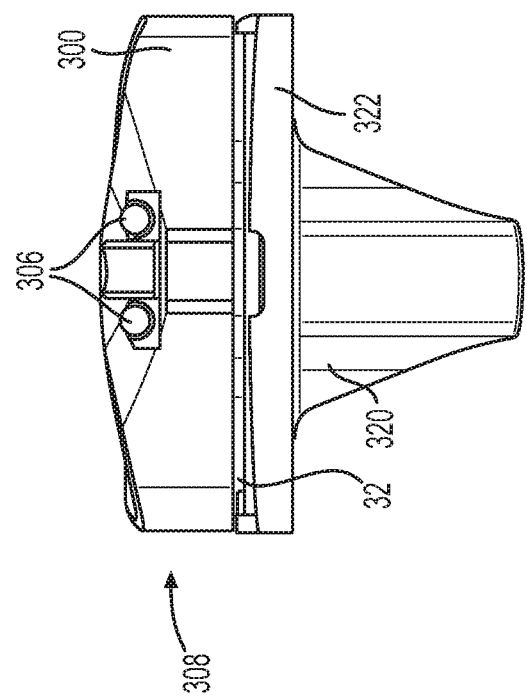
FIG. 24 is an anterior view of the insert installed on a tibial prosthetic component in accordance with an example embodiment.

FIG. 24 is an anterior view of insert 308 installed on a tibial prosthetic component 320 in accordance with an example embodiment. Insert 308 comprises cover 300 coupled to module 32. In one embodiment, tibial prosthetic component 320 includes a tibial tray 322. The tibial tray 322 is configured to align and retain module 32 to tibial prosthetic component 320. In one embodiment, load data is transmitted from insert 308 to the computer 12 shown in FIG. 1.

Figure 25:
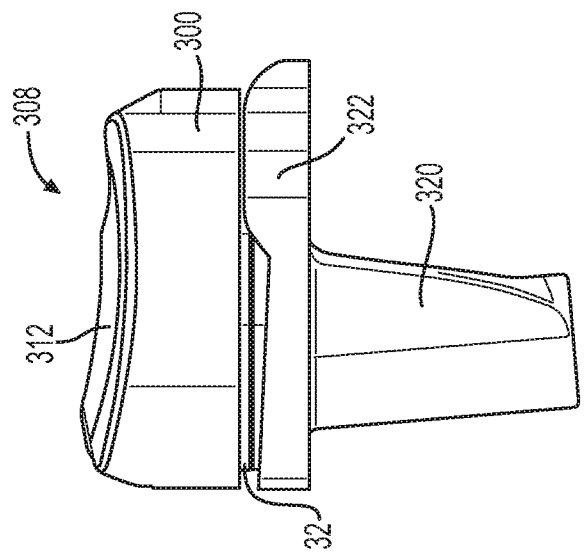
FIG. 25 is a side view of the insert installed on the tibial prosthetic component in accordance with an example embodiment.

FIG. 25 is a side view of insert 308 installed on the tibial prosthetic component 320 in accordance with an example embodiment. Articular surface 312 of cover 300 has a curved surface that supports coupling to a condyle of a femoral prosthetic component.

Figure 26:
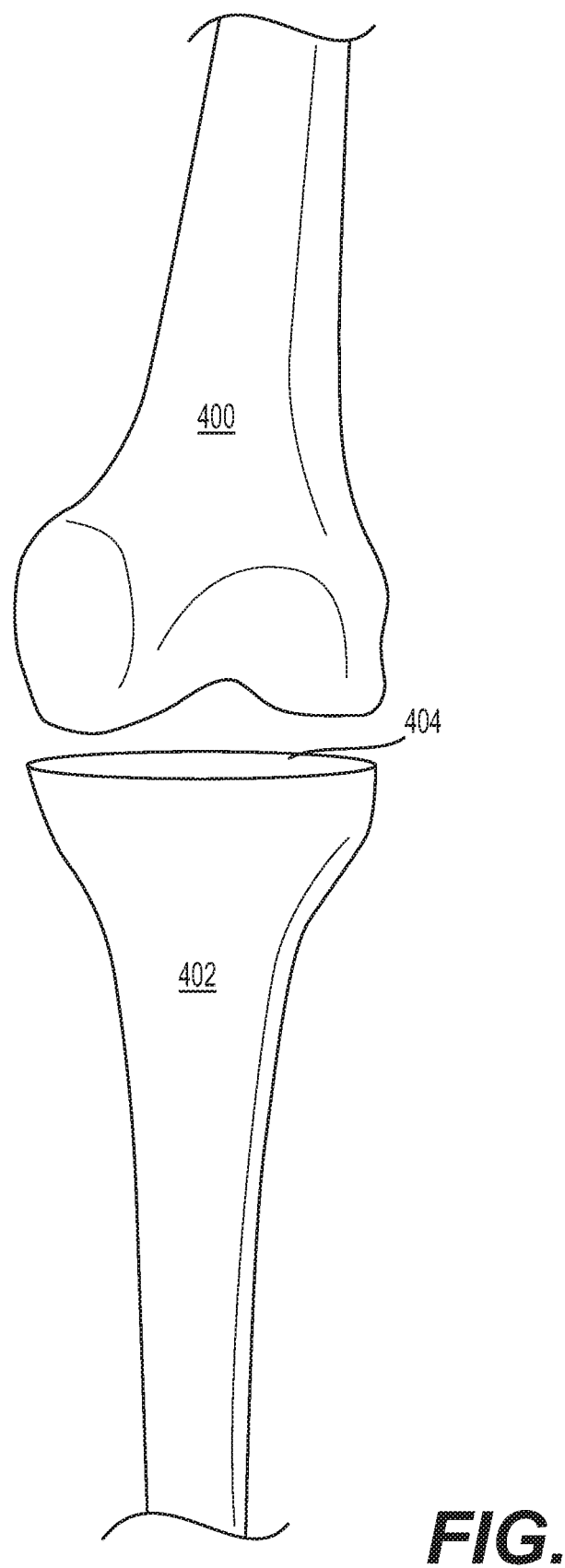
FIG. 26 illustrates a step in a knee joint installation procedure in accordance with an example embodiment.

FIG. 26 illustrates a step in a knee joint installation procedure in accordance with an example embodiment. In general, a bone in a knee joint is prepared to interface with distractor 10 shown in FIG. 1. In the example, a tibia 4020 is selected for resection. A proximal end of a tibia is resected and is prepared to receive a tibial prosthetic component. In one embodiment, the proximal end of tibia 4020 is cut perpendicular to the tibia anatomical axis using an alignment jig. For example, an extramedullary alignment tool can be used align and cut the proximal end of the tibia 4020. The resection can also include an anterior-posterior (A-P) slope to the prepared bone surface 404. In one embodiment an (A-P) slope of 6 degrees slanted posteriorly is made. The distal end of femur 400 is left in a natural state.

Figure 27:
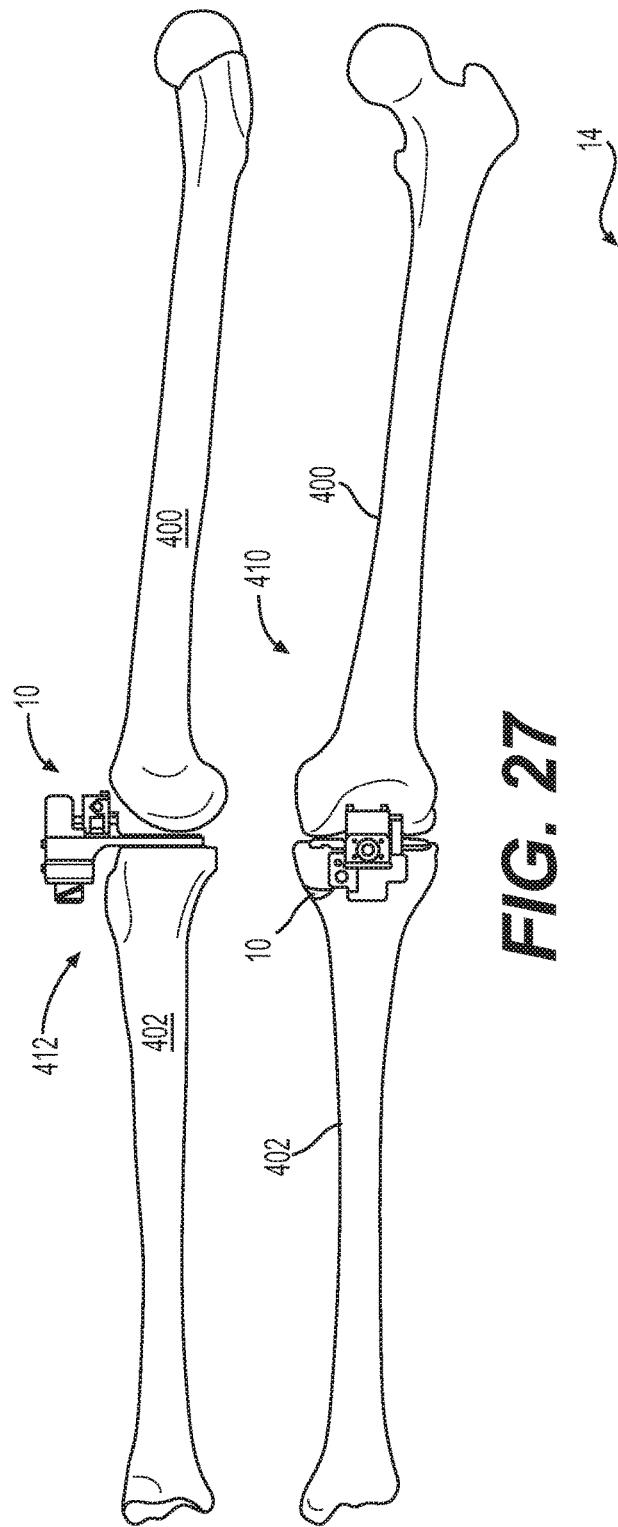
FIG. 27 illustrates a step of placing the distractor in the knee joint of the leg in accordance with an example embodiment.

FIG. 27 illustrates a step of placing distractor 10 in the knee joint of the leg in accordance with an example embodiment. A lateral view 412 of the leg and a top view of the 410 leg is shown in FIG. 27. In the example, the leg is placed in extension. The distractor 10 is reduced to a minimum distraction distance and placed on the prepared surface of the proximal end of tibia 402. At the minimum distraction distance distractor 10 should not require substantial force to fit within the knee joint. Placing distractor 10 at a minimum distraction distance is also called zeroing distractor 10. A module 32 and a cover 38 is placed on moving support structure 30 as shown in FIG. 1. In one embodiment, a bottom surface of both the moving support structure and the fixed support structure contact the prepared bone surface of tibia 402.

A M-L tilt lock on distractor 10 is then released. The M-L tilt lock releases moving support structure 30 as shown in FIG. 13 to freely swivel medially or laterally. In one embodiment, the moving support structure 30 cannot tilt when distractor 10 is at the minimum height. In one embodiment, the knee joint is not stable with distractor 10 zeroed. The knee joint can be supported to prevent the leg from hyperextending due to laxity. The distraction distance of distractor 10 is increased until the knee joint does not require support because the knee joint pressure is sufficient to prevent hyperextension when the leg is raised by supporting the ankle while observing the knee joint pressure medially and laterally. Condyles of the femur couple to cover 38 as shown in FIG. 3. Module 32 underlying cover 38 measures loading applied to cover 38 and transmits the load data to a computer 12 shown in FIG. 1 for further processing. Distractor 10 also measures and transmits distraction distance data and M-L tilt angle data to computer 12 shown in FIG. 1.

Figure 28:
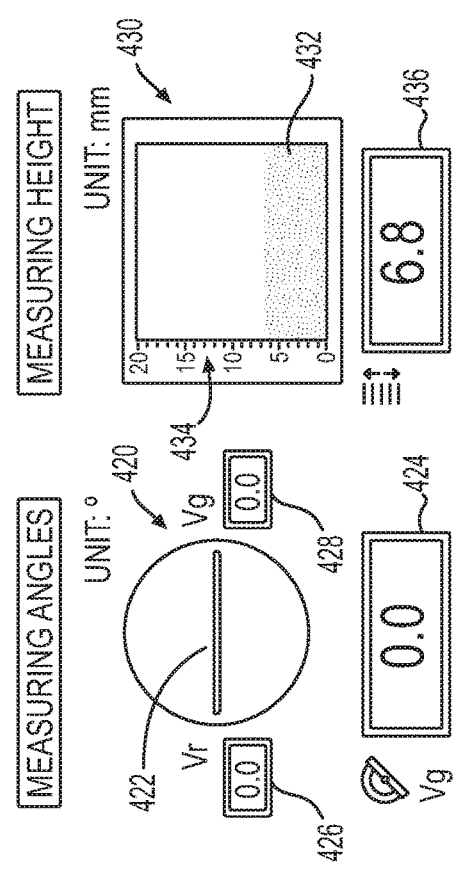
FIG. 28 illustrates a step of displaying the distraction distance data and the M-L tilt angle on a display in real-time in accordance with an example embodiment.

FIG. 28 illustrates a step of displaying the distraction distance data and the M-L tilt angle on a display in real-time in accordance with an example embodiment. A display 14 couples to the computer 12 receiving distraction distance data and M-L tilt angle data from distractor 10 similar to that shown in FIG. 20. The computer 12 provides the M-L tilt angle data and the distraction distance data on display 14 in real-time. Display 14 shows an M-L tilt meter 420 configured to display the M-L tilt angle of moving support structure 30 as shown in FIG. 1. M-L tilt meter 420 comprises an indicator bar 422 that indicates medial and lateral tilt. A surgeon at a glance can determine the amount of M-L tilt and whether the M-L tilt is medial or lateral. The value of the medial tilt angle and the lateral tilt angle can also be seen in boxes 426 and 428 on display 14. A tilt angle can also be placed in box 424 for increased visibility to the surgeon. Alternatively, M-L tilt meter 420 can have a graduated scale on either side of M-L tilt meter 420 that allows indicator bar 422 to point to the medial or lateral tilt angle value.

Display 14 also shows a bar graph 430 configured to indicate the distraction distance of distractor 10. A scale 434 indicates the distraction distance and is adjacent to bar graph 430. A bar 432 in bar graph 430 indicates the distraction distance but the exact distraction distance can be read by reading the height of bar 432 from scale 434. The distraction distance can also be read from a box 436. Similar to M-L tilt meter 420, bar graph 430 allows the surgeon to determine the distraction distance at a glance. In one embodiment, there will two bar graphs, a first bar graph is a measure of a height of the medial compartment and a second bar graph is a measure of a height of the lateral compartment of the knee joint. Each bar graph can indicate distance by graph or numeric value.

Figure 29:
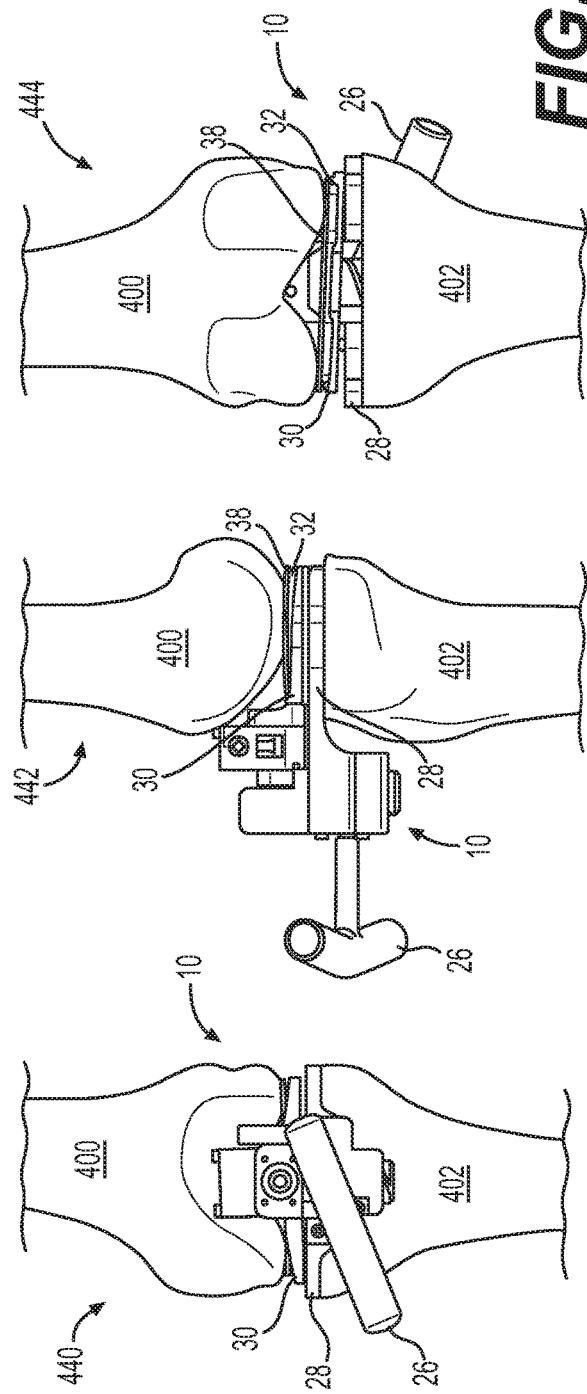
FIG. 29 illustrates a step of increasing the distraction distance until a predetermined loading is achieved in accordance with an example embodiment.

FIG. 29 illustrates a step of increasing the distraction distance until a predetermined loading is achieved in accordance with an example embodiment. In general, a predetermined loading as disclosed herein above and below does not imply a specific load value but a value chosen by a user. The predetermined loading can also be within a range or predetermined range. For example, the predetermined loading can be within a range of 20-40 lbs or 20-60 lbs for a knee joint. It can vary greatly depending on the musculoskeletal system or the joint system surgical apparatus 10 is used on. The user of surgical apparatus 10 will select the predetermined load value a medial or lateral compartment is set at. Similarly, a predetermined height is a height selected by the user or within a predetermined range set by the user or a component manufacturer. An anterior view 440, a side view 442, and a posterior view 444 of the knee joint is shown in FIG. 29 to illustrate placement of distractor 10. Fixed support structure 28 couples to the prepared bone surface of the proximal end of tibia 402. Module 32 is placed on moving support structure 30. Cover 38 couples to module 32. The condyles of femur 400 couple to cover 38. The load applied by the condyles of femur 400 to cover 38 is measured by load sensors in module 32 and transmitted to computer 12 as shown in FIG. 1.

Knob 26 couples to the distraction mechanism in distractor 10. Rotating knob 26 increases or decreases the distraction distance of distractor 10. In one embodiment, knob 26 is rotated to increase the distraction distance. Increasing the distraction distance will increase the tension on the ligaments of the knee thereby increasing the loading applied by the condyles to cover 38 and thereby module 32. In general, module 32 measures the loading applied to cover 38 and is displayed on display 14 as shown in FIG. 1. The surgeon increases the distraction distance until a predetermined loading is achieved. The predetermined loading corresponds to a known value that supports increased performance and reliability of the knee joint. In the example, moving support structure 30 has been released to swing freely medially or laterally. Typically, only one side (medial or lateral) will be distracted to the predetermined loading. The side not at the predetermined loading will be at a lesser value. The distractor 10 is then locked such that moving support structure 30 cannot increase or decrease the distraction distance.

Figure 30:
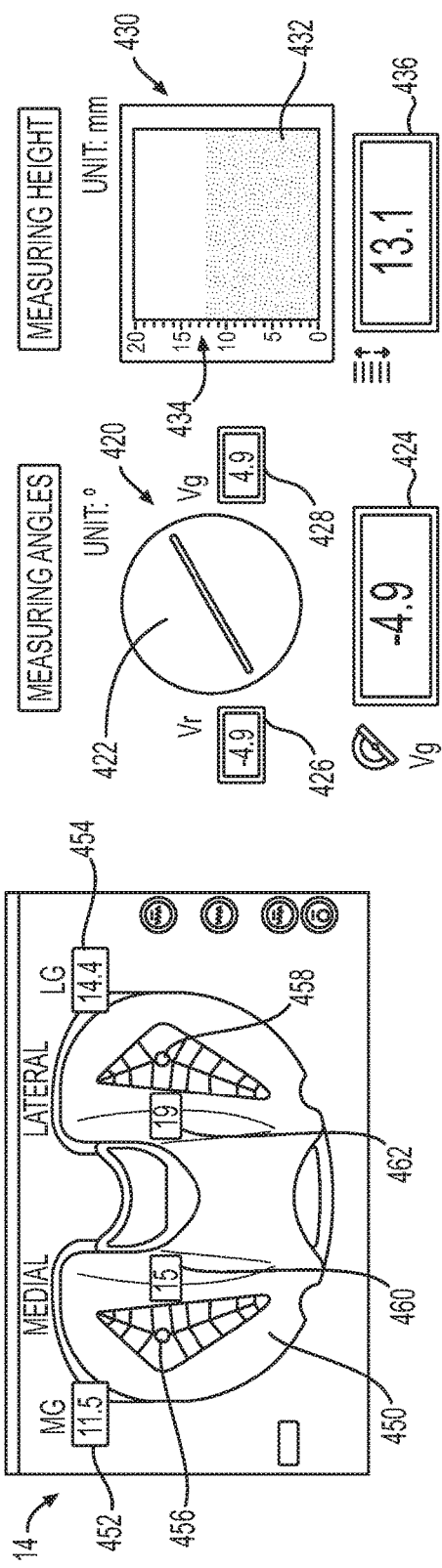
FIG. 30 illustrates a step of reviewing the position of load, the load magnitude, M-L tilt angle, and the distraction distance on the display as the distraction distance of the distractor is increased in accordance with an example embodiment.

FIG. 30 illustrates a step of reviewing the position of load, the load magnitude, M-L tilt angle, and the distraction distance on display 14 as the distraction distance of distractor 10 is increased in accordance with an example embodiment. The description will include components of FIG. 1 and FIG. 29. The quantitative measurement data is sent to computer 12 from distractor 10 and module 32. Display 14 includes a top view of cover 38. Circle 456 and circle 458 represent a location where the medial and lateral condyles of femur 400 respectively couple to a medial and lateral side of cover 38. Medial load magnitude data is indicated in box 460 and lateral load magnitude data is indicated in box 462. As mentioned previously, moving support structure 30 is allowed to freely rotate in a medial or lateral direction. Knob 26 is rotated until the distraction distance of distractor 10 is increased to the predetermined loading. In the example, the distraction distance is no longer increased when the lateral side of cover 38 measures 19 pounds at circle 458. Note that the loading is not balanced and the medial side of cover 38 measures 15 pounds at circle 460. Distractor 10 is then locked to prevent movement of moving support structure 30 shown in FIG. 29. In one embodiment, the predetermined load on the medial and lateral surface of cover 38 is in a range from 20 to 40 pounds.

Tilt meter 420 also shows an imbalance related to the M-L tilt angle of moving support structure 30 as shown in FIG. 29. Tilt meter 420 indicates the lateral side of moving support structure 30 is higher than the medial side. The measured M-L tilt angle is indicated in box 424 and corresponds to an angle between the plane of moving support structure 30 and the plane of fixed support structure 28. In the example, box 424 indicates an M-L tilt angle of −4.9 degrees. The distraction distance is also indicated on display 14. Bar graph 434 illustrates the distraction distance while box 436 provides a value of the distraction distance. In the example, box 436 indicates the distraction distance is 13.1 millimeters. In one embodiment, the distraction distance is an average because moving support structure 30 has an M-L tilt angle.

The height of the lateral compartment and the height of the medial compartment can also calculated from the distraction distance data and the M-L angle data. In one embodiment, the height of the medial compartment corresponds to a distance from the prepared bone surface of the tibia to the point where the medial condyle couples to the medial side of cover 38. Similarly, the height of the lateral compartment corresponds to a distance from the prepared bone surface of the tibia to the point where the lateral condyle couples to the lateral side of cover 38. The height of the medial compartment and the height of the latera compartment take into account the slope of moving support structure 30. The height of the medial compartment is indicated in box 452 and the height of the lateral compartment is indicated in box 454. In the example, the medial gap is 11.5 millimeters and the lateral gap is 14.4 millimeters. The difference in the height of the medial compartment and the height of the lateral compartment corresponds to an offset of the femur relative to the mechanical axis of the leg.

Figure 31:
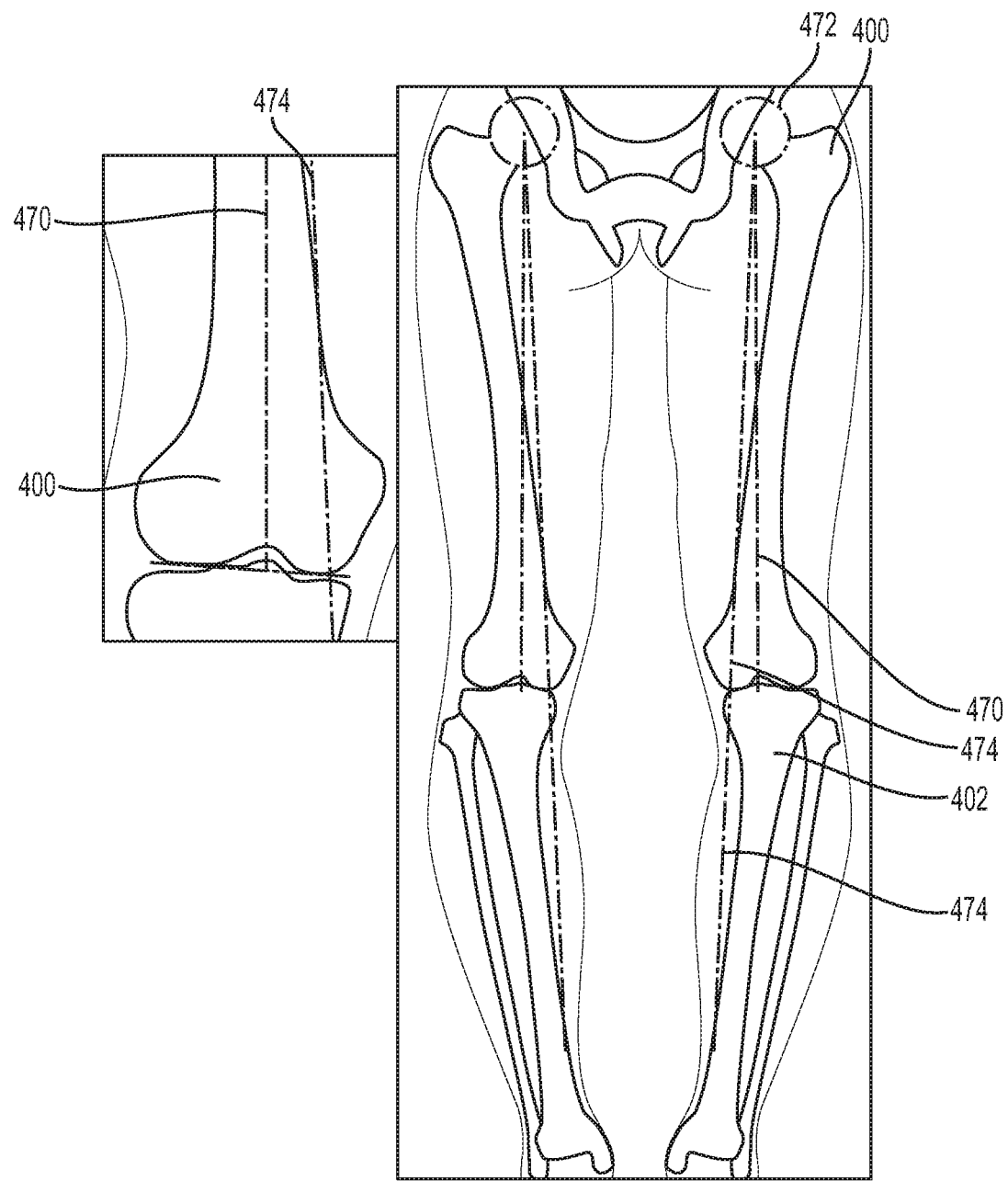
FIG. 31 illustrates a step of reviewing an x-ray in accordance with an example embodiment.

FIG. 31 illustrates a step of reviewing an x-ray of the leg in accordance with an example embodiment. The x-ray illustrates a femoral offset relative to the mechanical axis of the leg. Femur 400 is shown in the x-ray. A line 470 corresponds to a mechanical axis through femur 400. The mechanical axis couples through a center of a femoral head 472 to a center of the intercondylar notch of a distal end of femur 400. An offset or misalignment of femur 400 from the mechanical axis corresponds to line 474. Line 474 is a line drawn from the center of femoral head 472 to a center of the ankle.

Typically, the offset of femur 400 is measured prior to or during a knee replacement surgery. As shown, lines 470 and 474 can be drawn on the x-ray and the offset can be measured with a protractor or other angle measurement device. In one embodiment, the angle formed by lines 470 and 474 corresponds to the M-L tilt angle measured in FIG. 30. The offset measured in the x-ray is compared against the M-L tilt angle measured by distractor 10 as seen in FIG. 1. In general, the M-L tilt angle and the offset angle measured in the x-ray should be approximately equal.

Figure 32:
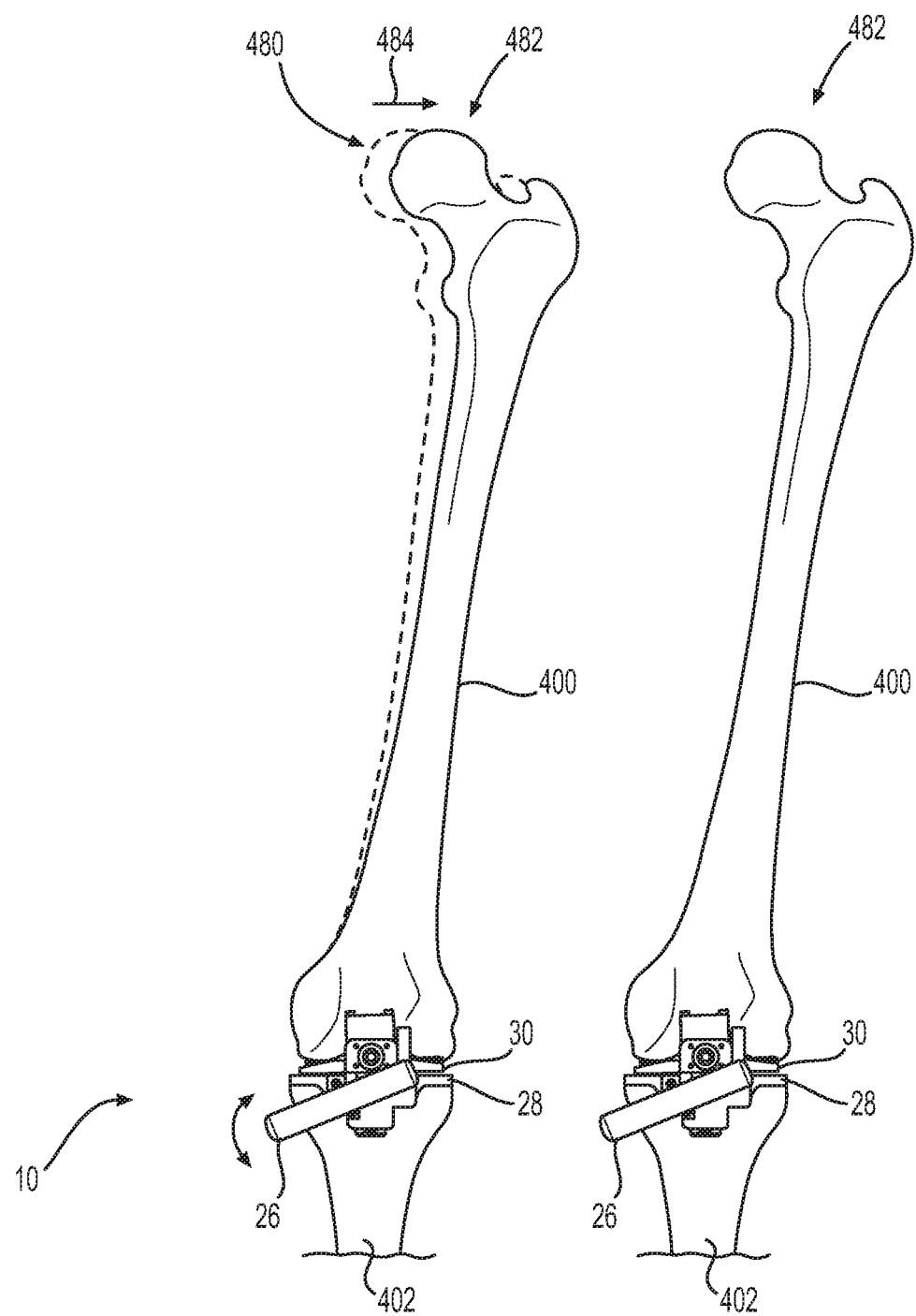
FIG. 32 illustrates an equalizing step where the M-L angle of the moving support structure is adjusted in accordance with an example embodiment.

FIG. 32 illustrates an equalizing step where the M-L angle of moving support structure 30 is adjusted in accordance with an example embodiment. As mentioned previously, distractor 10 is locked such that moving support structure 30 cannot increase or decrease the distraction distance. Also, moving support structure 30 had been allowed to freely rotate medially or laterally. In one embodiment, the M-L tilt mechanism of distractor 10 can be engaged to moving support structure 30 and is self-locking when changing a M-L tilt angle. A key, handle, or knob is coupled to the M-L tilt mechanism to change the M-L tilt angle of moving support structure 30. In one embodiment, the key is rotated to adjust the M-L tilt mechanism. Initially, as indicated in FIG. 30, the M-L tilt angle of moving support structure 30 is −4.9 degrees. Femur 400 with the M-L tilt angle of −4.9 degrees corresponds to a position 480. The key is rotated to adjust the M-L tilt mechanism thereby changing the M-L tilt angle from −4.9 degrees to zero degrees. Changing the M-L tilt angle rotates the femur 400 as indicated by arrow 484 until a position 482 is reached. The position 482 is shown without any further movement in FIG. 32 where the M-L tilt angle measured by distractor 10 is zero degrees. It should be noted that the loading on the medial and lateral side of cover 38 of FIG. 29 can change as well as the position of loading on the medial and lateral side.

FIG. 33 illustrates a step of monitoring equalization of femur 400 of FIG. 32 on display 14 in accordance of an example embodiment. In one embodiment, the surgeon can monitor display 14 as the key is rotated on the M-L tilt mechanism. The surgeon rotates the key until M-L tilt angle is zero. This also corresponds to the condition where the plane of fixed support structure 28 of FIG. 32 and the plane of moving support structure 30 are parallel to one another. Note that the average distraction distance as indicated in box 436 does not change. The medial gap as indicated in box 452 and the lateral gap as indicated by box 454 does change because the M-L tilt has changed to zero. The medial gap indicated in box 452 reads 12.9 millimeters and the lateral gap indicated in box 454 reads 13.2. Referring briefly to FIG. 31, the step of equalizing moves the center of the femoral head 472 medially as shown in FIG. 32. Note on FIG. 31 that moving the center of the femoral head 427 medially reduces the offset angle formed by lines 470 and 474 thereby placing the leg in better alignment. In general, the step of equalizing eliminates or reduces the offset of the femur 400 to an acceptable alignment based on clinical evidence.

Figure 34:
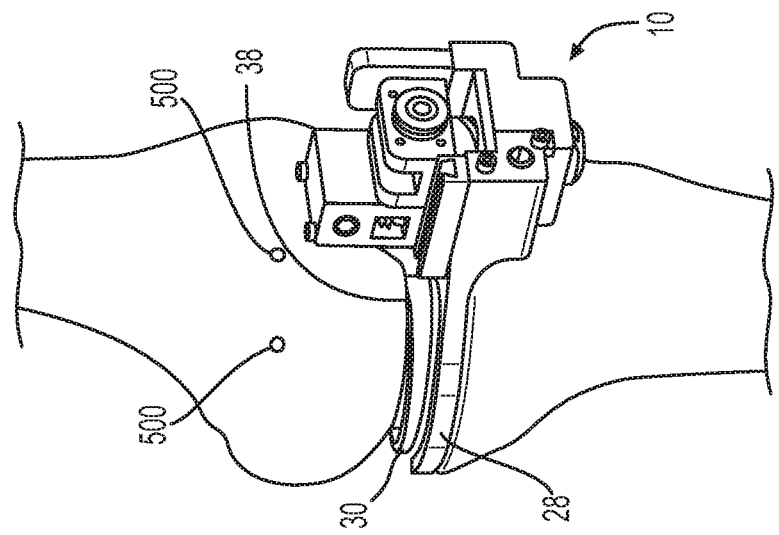
FIG. 34 illustrates a step of drilling guide holes in the femur in accordance with an example embodiment.

FIG. 34 illustrates a step of drilling guide holes in femur 400 in accordance with an example embodiment. As disclosed in FIG. 32 and FIG. 33, distractor 10 the height of the medial compartment and the height of the lateral compartment have been made equal. Equalizing the medial and lateral compartment heights eliminates or reduces the femoral offset relative to the mechanical axis of the leg such that the leg is in alignment. Moving support structure 30 has been locked to prevent movement or change of the distraction distance. The medial compartment height and the lateral compartment height having an M-L tilt angle of zero is also locked in place. In one embodiment, the M-L tilt mechanism is self-locking. The knob coupled to the M-L tilt mechanism has been removed so the M-L tilt angle cannot be changed. Adjustments to change the applied loading to the medial or lateral surface of cover 38 are performed prior to drilling guide holes. For example, soft tissue release can be performed to adjust the load values.

Femur 400 is in alignment with the mechanical axis having the height of the medial compartment equal to the height of the lateral compartment. The load and position of load on the medial side and the lateral side of cover 38 have been quantitatively measured and verified within acceptable predetermined ranges for the prosthetic knee joint system. The measured distraction height relates to a thickness of an installed final tibial prosthetic component, a final insert, and a final femoral prosthetic component. Thus, femur 400 guide pin holes can be drilled to align and support a resection guide for the distal end of femur 400. A drill guide holder 490 is coupled to distractor 10. A drill guide 492 couples to drill guide holder 490. Drill guide holder 490 aligns and retains drill guide 492 adjacent to the distal end of femur 400. Drill guide 492 includes one or more openings 496 that receive a drill bit 494 to drill openings in the distal end of femur 400.

Figure 35:
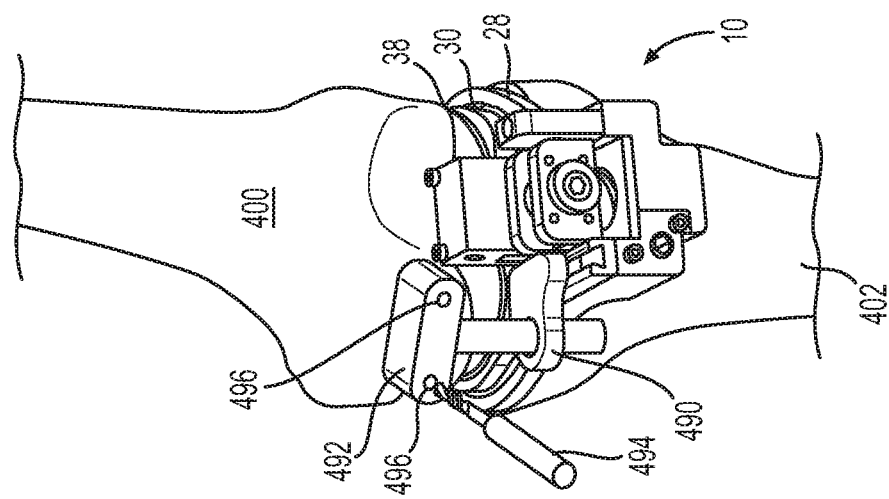
FIG. 35 illustrates a step of removing a drill guide and drill guide holder from the distractor in accordance with an example embodiment.

FIG. 35 illustrates a step of removing drill guide 492 and drill guide holder 490 of FIG. 34 from distractor 10 in accordance with an example embodiment. Holes 500 are drilled using drill guide holder 490 and drill guide 492 coupled to distractor 10 as shown in FIG. 34. Holes 500 will subsequently be used to couple a resection guide to femur 500 and make one or more cuts for fitting a femoral prosthetic component to the distal end of femur 400.

FIG. 36 illustrates a step of reducing the distraction distance of distractor 10 and placing the leg in flexion in accordance with an example embodiment. The M-L tilt mechanism is released allowing moving support structure 30 to freely swing medially or laterally. Distractor 10 is adjusted to a minimum distraction distance. In one embodiment, the minimum distraction distance occurs when both fixed support structure 28 and moving support structure 30 couple to the prepared surface at the proximal end of tibia 402. As mentioned previously, the plane of fixed support structure 28 corresponds to zero degrees M-L tilt. In one embodiment, the minimum distraction distance is 6.8 millimeters. The leg can be placed in flexion where tibia 402 and femur 400 form a 90 degree angle. In one embodiment, module 32 includes an inertial sensor configured to measure the angle between femur 400 and tibia 402. The inertial sensor data is transmitted to the computer and can be displayed on display 14.

Display 14 is shown with tilt meter 420 and bar graph 430. Tilt meter 420 indicates an M-L tilt angle of zero degrees. Since moving support structure 30 can swing freely medially or laterally it couples to the prepared surface of tibia 402 with fixed support structure 28. Thus, both are coupled to the same plane and the M-L tilt angle is zero degrees. The M-L tilt mechanism was enabled in FIG. 32 and adjusted to equalize the medial and lateral gap such that the M-L tilt angle is zero. The M-L tilt angle of 0.0 degrees is indicated in box 424. The bar graph 430 indicates a minimum distraction distance on bar 432. The minimum distraction distance of 6.8 millimeters is shown in box 436.

Figure 37:
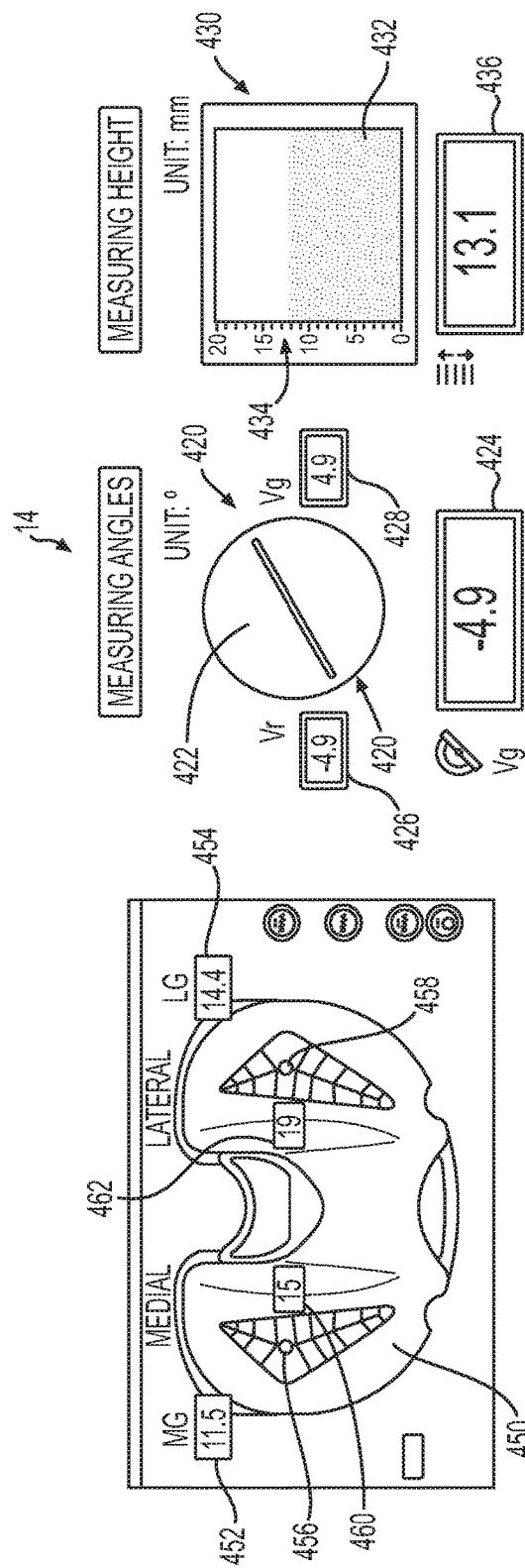
FIG. 37 illustrates a step of adjusting the distraction distance while the leg is in flexion in accordance with an example embodiment.

FIG. 37 illustrates a step of adjusting the distraction distance while the leg is in flexion in accordance with an example embodiment. The step of adjusting the distraction distance is similar to when the leg was in extension. Distractor 10 of FIG. 36 is adjusted to increase the distraction distance from the minimum distraction distance. The loading on the medial and lateral sides of cover 38 of FIG. 36 will increase as the distraction distance increases. In one embodiment, the surgeon is viewing the load magnitude on display 14 as the distraction distance is increased. This is indicated in box 460 and box 462 on display 14 showing the position of load on the medial and lateral surface of cover 38. The distraction distance is increased until the loading on cover 38 reaches a predetermined value. Note that the values on the medial and lateral sides of cover 38 are not equal under flexion but the maximum load value corresponds to the desired predetermined value.

The moving support structure of FIG. 36 was released from the M-L tilt mechanism to allow it to freely swing medially or laterally when in flexion. M-L tilt meter 420 indicates the M-L tilt angle and the value is displayed in box 424 as −4.9 degrees. The distraction distance is also displayed in bar graph 430 and the value of 13.1 millimeters is displayed in box 436. The distraction distance is an average distance. The height of the medial compartment and the height of the lateral compartment is calculated by computer 12 of FIG. 1 using the measurement data such as the M-L tilt angle, the position of load, and distraction distance. The height of the medial compartment is measured as 11.5 millimeters as shown in box 452 of display 14. The height of the lateral compartment is measured as 14.4 millimeters as shown in box 454 of display 14. The measurement data listed herein above can be stored in memory of computer 12 shown in FIG. 1.

Figure 38:
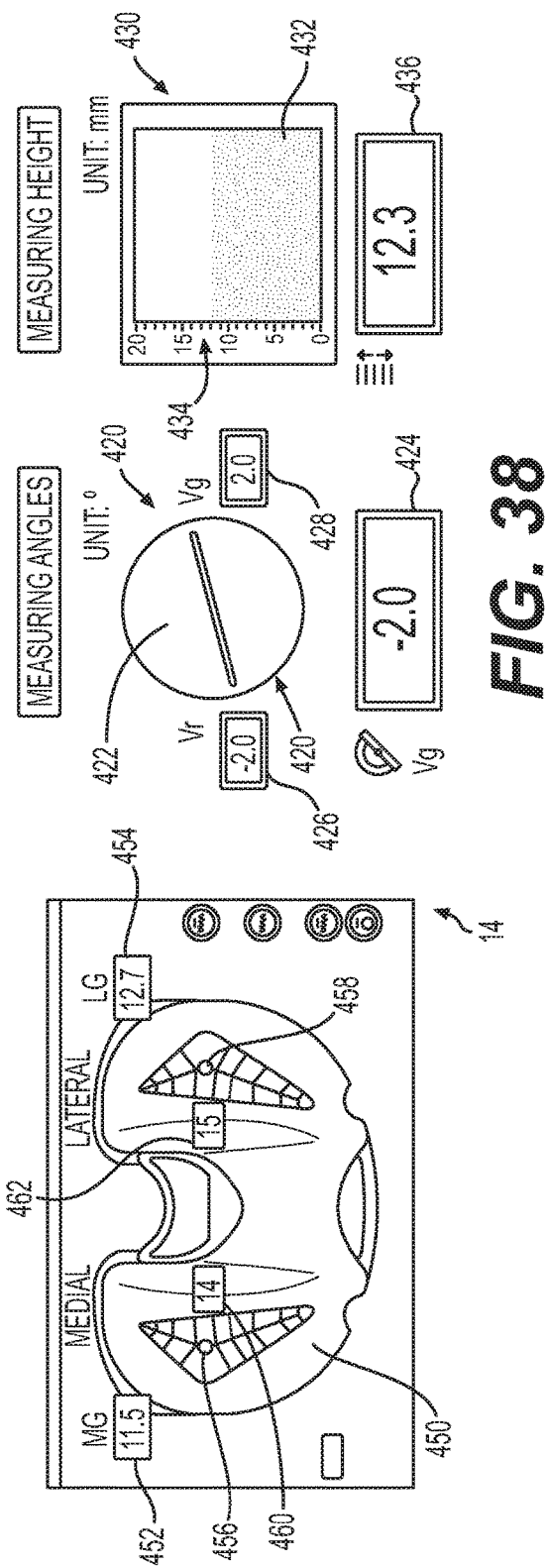
FIG. 38 illustrates a step of equalizing the medial gap and the lateral gap with the leg in flexion in accordance with an example embodiment.

FIG. 38 illustrates a step of equalizing the height of the medial compartment and the height of the lateral compartment with the leg in flexion in accordance with an example embodiment. The distraction mechanism is locked to prevent movement of moving support structure 30 of FIG. 36. The M-L tilt mechanism is engaged to adjust the M-L tilt angle of moving support structure 30. As mentioned previously, M-L tilt mechanism is self-locking. The M-L tilt angle is adjusted to equalize the M-L tilt angle to zero degrees with the leg in flexion. Adjusting the M-L tilt angle to zero degrees equalizes the height of the medial and lateral compartments with the leg in flexion. Similar to FIG. 31 an offset of the leg alignment in flexion is reduced when the medial gap and the lateral gap equalized. The loading on the medial and lateral sides of cover 38 is viewed on display 14 and adjusted if the loading is too high or the balance is significantly off. Typically, soft tissue release is used to adjust the loading and balance.

After adjustments have been made under equalized conditions the distraction mechanism lock is released and the M-L tilt mechanism is disengaged to allow moving support structure 30 to freely rotate medially and laterally. Measurement data should indicate that the medial and lateral gap are closer than was previously measured in flexion. The measurement data should also indicate the medial and lateral sides are in better balance and the load magnitude is within a predetermined range that supports performance and reliability of the knee joint. In the example, the medial gap is listed in box 452 as 11.5 millimeters. The lateral gap is listed in box 454 as 12.7 millimeters. The difference between the applied load between the medial and lateral sides is 1 lb and the highest load magnitude is 15 lbs on the lateral side of cover 38. The difference in the gap height between the knee joint in extension and the knee joint in flexion can be due to knee geometry or position of applied load on cover 38. The gap data, load data, balance data, and M-L tilt angle is stored in memory on computer 12 as shown in FIG. 1. It should be noted that the values disclosed herein above for the knee in extension and flexion can vary significantly from the data disclosed and is only used as an example.

Figure 39:
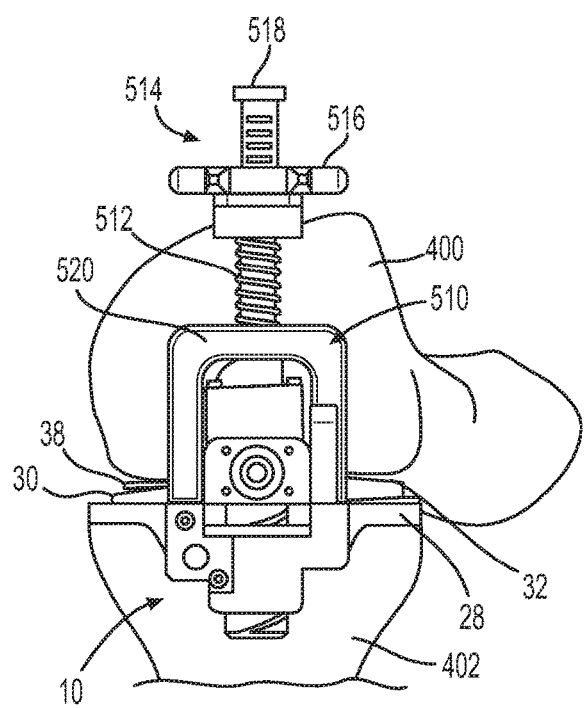
FIG. 39 illustrates a step of placing a sizer on the distractor to support selection of a femoral prosthetic component in accordance with an example embodiment.

FIG. 39 illustrates a step of placing a sizer 510 on distractor 10 to support selection of a femoral prosthetic component in accordance with an example embodiment. Selecting a correct size for the femoral prosthetic component minimizes overhang of the femoral prosthetic component, minimizes bone resection, and maximize coverage using algorithms to determine an optimal installation for different models of the femoral prosthetic component. Previously, the leg was equalized and adjusted in flexion using quantitative measurement information from module 32 and distractor 10 as shown in FIG. 36. A sizer 510 is configured to couple to distractor 10 with the leg in flexion. In the example embodiment, tibia 402 is at approximately a 90 degree angle to femur 400. The exact angle can be quantitatively measured with an inertial sensor in module 32. Sizer 510 comprises a fork 520, a femur coupler, a threaded cylinder 518, a spring 512, a knob 516, and a scale 514. Fork 520 includes one or more retaining features that align and retain fork 520 to distractor 10. Threaded cylinder 518 extends from fork 520 above femur 400 in flexion. Spring 512 overlies threaded cylinder 518 and is supported by fork 520. The femur coupler couples to the threaded cylinder 518 and femur 400. In one embodiment, threaded cylinder 518 couples through an opening of the femur coupler such that a portion of the femur coupler is supported by spring 512. The femur coupler also couples to a location on femur 400. Knob 516 threads onto threaded cylinder 518 and couples to the femur coupler. Spring 512 provides resistance against the femur coupler and knob 516. Scale 514 is formed on threaded cylinder 518 and is visible above a top surface of knob 516. Scale 514 is used to select a femoral prosthetic component size.

Figure 40:
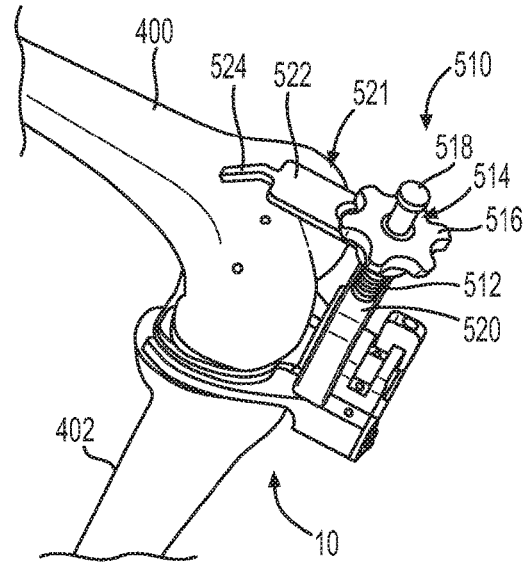
FIG. 40 illustrates a step of coupling a femur coupler to the femur with the leg in flexion in accordance with an example embodiment.

FIG. 40 illustrates a step of coupling a femur coupler 521 to femur 400 with the leg in flexion in accordance with an example embodiment. Femur coupler 521 comprises a body 522 and an extension 524. Body 522 extends femur coupler 521 from threaded cylinder 518 over femur 400. Extension 524 extends from body 522 and couples to femur 400. In one embodiment, extension 524 includes at least one bend that supports coupling to femur 400 without body 522 coupling to femur 400. Extension 524 can couple to a predetermined location on femur 400 or a bone landmark of femur 400. As mentioned previously scale 514 can be read above a surface of knob 514 to support selection of the femoral prosthetic component.

Figure 41:
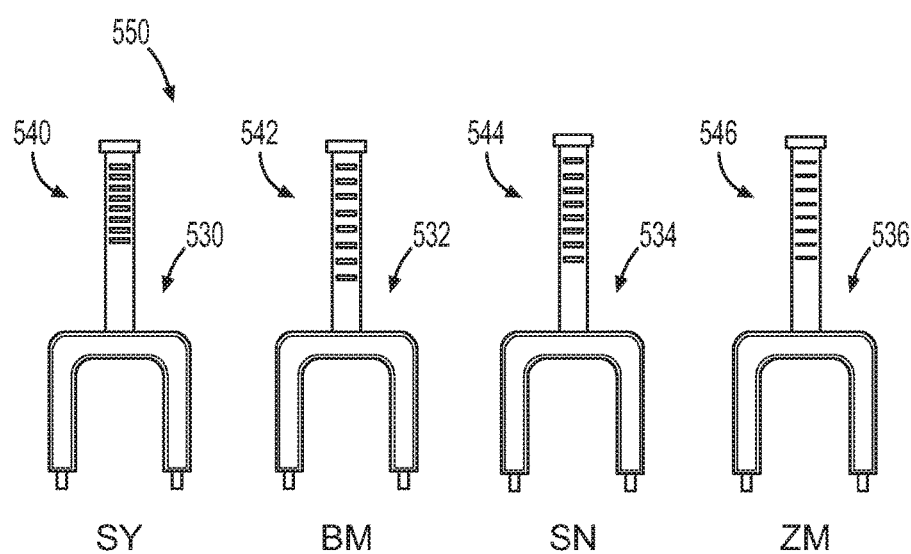
FIG. 41 illustrates a step of providing a plurality of sizers to support selection of the femoral prosthetic component.

FIG. 41 illustrates a step of providing a plurality of sizers 550 to support selection of the femoral prosthetic component. In one embodiment, four different sizers are provided to select the femoral prosthetic component that best fits the knee joint. A sizer 530 is labeled SY and includes a scale 540. A sizer 532 is labeled BM and includes a scale 542. A sizer 534 is labeled SN and includes a scale 544. A sizer 536 is labeled ZM and includes a scale 546. The scales 540, 542, 544, and 546 are all different and support selection of the femoral prosthetic component. Sizers 530, 532, 534, and 536 can have one or more drill guide holes configured to support drilling holes in the distal end of the femur 400.

Figure 42:
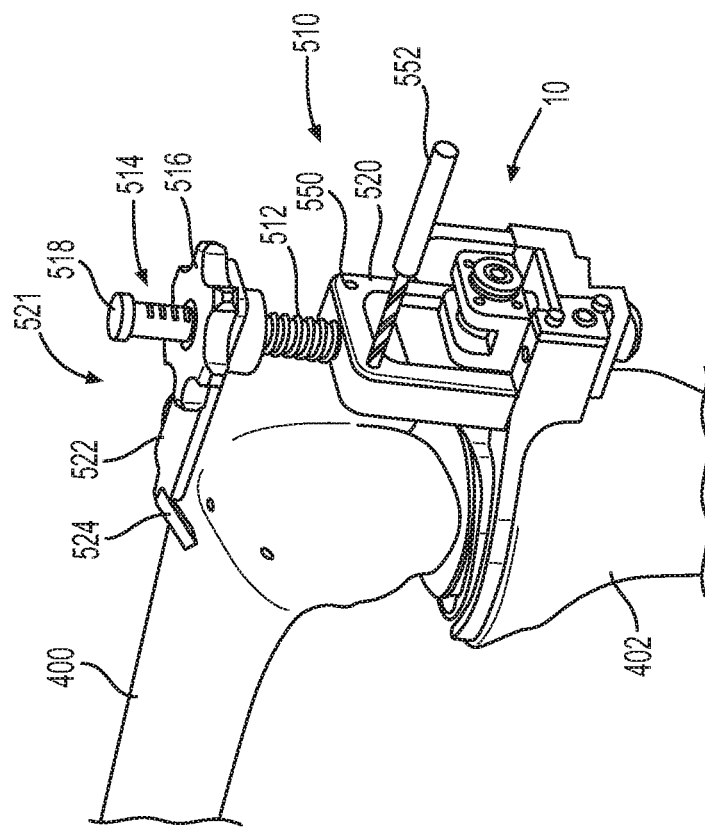
FIG. 42 illustrates a step of drilling one or more holes in the distal end of the femur in flexion in accordance with an example embodiment.

FIG. 42 illustrates a step of drilling one or more holes in the distal end of femur 400 in flexion in accordance with an example embodiment. The one or more holes will be used to align or support a cutting guide configured to prepare a surface of the femur 400. The leg is in flexion having femur 400 and tibia 402 at approximately a 90 degree angle. Distractor 10 has been used to equalize the knee joint, align the leg, and the load magnitudes have been adjusted if needed. A sizer 510 has been selected as providing the best fit for femur 400. Sizer 510 has one or more drill guides 550 for receiving a drill bit 552 to drill femur 400. A drill using drill bit 552 is used to drill a hole in femur 400 using drill guide 550.

Figure 43:
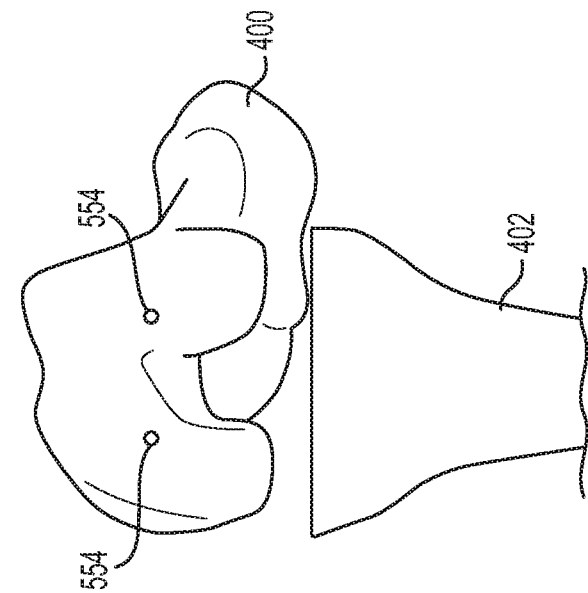
FIG. 43 illustrates one or more holes drilled in the distal end of the femur in accordance with an example embodiment.

FIG. 43 illustrates one or more holes drilled in the distal end of the femur in accordance with an example embodiment. Holes 554 are drilled in the distal end of the femur to support the cutting guide for preparing a bone surface of the femur 400 for receiving the femoral prosthetic component. Distractor 10 and sizer 510 of FIG. 42 were used to drill holes 554 at predetermined locations. The distractor 10 is removed from the knee joint.

Bone surfaces of the distal end of femur 400 are prepared and the femoral prosthetic component is installed. Similarly, the tibial prosthetic component can be installed. Module 32 can be installed in an insert 308 as disclosed in FIG. 24 and FIG. 25. Insert 308 can be installed in the knee joint such that insert 308 is coupled to and retained by the tibial prosthetic component. The knee joint can be moved through a range of motion for the surgeon to gain subjective feedback on the knee joint installation. Module 32 will send quantitative measurement data to the computer 12 as shown in FIG. 1 for further evaluation. In general, module 32 should provide similar measurement data as generated in flexion and extension using distractor 10. In one embodiment, computer 12 checks the measurement data from insert 308 and compare it to the previously measured data using distractor 10. Thus, module 32 and insert 308 can be used to verify proper installation of the knee joint. Moreover, fine adjustments can be made to further improve the joint installation prior to finalizing the installation. The insert 308 is then removed and a final insert equal in size is inserted to complete the knee joint installation.

FIG. 44 is an illustration of a distractor 1000 in accordance with an example embodiment. Referring briefly to FIG. 1 distractor 10 is configured to distract a knee joint, transmit measurement data to a remote system such as a computer 12, and display the measurement data in real-time on display 14 in an operating room. Distractor 1000 is an alternate embodiment of distractor 10. Distractor 1000 can be used similarly to distractor 10 as disclosed herein above. Distractor 1000 can include one or more sensors to measure distraction height, medial-lateral angle, load magnitude applied by the musculoskeletal system to the distractor, leg position, support one or more bone cuts, support alignment, and measure position of load applied to the medial and lateral surfaces of the distractor.

Referring back to FIG. 44, the distractor 1000 comprises a housing 600, a fixed plate 602, lateral plate 604 (for a knee joint of a left leg), a medial plate 606 (for the knee joint of the left leg), a lateral brake 608, a medial brake 610, a knob 616, a lateral height scale 614, and a medial height scale 612. Knob 616 is used to raise and lower lateral plate 604 and medial plate 606 in relation to fixed plate 602. Fixed plate 602 couples to a prepared surface of a tibia. In one embodiment, knob 616 is rotated counter clockwise or clockwise to raise or lower plates 604 and 606. The amount of lateral distraction and medial distraction can be respectively read off of lateral scale 614 and medial scale 612 on housing 600. One or more magnetic height sensors can be used to measure the lateral and medial distraction heights as disclosed herein above. The electronic circuitry as disclosed in FIG. 15 is coupled to the one or more magnetic height sensors and placed within housing 600 to control a measurement process and transmit the height data to be displayed on a display within the operating room. Distractor 1000 can be used in a knee joint of the right leg with the knowledge that the medial and lateral sides of distractor 1000 are transposed. Alternatively, a second distractor could be provided for a right leg. Note that distractor 1000 has plates 604 and 606 offset. The offset supports placement of the patella on a lateral side of the knee joint and allows the patella to be placed back on the knee joint after distractor 1000 is inserted. The patella loads the knee joint which is taken into account in all the measurement data and subsequent steps taken prior to the knee joint installation. The second or right leg distractor provided with distractor 1000 would have an opposite offset to support placement of the patella laterally on the right knee joint prior to installation of the second distractor.

Distractor 1000 is configured to distract, equalize, and support alignment of a leg to the mechanical axis of the leg by one or more bone cuts to the femur. The bone cuts to a distal end of the femur support installation of a femoral prosthetic component that aligns the femur and tibia to the mechanical axis. Distractor 1000 is used to drill guide holes for a cutting jig with the leg in extension and flexion. The cutting jig is then coupled to the distal end using the guide holes and the bone cuts are made. In general, distractor 1000 is configured to generate an offset on the prepared surfaces of the distal end of the femur that reduces or eliminates a varus or vargus leg deformity that supports an installation of a prosthetic knee joint in alignment to the mechanical axis of the leg.

FIG. 45 is an illustration of the distractor 1000 with a transparent housing to illustrate components therein in accordance with an example embodiment. Knob 616 is configured to rotate to raise and lower slide block 620. In one embodiment, a threaded shaft extends from knob 616. The threaded shaft is aligned and retained by a structure 626 formed in housing 600. In one embodiment, structure 626 can have an opening with a bearing surface. The threaded shaft can have a region that is not threaded that couples to the bearing surface of structure 626 to support alignment of the threaded shaft within housing 600 and rotation of the threaded shaft. Alternatively, structure 626 can have a threaded opening for receiving the threaded shaft. Slide block 620 includes a threaded opening configured for receiving the threaded shaft coupled to knob 616. In one embodiment, slide block 620 is not fastened to housing 600 whereas structure 626 is attached or integrated as part of housing 600. Thus, rotating knob 616 can raise or lower slide block 620 in relation to structure 626 but only slide block 620 can move in relation to housing 600.

Slide block 620 is housed within housing 600 and includes a free wheel gear 618. In one embodiment, free wheel gear 618 is located at a proximal end of slide block 620 and configured to rotate. A post 622 extends from lateral plate 604 and is configured to move parallel to slide block 620 and the threaded shaft. Post 624 has gear teeth engaging with free wheel gear 618. Similarly, a post 624 extends from medial plate 606 and is configured to move parallel to slide block 620 and the threaded shaft. Post 622 has gear teeth engaging with free wheel gear 618. Posts 622 and 624 extend through openings in a proximal end of housing 600 into an interior of the housing. Housing 600 aligns, retains, and supports movement of lateral plate 606 and medial plate 604. In one embodiment, grooves are formed in posts 622 and 624. Housing 600 has corresponding tongues 628 that fit within the grooves that align and retain post 622 and post 624 to the housing. Tongues 628 extending from an interior surface of housing 600 are received within the grooves of posts 622 and 624 and are configured to support movement parallel to the threaded shaft and slide block 620.

In the illustration, knob 616 cannot be rotated clockwise as slide block 620 contacts structure 626 whereby no gap exists to allow further rotation or the threaded shaft. In this position, lateral plate 606 and medial plate 604 are in a minimum height position corresponding to lateral plate 606 and medial plate 604 contacting fixed plate 602. Fixed plate 602 is coupled to housing 600. In one embodiment, fixed plate 602 extends from housing 600 and is molded or machined as part of housing 602. Fixed plate 602 can be at a 90 degree angle relative to the movement of post 622, post 624, slide block 620, and the threaded shaft.

Brakes 608 and 610 respectively prevent movement of post 622 and post 624. In one embodiment, brakes 608 and 610 are friction brakes. Brakes 608 or 610 can include a threaded shaft 632. The threaded shaft 632 of brakes 608 or 610 couples through a threaded opening 630 formed in housing 600. Rotating threaded shaft 632 in opening 630 clockwise or counter clockwise can respectively increase or decrease the depth of threaded shaft 632 within housing 600. In one embodiment, threaded shaft 632 of brake 608 contacts and applies pressure to post 622 as brake 608 is rotated clockwise. The pressure applied to post 622 presses tongues 628 against the corresponding grooves on post 622. The friction created between tongues 628 and post 622 by brake 608 prevents movement of post 622 and thereby lateral plate 604. Similarly, threaded shaft 632 of brake 610 can be rotated to contact and apply pressure to post 624 as brake 610 is rotated clockwise. The pressure applied to post 624 presses tongues 628 against the corresponding grooves on post 624. The friction created between tongues 628 and post 624 by brake 610 prevents movement of post 624 and thereby medial plate 606. Conversely, rotating brakes 608 and 610 counter-clockwise where brakes 608 and 610 do not respectively contact posts 622 and 624 allows posts 622 and 624 to move without friction.

Figure 46:
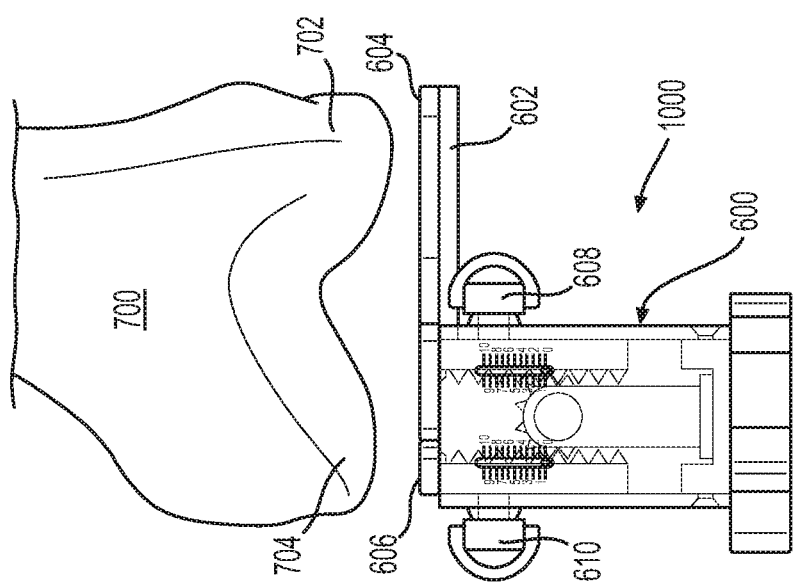
FIG. 46 illustrates a step in a knee joint installation procedure related to the alternate embodiment of the distractor shown in FIG. 44 in accordance with an example embodiment.

FIG. 46 illustrates a step in a knee joint installation procedure related to distractor 1000 shown in FIG. 44 in accordance with an example embodiment. The listing of the steps herein below does not imply any order or sequence. Distractor 1000 is placed in the knee joint similar to that shown in FIG. 1. A proximal end of the tibia has a prepared surface and the leg is positioned in extension. The fixed position plate 602 couples to the prepared surface of tibia. The proximal end of tibia can be cut perpendicular to the tibia anatomical axis using an alignment jig. The resection of tibia can also include an anterior-posterior (A-P) slope.

A computer receives transmitted measurement data from distractor 1000. Referring back to FIG. 46 load sensors (not shown) can be embedded in medial plate 606 and lateral plate 604 to support measurement of a load magnitude and position of load applied to plates 604 and 606. Alternatively, the load sensors can comprise a module that rests on a surface of medial plate 604 or lateral plate 606. Distractor 1000 can also include one or more magnetic sensors configured to measure a distraction distance between lateral plate 604 and fixed plate 602 as disclosed herein above. The one or more magnetic sensors can also be configured to measure a distraction distance between medial plate 606 and fixed position plate 602. The distraction distance data and the load measurement data is transmitted to the computer for further processing. In one embodiment, the load sensors and the one or more magnetic height sensors couple to electronic circuitry such as shown in FIG. 15. The electronic circuitry of FIG. 15 is configured to control a measurement process and transmit measurement. The electronic circuitry and the one or more magnetic height sensors can be housed in housing 600 of distractor 1000. The load measurement data received by the computer can be used to calculate the load magnitude and the position of load applied to lateral plate 604 and medial plate 606. The load magnitude and the position of load can be displayed on a display coupled to the computer in real-time to the surgeon in the operating room. Similarly, the distraction height measurement data related to the lateral plate 604 and the medial plate 606 received by the computer can be displayed on the display. The distraction height measurement data can also be used to calculate a medial-lateral slope between lateral plate 604 and medial plate 606. The slope would correspond to a line through contact point (e.g. position of load) on the lateral plate 604 and the medial plate 606.

In the illustration, distractor 1000 is placed in the knee joint. The natural femur 700 is shown having a medial condyle 704 and a lateral condyle 702 respectively overlying the lateral plate 604 and the medial plate 606. Distractor 1000 is inserted in a minimum distraction height. As mentioned previously, the minimum distraction height corresponds to the lateral plate 604 and the medial plate 606 coupling to the fixed position plate 602. Brakes 608 and 610 are not enabled for respectively preventing movement of lateral plate 604 and medial plate 606.

Figure 47:
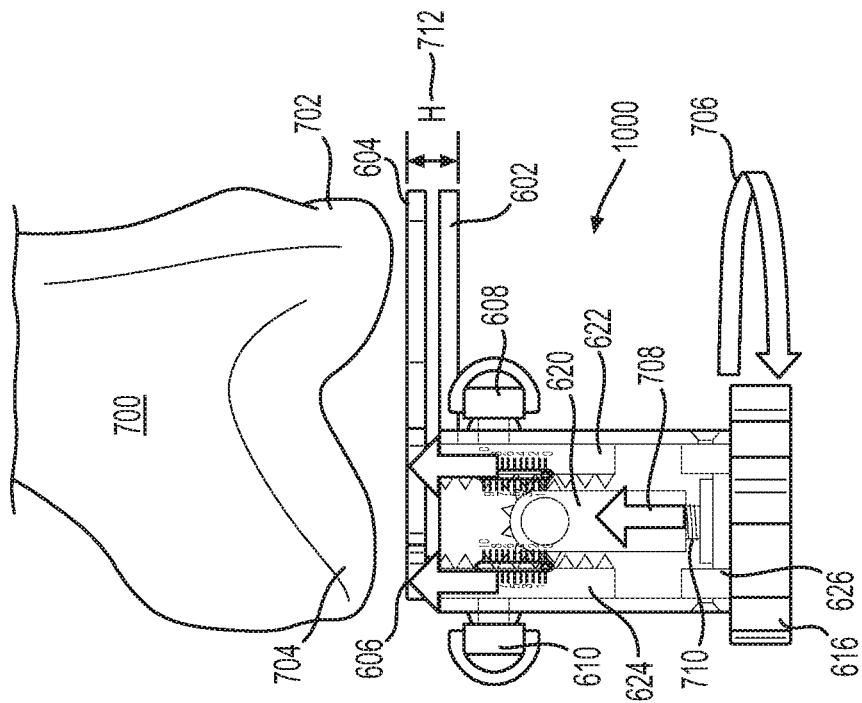
FIG. 47 illustrates a step in the knee joint installation procedure related to the alternate embodiment of the distractor wherein the knob is rotated counter clockwise in accordance with an example embodiment.

FIG. 47 illustrates a step in the knee joint installation procedure related to distractor 1000 wherein knob 616 is rotated counter clockwise in accordance with an example embodiment. The direction of rotation of knob 616 is indicated by arrow 706. Rotating knob 616 counter clockwise rotates threaded shaft 710 such that slide block 620 moves away from structure 626. In the example, lateral plate 604 and medial plate 606 are unloaded and posts 622 and 624 are free to move. Slide block 620 moves in a direction indicated by arrow 708. In the unloaded state, slide block 620 moves both lateral plate 606 and medial plate 604 equally in the direction indicated by arrow 708. A distraction height corresponds to the separation between lateral plate 604 or medial plate 606 and fixed position plate 602. The distraction height is indicated by double sided arrow 712 and is labeled H. As mentioned, medial plate 606 is raised simultaneously with lateral plate 604 and by an equal amount from fixed position plate 602. The distraction data from magnetic distance sensor can be transmitted to the computer and the distraction distance H can be displayed on the display of the computer within the operating room to review the distraction distance in real-time. Note that the lateral condyle 702 and the medial condyle 704 are not in contact with lateral plate 604 or medial plate 606.

Figure 48:
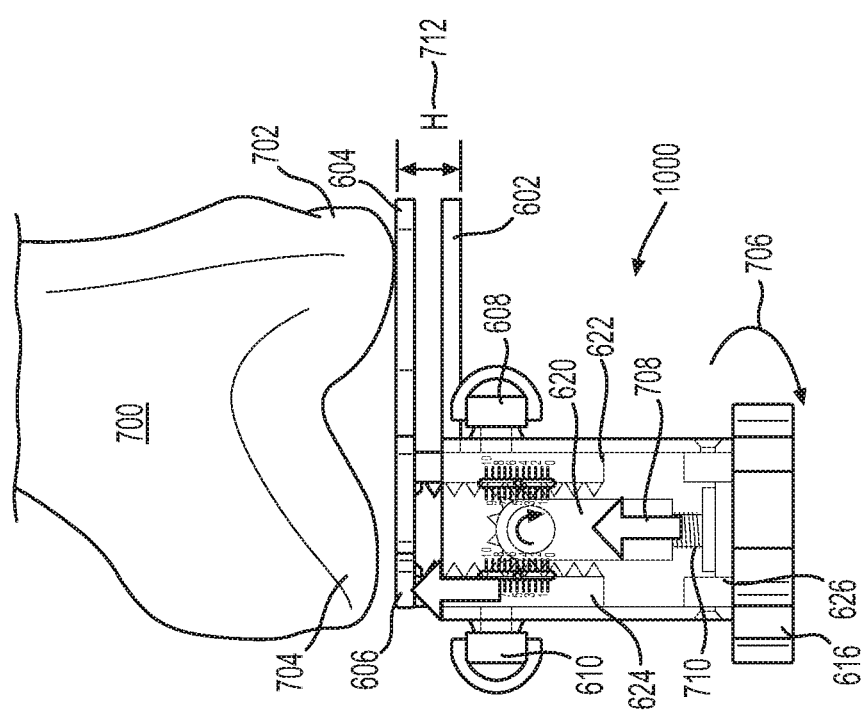
FIG. 48 illustrates a step in the knee joint installation procedure related to the alternate embodiment of the distractor coupling to the femur in accordance with an example embodiment.

FIG. 48 illustrates a step in the knee joint installation procedure related to distractor 1000 coupling to femur 700 in accordance with an example embodiment. As mentioned previously, fixed position plate 602 rests against a prepared surface of a tibia (not shown). Brakes 608 and 610 are not enabled thereby allowing posts 622 and 624 to move freely. Knob 616 rotates threaded shaft 710 counter clockwise to increase a gap between slide block 620 and structure 624 as indicated by arrow 708. Slide block 620, post 622, and post 624 are motivated by threaded shaft 710 to raise lateral plate 604 and medial plate 606 thereby increasing a distraction height as indicated by double sided arrow 712. Lateral plate 604 and medial plate 606 move simultaneously and by the same amount. In the example, lateral condyle 702 contacts lateral plate 604. In one embodiment, load sensors coupled to lateral plate 604 would register a measureable load as lateral condyle 702 couples to lateral plate 604. The load measurement data can be displayed on the display coupled to the computer receiving the load measurement data. Note that medial plate 606 is not in contact with medial condyle 704. In one embodiment, the counter clockwise rotation of knob 616 continues until a predetermined load magnitude is reached applied by lateral condyle 702 to lateral plate 604. As mentioned, the change in load magnitude can be viewed on the display in real-time. Typically, the predetermined load magnitude can be within a predetermined load magnitude range that has been clinically proven to provide performance, reliability, and longevity of the prosthetic knee joint.

Figure 49:
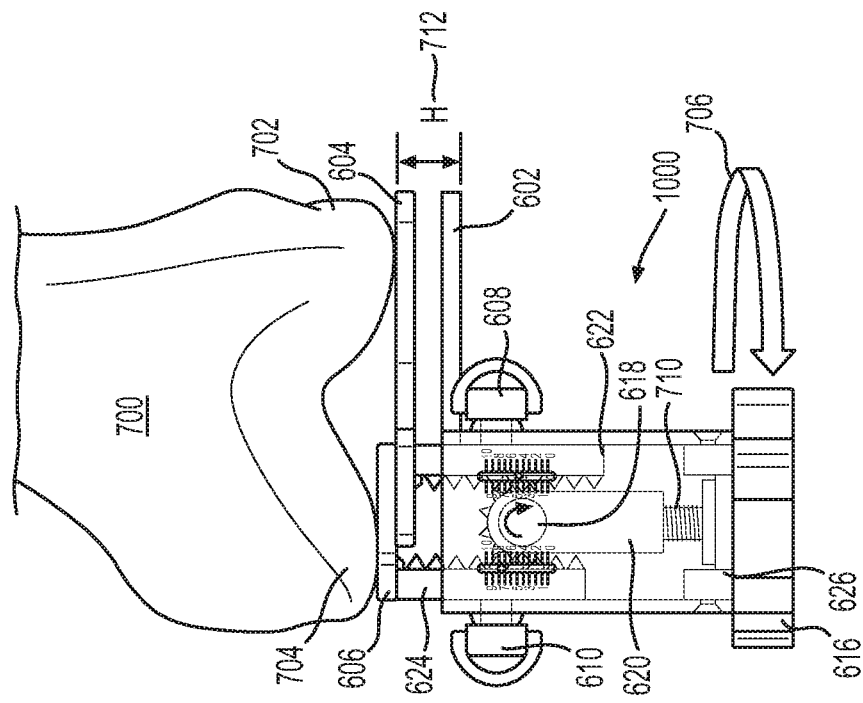
FIG. 49 illustrates the step in a knee joint installation procedure related to the alternate embodiment of the distractor where the lateral plate and the medial plate contact the femur in accordance with an example embodiment.

FIG. 49 illustrates the step in a knee joint installation procedure related to distractor 1000 where lateral plate 604 and medial plate 606 contact femur 700 in accordance with an example embodiment. As previously stated, the lateral plate 604 is in contact with lateral condyle 702 and distracted to a predetermined load magnitude. The lateral plate 604 measuring the predetermined load magnitude also corresponds to a predetermined distraction distance. Brake 608 is rotated clockwise to contact post 622 to prevent any further movement of lateral plate 604. Brake 610 is not enabled and post 624 is free to move as slide block 620 moves.

Knob 616 is rotated counter clockwise to increase the gap between slide block 620 and structure 626. Brake 608 prevents post 622 from moving but free wheel gear 618 rotates clockwise as threaded shaft 710 is rotated counter clockwise. Free wheel gear 618 engages with the gear teeth of post 624 as it rotates clockwise. The clockwise rotation of free wheel gear 618 increases the distraction distance between medial plate 606 and fixed position plate 602. Thus, lateral plate 604 does not move while the distraction distance between medial plate 606 and fixed position plate 602 increases until medial plate 606 contacts medial condyle 704 of femur 700. Similar to lateral plate 604, load sensors coupled to medial plate 606 would register a measureable load as medial condyle 704 contacts medial plate 606. Loading and position of load on medial plate 606 is displayed on the display coupled to the computer receiving the load measurement data. In one embodiment, knob 616 is rotated counter clockwise to increase the load magnitude applied to medial plate 606 until it is equal to the load magnitude applied to lateral plate 604 (e.g. the predetermined load magnitude). Thus, the tension of medial collateral ligament is the same as the lateral collateral ligament.

Figure 50:
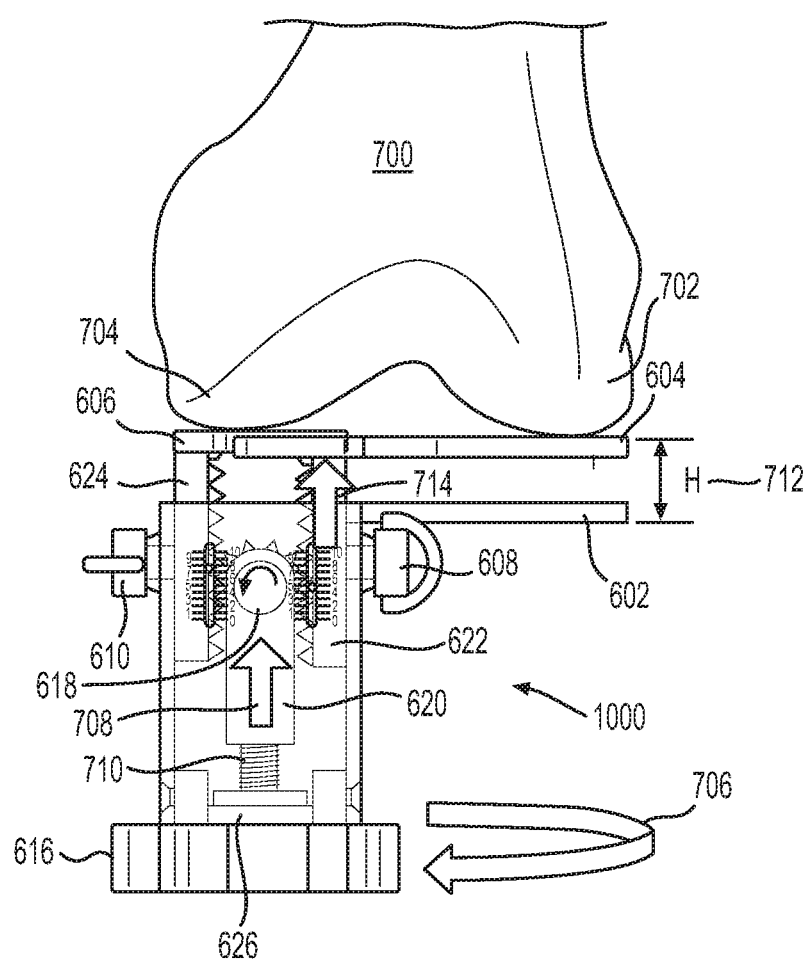
FIG. 50 illustrates a step in the knee joint installation procedure related to the alternate embodiment of the distractor where equalization of the medial gap and the lateral gap occurs in accordance with an example embodiment.

FIG. 50 illustrates a step in the knee joint installation procedure related to distractor 1000 where equalization of the medial gap and the lateral gap occurs in accordance with an example embodiment. In general, the medial gap is the distraction distance in the medial compartment of the knee joint. Similarly, the lateral gap is the distraction distance in lateral compartment of the knee joint. Referring briefly to FIG. 49, the medial gap is larger than the lateral gap but both are set such that the tension of the medial collateral ligament is the same as the lateral collateral ligament.

Referring back to FIG. 50, brake 610 is enabled to prevent movement of post 624. Conversely, brake 608 is released whereby post 622 can move freely to increase or decrease the distraction distance between lateral plate 604 and fixed position plate 602. In the example, the lateral gap is smaller than the medial gap. Thus, a process of equalizing the medial and lateral gaps corresponds to increasing the lateral gap. Knob 616 is rotated counter clockwise as indicated by arrow 706. Knob 616 rotates threaded shaft 710 counter clockwise to increase the distance between slide block 620 and structure 626. Free wheel gear 618 rotates counter clockwise by engagement with the gear teeth of post 624 in a fixed position (e.g. locked by brake 610) as slide block 620 moves as indicated by arrow 708. The counter clockwise rotation of free wheel gear 618 moves post 622 in a direction indicated by arrow 714 as the gear teeth of post 622 engages with free wheel gear 618. As mentioned, brake 608 is disabled allowing post 622 to move as free wheel gear 618 rotates.

The distraction distance between lateral plate 604 and fixed position plate 602 is increased until the lateral gap is the same as the medial gap. Increasing the medial gap increases the tension on the medial collateral ligament. Conversely, the tension on the medial collateral ligament is not raised significantly because medial plate 606 does not move. In one embodiment, soft tissue release can be practiced on the lateral collateral ligament to reduce the tension and equalize the tensions between the medial collateral ligament and the lateral collateral ligament. Load sensors coupled to medial plate 606 and lateral plate 604 provide load measurement data to the computer whereby the load magnitude data applied to medial plate 606 and lateral plate 604 can be viewed in real-time. Thus, the soft tissue release can be performed until the load magnitude on medial plate 606 and the lateral plate 604 are the same which corresponds to approximately equal lateral and medial collateral ligament tension. Alternatively, the soft tissue release can be performed to set different loadings in each compartment relative to one another. Equalizing the medial and lateral gap is disclosed in FIG. 31 whereby the process of equalization reduces the total error of the femur and tibia in relation to the mechanical axis of the leg as discussed herein above for distractor 10.

In general, the prepared surface of the tibia is resected to align the tibia to the mechanical axis. Note that the distal end of the femur is forcibly aligned to have equal medial and lateral gaps at substantially equal loading in each compartment of the knee which is the process of equalizing or equalization of the knee joint for receiving knee joint prosthetic components. In one embodiment, a guide hole jig can be coupled to distractor 1000 or to the distal end of the femur for drilling guide holes for a bone cutting jig. The guide holes are drilled to align the cutting jig to cut one or more surfaces of the distal end of the femur to produce the equalized knee compartments. The guide holes are drilled at an angle that counters offset of the femur relative to the mechanical axis whereby a prepared surface of the distal end of the femur cut by the femoral cutting jig coupled to the guide holes produces an installed femoral prosthetic component that is aligned to the mechanical axis.

Brake 610 can be released after drilling the guide holes for the equalization process using distractor 1000. Knob 616 can then be rotated clockwise to bring the lateral plate 604 and medial plate 606 to a minimum height. The leg can then be placed in flexion. For example, the leg can be placed where the tibia is at a 90 degree angle relative to the femur.

A similar process to that disclosed herein above using distractor 1000 can be used to equalize the compartments in flexion. In one embodiment, with the leg in flexion, knob 616 is rotated counter clockwise to raise lateral plate 604 and medial plate 606 into contact with a posterior portion of the lateral condyle and a posterior portion of the medial condyle. Knob 616 is rotated counter clockwise until a predetermined load magnitude is measured. The load magnitude on the medial and lateral condyles can be viewed on the display coupled to the computer in real-time that receives load measurement data. Typically, a single condyle will be at the predetermined load magnitude.

The brake is applied to the side that measures the predetermined load magnitude. For example, lateral plate 604 measures at the predetermined load magnitude and brake 608 is applied. Medial plate 606 is free to move by rotation of knob 616. Knob 616 is rotated counter clockwise to increase the distraction distance between medial plate 606 and fixed position plate 602 thereby increasing the load magnitude applied to medial plate 606. The increase in load magnitude and the distraction distance is displayed on the display coupled to the computer receiving load measurement data and distraction distance data. In one embodiment, the distraction distance between medial plate 606 and fixed position plate 602 is increased until the predetermined load magnitude is measured. Thus, the load magnitude on medial plate 606 and lateral plate 604 are equal to the predetermined load magnitude. The height of the medial compartment and the height of the lateral compartment can be different at the predetermined load magnitude. For example the lateral compartment height can be greater than the lateral compartment height.

Brake 608 is released with the load magnitude applied to the medial plate 606 equal to the load magnitude applied to the lateral plate 604. Brake 610 is enabled such that medial plate 606 cannot move. Knob 606 is rotated counter clockwise to increase the distraction distance between medial plate 604 and fixed position plate 602. The distraction distance is increased until the lateral compartment height is equal to the medial compartment height. Increasing the distraction distance between lateral plate 604 and fixed position plate 602 will increase the tension on the lateral collateral ligament. After the medial compartment height and the lateral compartment height are equalized in flexion the tension on the lateral collateral ligament will be greater than the tension on the medial collateral ligament. In one embodiment, a drill guide can be coupled to distractor 1000 or the distal end of the femur 700. Drill guide holes are drilled into the distal end of the femur with the medial gap and the lateral gap equalized to support at least one bone cut for installation of a femoral prosthetic component. The load magnitude applied to the lateral plate 604 and the medial plate 606 can also be equalized. For example, soft tissue release can be used to reduce the tension of the lateral collateral ligament until the measured load magnitude on the lateral plate 604 equals the load magnitude on the medial plate 606. Thus, the installation of the femoral prosthetic component on the distal end of femur 700 results in the medial compartment of the knee joint spaced equal to the lateral compartment (or a spacing chosen by the surgeon), equal load magnitudes applied in each compartment (or a load distribution chosen by the surgeon), with the leg in alignment to the mechanical axis. Note also that the equalization is performed in the leg in extension and flexion thereby maintaining the alignment and balance throughout the range of motion. In general, the measurement data generated during the use of distractor 1000 should correspond to measurement data generated after installation of the final prosthetic components of the knee joint.

Figure 51:
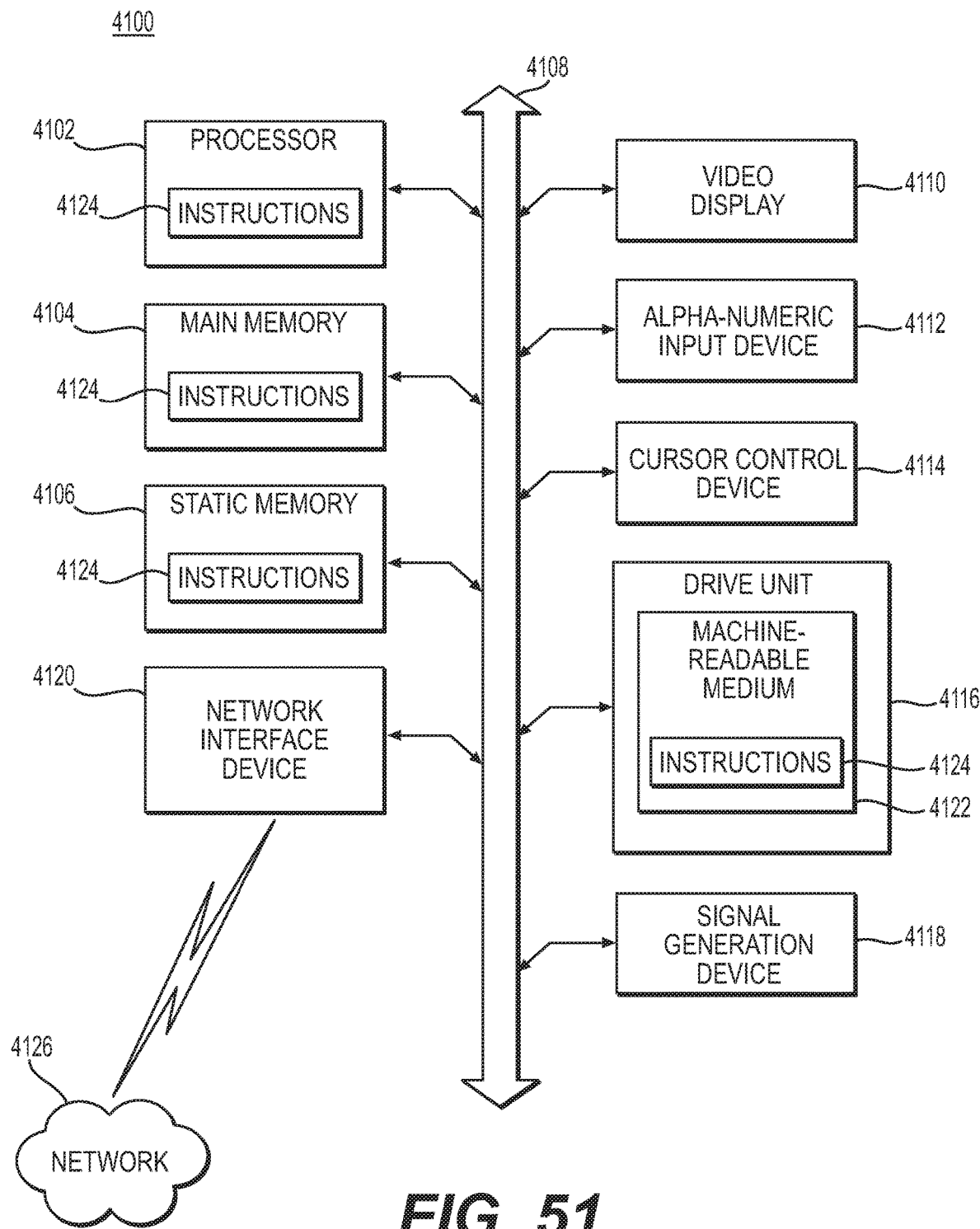
FIG. 51 depicts an exemplary diagrammatic representation of a machine in the form of a system in accordance of an example embodiment.

FIG. 51 depicts an exemplary diagrammatic representation of a machine in the form of a system 4100 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 4100 may include a processor 4102 (e.g., a central processing unit (CPU), a graphics processing unit (GPU, or both), a main memory 4104 and a static memory 4106, which communicate with each other via a bus 4108. System 4100 may further include a video display unit 4110 (e.g., a liquid crystal display (LCD), a flat panel, a solid state display, or a cathode ray tube (CRT)). System 4100 may include an input device 4112 (e.g., a keyboard), a cursor control device 4114 (e.g., a mouse), a disk drive unit 4116, a signal generation device 4118 (e.g., a speaker or remote control) and a network interface device 4120.

The disk drive unit 4116 can be other types of memory such as flash memory and may include a machine-readable medium 4122 on which is stored one or more sets of instructions (e.g., software 4124) embodying any one or more of the methodologies or functions described herein, including those methods illustrated above. Instructions 4124 may also reside, completely or at least partially, within the main memory 4104, the static memory 4106, and/or within the processor 4102 during execution thereof by the system 4100. Main memory 4104 and the processor 4102 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 4124, or that which receives and executes instructions 4124 from a propagated signal so that a device connected to a network environment 4126 can send or receive voice, video or data, and to communicate over the network 4126 using the instructions 4124. The instructions 4124 may further be transmitted or received over a network 4126 via the network interface device 4120.

While the machine-readable medium 4122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 52:
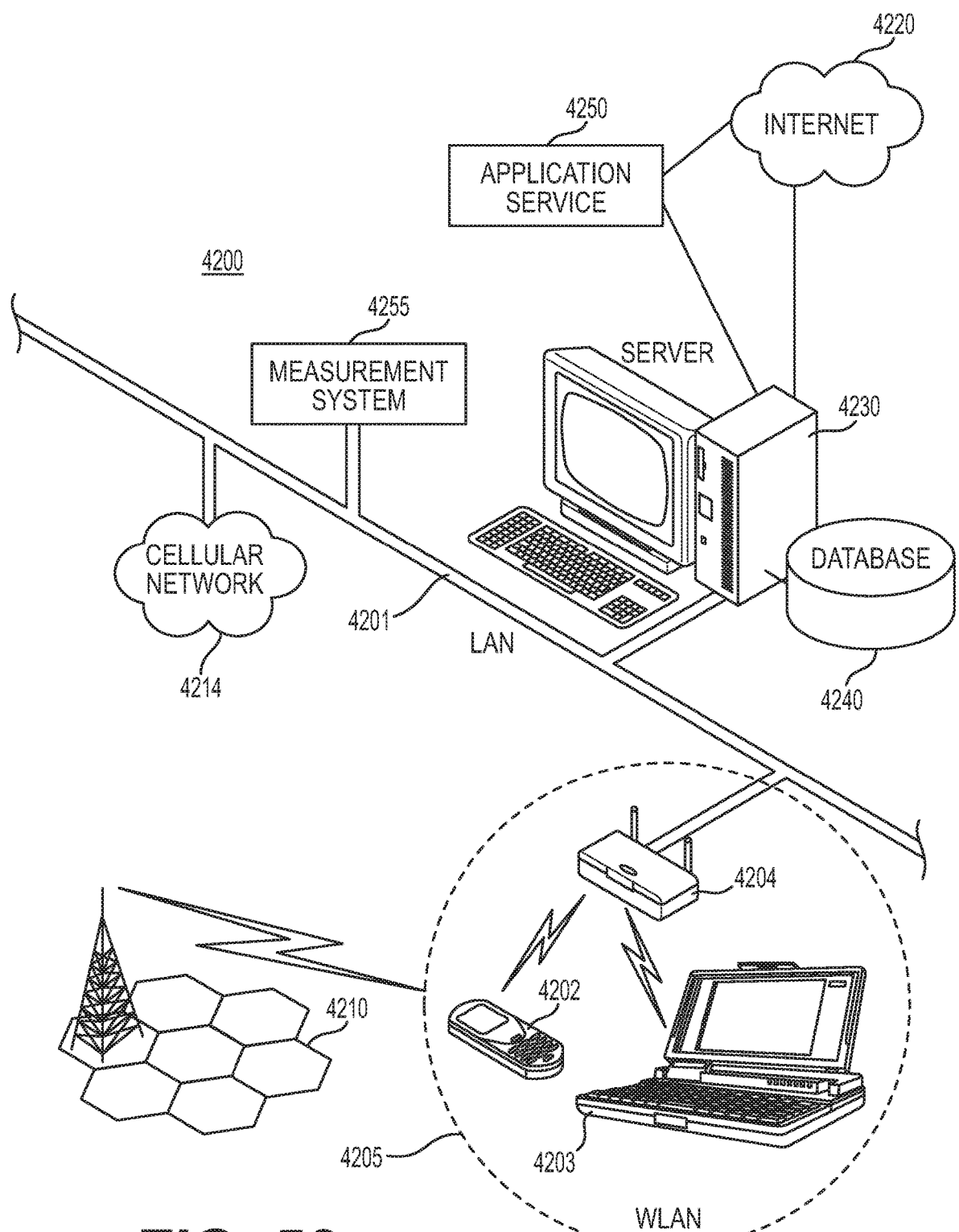
FIG. 52 is an illustration of a communication network for measurement and reporting in accordance with an exemplary embodiment.

FIG. 52 is an illustration of a communication network 4200 for measurement and reporting in accordance with an exemplary embodiment. Briefly, the communication network 4200 expands broad data connectivity to other devices or services. As illustrated, the measurement and reporting system 4255 can be communicatively coupled to the communications network 4200 and any associated systems or services.

As one example, measurement system 4255 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 4200 can further be tied to an Electronic Medical Records (EMR) system to implement health information technology practices. In other embodiments, the communication network 4200 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 4200 can provide wired or wireless connectivity over a Local Area Network (LAN) 4201, a Wireless Local Area Network (WLAN) 4205, a Cellular Network 4214, and/or other radio frequency (RF) system (see FIG. 4). The LAN 4201 and WLAN 4205 can be communicatively coupled to the Internet 4220, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 4200 can utilize common computing and communications technologies to support circuit-switched and/or packet-switched communications. Each of the standards for Internet 4220 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 4214 can support voice and data services over a number of access technologies such as GSM-GPRS, EDGE, CDMA, UMTS, WiMAX, 2G, 3G, WAP, software defined radio (SDR), and other known technologies. The cellular network 4214 can be coupled to base receiver 4210 under a frequency-reuse plan for communicating with mobile devices 4202.

The base receiver 4210, in turn, can connect the mobile device 4202 to the Internet 4220 over a packet switched link. The internet 4220 can support application services and service layers for distributing data from the measurement system 4255 to the mobile device 4202. Mobile device 4202 can also connect to other communication devices through the Internet 4220 using a wireless communication channel.

The mobile device 4202 can also connect to the Internet 4220 over the WLAN 4205. Wireless Local Access Networks (WLANs) provide wireless access within a local geographical area. WLANs are typically composed of a cluster of Access Points (APs) 4204 also known as base stations. The measurement system 4255 can communicate with other WLAN stations such as laptop 4203 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 4200, the measurement system 4255 can establish connections with a remote server 4230 on the network and with other mobile devices for exchanging data. The remote server 4230 can have access to a database 4240 that is stored locally or remotely and which can contain application specific data. The remote server 4230 can also host application services 4250 directly, or over the internet 4220.

In general, a robot can support or assist the distraction of a knee joint in under control of a surgeon. The distractor 10 or distractor 1000 disclosed herein above can be coupled to the robot. One example of the robot is the Robodoc surgical robot with a robotic assisted TKA application. A robot can also include surgical CNC robots, surgical haptic robots, surgical teleoperative robots, surgical hand-held robots, or any other surgical robot. Distractor 10 can be automated to couple to and work with the robot thereby replacing direct hand control by the surgeon. The actions taken by the robot in control of distractor 10 can be smoother and more accurate by having the robot use the measurement data in real-time and providing feedback to distractor 10 for subsequent steps. An added benefit can be shortening the time of surgery that reduces the time a patient is under anesthesia.

The robot can be configured to perform computer-assisted surgery and more specifically knee surgery with distractor 10. Typically, the robot and distractor 10 is used for computer-assisted surgery to improve performance, reduce time, and minimize variation in the distraction, alignment, bone cuts, and installation of one or more prosthetic components for a prosthetic knee joint. The robot can control distraction, medial-lateral tilt, loading, tissue release, braking, and drilling guide holes using the real-time measurement data sent from distractor 10.

In general, measurement data from distractor 10 can be wirelessly transmitted to a computer of the robot. Alternatively, the measurement data can be hard wired to the robot. Examples of measurement data from distractor 10 can be position data, distraction distance, load, medial-lateral tilt, or other data relevant to a prosthetic knee installation. The measurement data received by the robot can be further processed to calculate and display measurement data needed by the surgeon for the distraction and preparation of the bone surfaces of the knee joint. The prepared bone surfaces will receive a prosthetic component that supports alignment to the mechanical axis of the leg. In one embodiment, the computer includes one or more algorithms that are used at various stages of the surgery. The measurement data is input to the algorithms of the robot and the algorithms can convert the data into information displayed on the display for robotic actions that are used to make bone cuts, pin placements, prosthetic component sizing, etc. . . . or provide feedback on actions that the surgeon may take. The feedback may take the form of audible, visual, or haptic feedback that guides the surgeon on the distraction or subsequent steps taken by the robot to support or resist an action based on the measurement data. The feedback can also smooth or prevent motions by a user that could be detrimental to the surgery. Furthermore, the status of the measurement data can be used to generate a workflow that is subsequently implemented by a surgeon or automatically by the robot to enhance performance and reliability of the knee joint installation.

Referring to FIGS. 1-3, a surgical apparatus 10 is disclosed comprising a fixed support structure 28, a moving support structure 30, and a distraction mechanism 24. Distraction mechanism 24 moves moving support structure 30 relative to fixed support structure 28. Fixed support structure 28 couples to housing 20 of surgical support apparatus 10. Fixed support structure 28 includes a frame 36 having an opening. Moving support structure 30 couples to a distal end of femur 16. Frame 36 of fixed support structure 36 couples to a proximal end of tibia 18. In one embodiment, the proximal end of tibia 18 has a prepared bone surface. The prepared bone surface is cut referenced to the anatomical or mechanical axis of the leg. The prepared bone surface can have a predetermine anterior-posterior (A-P) slope. In one embodiment, the leg is placed in extension when surgical apparatus 10 is inserted. Typically, surgical apparatus 10 is inserted with the moving support structure 30 and the fixed support structure 28 in a minimum height position. In one embodiment, moving support structure 30 fits within frame 36. In one embodiment, the minimum height position corresponds to a bottom surface 34 of frame 36 and a bottom surface of moving support structure 30 coupling to the prepared bone surface of tibia 18.

In one embodiment, a module 32 having a cover 38 is aligned and retained to moving support structure 30. Module 32 includes electronic circuitry and one or more sensors to measure one or more parameters. Module 32 is configured to control a measurement process and to transmit module measurement data. In one embodiment, module 32 can measure leg position, load magnitude applied to the medial or lateral sides of module 32, position of load on the medial or lateral side of module 32, alignment, and other parameters. The module measurement data is transmitted to a computer 12 having a display 14. The module measurement data can be processed and displayed in different formats on display 14 to provide information at a glance.

Similarly, surgical apparatus 10 can have electronic circuitry and one or more sensors. The electronic circuitry can control a measurement process and transmit apparatus measurement data. In one embodiment, surgical apparatus 10 can measure a M-L tilt angle, a first compartment height, a second compartment height, or an average of the first and second compartment heights and display the apparatus measurement data on display 14 of computer 12. The apparatus measurement data can be transmitted to computer 12 for further processing and displayed on display 14. In one embodiment, the M-L tilt angle can be measured by a Hall Effect Sensor coupled to moving support structure 30. The height of the first compartment or the height of the second compartment can be measured by a Linear Hall Sensor coupled to moving support structure 30. Alternatively, one or more gauges can be placed on surgical apparatus 10 for viewing by the user. The one or more gauges can be mechanical or electrical gauges.

A distraction mechanism 24 of surgical apparatus 10 is configured to raise and lower the moving support structure 30 relative to fixed support structure 28. In general, distraction mechanism 24 is adjusted in height until a first compartment of the knee joint is at a first predetermined load value. Typically the first predetermined load value is in a range of 20-40 lbs of loading. In one embodiment, moving support structure 30 can pivot medially or laterally as the height is adjusted to the first predetermined load value. The second compartment will measure a loading less than the first predetermined load value. In one embodiment, the height of the second compartment will also be less than the height of the first compartment. The use of the term first compartment is arbitrary as it can be either the medial compartment or the lateral compartment of the knee joint being set to the first predetermined load value initially. For example, if the first compartment at the first predetermined load value is the medial compartment then a second compartment is the lateral compartment. Conversely, if the first compartment at the first predetermined load value is the lateral compartment then the second compartment is the medial compartment.

The first and second compartments are at different heights when the first compartment is at the first predetermined load value. As mentioned previously, moving support structure 30 is allowed to swing medial or laterally as the loading is increased by increasing the height of the first compartment. After setting the first compartment to the first predetermined load value a distraction lock mechanism 124 of FIG. 14 is engaged. In one embodiment, distraction lock mechanism 124 is couples to gear 128 thereby preventing knob 26 from rotating. Distraction lock mechanism 124 prevents a height of moving support structure from changing. M-L (medial-lateral) tilt mechanism 22 is then engaged to equalize the first and second compartments. Moving support structure 30 will no longer freely pivot medially or laterally when M-L tilt mechanism 22 is engaged. In one embodiment, a process of equalization requires the second compartment to be forcibly raised until it is at the first predetermined height of the first compartment. The M-L tilt angle will be at zero when the first and second compartments are equalized. The M-L tilt angle is measured by the Hall Effect Sensor or a gauge on the surgical apparatus. The medial and lateral compartment height or the average compartment height is measured by the Linear Hall Sensor or a gauge. The first M-L tilt angle corresponds to an alignment error that is reduced by equalization and introduced into a bone cut. In one embodiment, loading on the first or second compartments can be adjusted or fine-tuned after equalization. For example, soft tissue tensioning can be performed to change loading with the load measurements being monitored on display 14 in real-time.

In general, at least one bone cut is made to femur 16 in extension to support installation of a femoral prosthetic component with equalization to reduce alignment error. The at least one bone cut relates to the first and second compartments equalized and the M-L tilt angle. The equalized first and second compartment reduces the alignment error of the femur as shown in FIG. 32 thereby rendering a knee joint installation having a femur 400 and tibia 402 in improved alignment with a mechanical axis of the leg. The bone cut also supports installation of the femoral prosthetic component incorporating the reduced alignment error. Referring to FIG. 34, a drill guide 402 is configured to couple to surgical apparatus 10. In one embodiment, surgical apparatus 10 includes a drill guide retaining device to retain and align drill guide 402 for drilling two or more holes for mounting a bone cutting jig. In one embodiment drill guide 402 is aligned to femur 400 and at least two holes are drilled. The at least two holes drilled correspond to or are related to the M-L tilt measured when the first compartment and the second compartment are equalized. A bone cutting jig can be mounted to the at least two holes and a bone cut is made to femur 400 to support installation of a femoral prosthetic component. In general, installation of the femoral prosthetic component will have load measurements in the medial compartment and the lateral compartment similar to the first predetermined load value in extension and improved alignment to the mechanical axis of the leg in extension.

Referring to FIGS. 36-43, surgical apparatus 10 is placed at the minimum height with the leg is moved into flexion. In one embodiment, the leg is placed at a 90 degree angle. In general, the process listed below is done at least once in flexion but can be done more than one time at different flexion angles to optimize performance of the knee joint over the range of motion. In general, with the leg in flexion distraction mechanism 24 is adjusted in height until one of the first compartment or the second compartment of the knee joint is at a second predetermined load value. The second predetermined load value can be the same as the first predetermined load value or it can be different. Moving support structure 30 is allowed to pivot medially or laterally as the height is adjusted to the second predetermined load value in flexion. Similar to the leg in extension, the height of the first compartment in flexion, the height of the second compartment in flexion, leg position, the rotation balance angle in flexion, loading on the first compartment in flexion, loading on the second compartment, in flexion, contact point on the first compartment, and contact point on the second compartment are all monitored and captured in real-time.

Equalization is performed using surgical apparatus 10 in which moving support structure 30 is no longer allowed to swing freely. Distraction lock mechanism 124 is engaged to prevent distraction mechanism 24 from raising or lowering moving support structure 30. M-L tilt mechanism 22 is engaged to forcibly change the M-L tilt angle under user control such that the first and second compartments in flexion have equal compartment heights. Engaging M-L tilt mechanism 22 prevents moving support structure 30 from freely pivoting medially or laterally. In one embodiment, the compartment (medial or lateral) not at the second predetermined load value is forcibly changed to have an equal height as the compartment at the second predetermined load value. In one embodiment, the compartment not at the second predetermined load value will have a height less than the compartment at the second predetermined load value. The rotation balance angle corresponds to the M-L tilt angle of moving support structure 30 with the leg in flexion at the second predetermined value. After equalization the M-L tilt angle will be zero. In one embodiment, the loading applied to the first compartment and the second apartment can be adjusted. For example, soft tissue tensioning can be performed. The measurement data is transmitted, processed by computer 12, and displayed by display 14.

Referring to FIGS. 39-43, sizers 510, 540, 542, 544, and 546 are used to determine implant size of the femoral prosthetic component. In the example, sizer 510 is configured to be coupled to surgical apparatus 10. Different sizers can be installed and coupled to the femur to support a femoral prosthetic component choice. The surgical apparatus 10 is configured to support drilling two or more holes in the femur in flexion in support of one of sizers 510, 540, 542, 544, and 546. The two or more holes drilled into the femur in flexion correspond to the balanced rotation angle. A cutting jig can be coupled to the two or more holes to make one or more bone cuts to support installation of the femoral prosthetic component with the first and second compartments equalized in flexion.

A method of decreasing musculoskeletal alignment error is disclosed using surgical apparatus 10. The method can be practiced with more or less than the steps shown, and is not limited to the order of steps shown. The method is not limited to the knee joint example but can be used for hip, shoulder, ankle, elbow, spine, hand, foot, bone, and other areas musculoskeletal system. The method can be referred to in FIGS. 1-3 and FIGS. 26-50. In a first step, a surgical apparatus 10 is inserted into a knee joint with a leg in extension. A frame 36 of a fixed support structure 28 couples to a prepared surface of a tibia. A bottom surface 42 of a moving support structure contacts the prepared surface of the tibia. The first compartment of the knee joint is distracted to a first predetermined load value. Surgical apparatus 10 includes a distraction mechanism 24 configured to distraction a first compartment, a second compartment, or both compartments. Typically, the load value is selected within a range of 20-40 lbs of loading. Moving support structure 30 is configured to pivot freely medially or laterally.

Frame 36 of fixed support structure 28 has an opening. In one embodiment, the opening is larger than moving support structure 30. Moving support structure 30 is configured to fit with the opening of frame 36. In one embodiment, moving support structure 30 can be lowered by distraction mechanism 24 within frame 36 such that bottom surface 42 of moving support structure 30 contacts the prepared surface of the tibia during insertion. In one embodiment, moving support structure 30 contacting the prepared surface of the tibia is a minimum height that surgical apparatus 10 can achieve. In one embodiment, frame 36 surrounds at least a portion of moving support structure 30. Frame 36 is rigid and does not flex during distraction. In one embodiment, moving support structure 30 can be lowered within frame 36 whereby bottom surface 34 of frame 36 and support structure 28 is co-planar to bottom surface 42 of moving support structure 30.

In a second step, a module 32 is placed on moving support structure 30 prior to insertion. A cover 38 can also be placed on moving support structure 30. Module 32 can include electronic circuitry 150, a power source 60, and one or more sensors. Electronic circuitry 150 is configured to control a measurement process and transmit measurement data to a computer 12. Computer 12 can receive, process, and display the measurement data on a display 14. In one embodiment, module 32 can measure position, leg position, alignment, loading on a medial compartment and a lateral compartment, position of load on the medial and lateral compartments, rotation, and other parameters in real-time.

In a third step, the medial-lateral (M-L) tilt angle of moving support structure 30 is measured and displayed on display 14 of computer 12. In one embodiment, the M-L tilt angle is measured by a Hall Effect sensor in surgical apparatus 10. The distraction height of the medial compart, the lateral compartment, or average height is measured and displayed on display 14 of computer 12. In one embodiment, the distraction height is measured by a Linear Hall sensor. In one embodiment, electronic circuitry 150 is coupled to the Hall Effect Sensor and the Linear Hall sensor in surgical apparatus 10. Electronic circuitry 150 is configured to control the measurement of the M-L tilt angle and distraction height and transmit the measurement data.

In a fourth step, distraction mechanism 24 is locked. A distraction lock mechanism is engaged to prevent movement of distraction mechanism 24. In one embodiment, distraction mechanism 24 comprises one or more gears. In one embodiment, distraction lock mechanism 124 couples to one or more teeth of the one or more gears such that the one or more gears cannot move thereby locking the distraction mechanism 24 at a height corresponding to the predetermined load value.

In a fifth step, the first and second compartments are equalized. Equalization is a process of raising a height of the second compartment to equal the first compartment height at the predetermined load value. Equalizing the first and second compartments reduces alignment error of the leg. In one embodiment, at least one bone cut is made to a femur for receiving a femoral prosthetic component that reduces alignment error of the leg. The at least one bone cut takes into account the equalization or M-L tilt angle to reduce the alignment error when the femoral prosthetic component is installed on the femur. In one embodiment, the loading of the first or second compartment can be adjusted.

In a sixth step, the process of equalization engages the M-L tilt mechanism 22 of surgical apparatus 10. In one embodiment, M-L tilt mechanism 22 comprises at least one worm gear. M-L tilt mechanism 22 when disengaged allows moving support structure 30 to freely swing medially and laterally. M-L tilt mechanism 22 has a pivot or a pivot point that supports medial or lateral movement. M-L tilt mechanism 22 when engaged prevents moving support structure 30 from freely moving medially or laterally. In one embodiment, M-L tilt mechanism 22 is engaged to forcibly change the M-L tilt angle to zero under user control. Changing the M-L tilt angle to zero equalizes the second compartment height equal to the first compartment height that is at the predetermined load value. In one embodiment, M-L tilt mechanism 22 is coupled between distraction mechanism 24 and moving support structure 30. In one embodiment, M-L tilt mechanism 22 is self-locking.

In a seventh step, a drill guide 492 is coupled to surgical apparatus 10. At least two holes 496 are drilled into the femur. The orientation of the at least two holes 496 relate to the equalization or the M-L tilt angle. A bone cutting jig is coupled to a distal end of a femur through the at least two holes 496. The bone cutting jig is aligned to cut the femur oriented to the at least two holes 496 and at least one bone cut is made. A femoral prosthetic component is coupled to and aligned to the at least one bone cut. The femoral prosthetic component is oriented on the femur to reduce alignment error of the leg where the orientation relates to the equalization or the M-L tilt angle.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or surgical apparatus may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A surgical apparatus comprising:
a fixed support structure configured to couple to a proximal end of a tibia;
a moving support structure configured to couple to a distal end of a femur wherein a leg is in extension, the moving support structure including a coupler extending along a first axis; and
a distraction mechanism configured to raise and lower the moving support structure relative to the fixed support structure; and
a tilt mechanism coupled to the distraction mechanism, the tilt mechanism including an opening extending along a second axis to receive the coupler to couple the moving support structure to the tilt mechanism, the first axis being aligned with the second axis when the moving support structure is coupled to the tilt mechanism, wherein the tilt mechanism is configured to forcibly change a tilt angle of the moving support structure under user control when the moving support structure is coupled to the tilt mechanism, the coupler being configured to rotate the moving support structure around the first axis.

2. The surgical apparatus of claim 1 further including:
a key configured to couple to the tilt mechanism wherein the key is configured to be rotated by a user to forcibly change the tilt angle when the surgical apparatus is under load by a musculoskeletal system;
a module coupled to the moving support structure wherein the module includes electronic circuitry and a plurality of sensors, wherein the module is configured to measure load and position of load, and wherein module measurement data is transmitted to a computer and displayed on a display of the computer.

3. The surgical apparatus of claim 1 further including:
a Linear Hall sensor configured to measure a height of a first compartment, a height of a second compartment, or an average height of the first compartment and the second compartment, and wherein the height of the first compartment, the height of the second compartment, or the average height of the first compartment and the second compartment is displayed on a display of a computer; and
a Hall Effect sensor configured to measure a M-L tilt angle of the moving support structure.

4. The surgical apparatus of claim 1 wherein a distraction lock mechanism is engaged to prevent further movement of the distraction mechanism and wherein the surgical apparatus is configured to equalize a height of first and second compartments whereby a M-L tilt angle is zero.

5. The surgical apparatus of claim 4 wherein forcibly changing the M-L tilt angle to zero reduces a leg alignment error.

6. The surgical apparatus of claim 5 wherein a drill guide is configured to be coupled to the surgical apparatus, wherein the drill guide is configured to support drilling of at least two holes related to the equalization, and wherein a bone cutting jig is configured to couple to the at least two holes, and wherein the bone cutting jig is configured to support at least one bone cut to the femur.

7. The surgical apparatus of claim 6 wherein the surgical apparatus is configured to support movement of the leg into a position of flexion, wherein the distraction mechanism is configured to be adjusted until one of the first or second compartments is at a second predetermined load value in flexion, and wherein the surgical apparatus is configured to measure a rotation balance angle, a height of the first compartment in flexion, a height of the second compartment in flexion, a load magnitude applied to the first compartment in flexion, a load magnitude applied to the second compartment in flexion, a position of load applied to the first compartment in flexion, and a position of load applied to the second compartment in flexion.

8. The surgical apparatus of claim 7 wherein a distraction lock mechanism is engage to prevent further movement of the distraction mechanism and wherein the tilt mechanism is configured to forcibly change the M-L tilt angle in flexion to equalize the first and second compartment heights in flexion.

9. The surgical apparatus of claim 8 wherein a sizer is configured to be coupled to the surgical apparatus to determine an implant size, wherein the surgical apparatus is configured to support drilling two or more holes in the femur in flexion, wherein a bone cutting jig is configured to couple to the two or more holes in the femur in flexion corresponding to the balanced rotation angle, and wherein one or more bone cuts are configured to be made to support installation of a femoral prosthetic component.

10. The surgical apparatus of claim 1 wherein the tilt mechanism comprises a worm gear drive configured to forcibly change the tilt angle of the moving support structure and wherein the worm gear drive is configured to be self-locking to hold a position of the moving support structure.

11. A surgical apparatus comprising:
a fixed support structure configured to couple to a proximal end of a tibia;
a moving support structure configured to couple to a distal end of a femur wherein a leg is in extension, the moving support structure including a coupler extending along a first axis; and
a distraction mechanism configured to raise and lower the moving support structure relative to the fixed support structure;
a tilt mechanism coupled to the distraction mechanism, the tilt mechanism including an opening extending along a second axis to receive the coupler to couple the moving support structure to the tilt mechanism, the first axis being aligned with the second axis when the moving support structure is coupled to the tilt mechanism, wherein the tilt mechanism includes a worm gear drive configured to be self-locking to hold a position of the moving support structure when the moving support structure is coupled to the tilt mechanism, the coupler being configured to rotate the moving support structure around the first axis when the moving support structure is coupled to the tilt mechanism.

12. The surgical apparatus of claim 11 wherein a height of a first compartment of a knee joint is adjusted to a predetermined load value while the moving support structure can freely pivot medially or laterally and wherein the tilt mechanism is engaged to equalize a second compartment to a height of a first compartment thereby reducing an alignment error of the leg and wherein a distraction lock mechanism is engaged during equalization to prevent movement of the distraction mechanism.

13. The surgical apparatus of claim 12 wherein the surgical apparatus is configured to measure a M-L tilt angle of the moving support structure, wherein a key is configured to couple to the tilt mechanism, wherein the key is configured to be rotated by a user to forcibly change the tilt angle when the surgical apparatus is under load by a musculoskeletal system, and wherein the tilt mechanism when engaged is configured to forcibly change the M-L tilt angle under user control.

14. The surgical apparatus of claim 13 further including coupling a drill guide to the surgical apparatus wherein the drill guide is configured support drilling at least two holes into the femur related to equalization.

15. The surgical apparatus of claim 14 wherein a bone cutting jig is configured to couple to the at least two holes, and wherein the bone cutting jig is configured to support at least one bone cut to the femur that reduces the alignment error of the leg when a femoral prosthetic component is installed.

16. A surgical apparatus comprising:
a fixed support structure configured to couple to a proximal end of a tibia;
a moving support structure configured to couple to a distal end of a femur wherein a leg is in flexion, the moving support structure including a coupler extending along a first axis; and
a distraction mechanism configured to raise and lower the moving support structure relative to the fixed support structure wherein a height of a first compartment of a knee joint is adjusted to a predetermined load value;
a tilt mechanism coupled to the distraction mechanism, the tilt mechanism including an opening extending along a second axis to receive the coupler to couple the moving support structure to the tilt mechanism, the first axis being aligned with the second axis when the moving support structure is coupled to the tilt mechanism, wherein a key is configured to couple to the tilt mechanism, wherein the key is rotated under user control to forcibly rotate the coupler to a predetermined M-L tilt when the moving support structure is coupled to the tilt mechanism, the coupler configured to pivot the moving support structure about the first axis when the moving structure is coupled to the tilt mechanism, wherein the tilt mechanism is engaged to equalize a second compartment to a height of the first compartment.

17. The surgical apparatus of claim 16 wherein a distraction lock mechanism is engaged during equalization in flexion to prevent movement of the distraction mechanism.

18. The surgical apparatus of claim 17 wherein the surgical apparatus is configured to measure a balanced rotation angle of the moving support structure.

19. The surgical apparatus of claim 18 wherein a sizer is configured to be coupled to the surgical apparatus to determine an implant size and wherein the surgical apparatus is configured to support drilling two or more holes in the femur in flexion and wherein a bone cutting jig is configured to couple to the two or more holes in the femur in flexion corresponding to the balanced rotation angle and wherein one or more bone cuts are configured to be made to support installation of a femoral prosthetic component.

20. The surgical apparatus of claim 16 wherein the tilt mechanism comprises a worm gear drive configured to forcibly change a tilt of the moving support structure under load by a musculoskeletal system and wherein the worm gear drive is configured to be self-locking to hold a position of the moving support structure.

* * * * *